US010618900B2

(12) United States Patent
Liu et al.

(10) Patent No.: US 10,618,900 B2
(45) Date of Patent: Apr. 14, 2020

(54) 5-AROMATIC ALKYNYL SUBSTITUTED BENZAMIDE COMPOUND AND PREPARATION METHOD, PHARMACEUTICAL COMPOSITION, AND USE THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Yu Zhou, Shanghai (CN); Dong Zhang, Shanghai (CN); Jian Li, Shanghai (CN); Hualiang Jiang, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/566,418

(22) PCT Filed: Apr. 15, 2016

(86) PCT No.: PCT/CN2016/079496
§ 371 (c)(1),
(2) Date: Feb. 27, 2018

(87) PCT Pub. No.: WO2016/165658
PCT Pub. Date: Oct. 20, 2016

(65) Prior Publication Data
US 2018/0194767 A1    Jul. 12, 2018

(30) Foreign Application Priority Data
Apr. 15, 2015   (CN) .......................... 2015 1 0179677

(51) Int. Cl.
C07D 487/04    (2006.01)
C07D 401/12    (2006.01)
C07D 239/26    (2006.01)
C07D 417/06    (2006.01)
C07D 417/10    (2006.01)
C07D 417/12    (2006.01)
C07D 417/14    (2006.01)
C07D 277/30    (2006.01)
(Continued)

(52) U.S. Cl.
CPC ......... *C07D 487/04* (2013.01); *C07D 213/56* (2013.01); *C07D 213/75* (2013.01); *C07D 213/82* (2013.01); *C07D 231/56* (2013.01); *C07D 239/26* (2013.01); *C07D 261/08* (2013.01); *C07D 263/32* (2013.01); *C07D 277/30* (2013.01); *C07D 277/32* (2013.01); *C07D 401/06* (2013.01); *C07D 401/10* (2013.01); *C07D 401/12* (2013.01); *C07D 401/14* (2013.01); *C07D 413/10* (2013.01); *C07D 413/12* (2013.01); *C07D 417/06* (2013.01); *C07D 417/10* (2013.01); *C07D 417/12* (2013.01); *C07D 417/14* (2013.01); *C07D 491/10* (2013.01)

(58) Field of Classification Search
CPC .. C07D 213/56; C07D 213/75; C07D 213/82; C07D 231/56; C07D 239/26; C07D 263/08; C07D 263/32; C07D 277/30; C07D 277/32; C07D 401/06; C07D 401/10; C07D 401/12; C07D 401/14; C07D 413/10; C07D 413/12; C07D 417/06; C07D 417/10; C07D 417/12; C07D 417/14; C07D 487/04; C07D 491/10
See application file for complete search history.

(56) References Cited

U.S. PATENT DOCUMENTS 6,656,957 B1   12/2003   Allgeier et al.
7,776,869 B2    8/2010   Chaffee et al.
(Continued)

FOREIGN PATENT DOCUMENTS

CN   103596568      *  2/2014   ........... A61K 31/495
CN   103596568 A       2/2014
(Continued)

OTHER PUBLICATIONS

Dimova, et al., Computational chemical biology: identification of small molecular probes that discriminate between members of target protein families, Chemical Biology & Drug Design (2012), 79(4), 369-375. (Year: 2012).*

(Continued)

*Primary Examiner* — Erich A Leeser
(74) *Attorney, Agent, or Firm* — Panitch Schwarze Belisario & Nadel LLP

(57) ABSTRACT

Compounds of formula I are provided. Also provided are methods of preparing the compounds of formula (I), and methods of using the compounds of formula (I) as a negative allosteric modulator of a metabotropic glutamate receptor (mGluR) subtype 5.

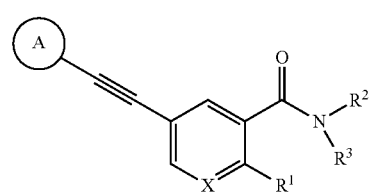

17 Claims, 1 Drawing Sheet

(51) Int. Cl.
*C07D 213/56* (2006.01)
*C07D 213/75* (2006.01)
*C07D 213/82* (2006.01)
*C07D 401/10* (2006.01)
*C07D 277/32* (2006.01)
*C07D 231/56* (2006.01)
*C07D 261/08* (2006.01)
*C07D 263/32* (2006.01)
*C07D 401/06* (2006.01)
*C07D 401/14* (2006.01)
*C07D 413/10* (2006.01)
*C07D 413/12* (2006.01)
*C07D 491/10* (2006.01)

(56) References Cited

U.S. PATENT DOCUMENTS

| | | |
|---|---|---|
| 2009/0042855 A1 | 2/2009 | Conn et al. |
| 2011/0294858 A1 | 12/2011 | Conn et al. |

FOREIGN PATENT DOCUMENTS

| | | | |
|---|---|---|---|
| JP | H10195063 A | 7/1998 | |
| JP | H11506425 A | 6/1999 | |
| JP | 2014513078 A | 5/2014 | |
| RU | 2203889 C2 | 5/2003 | |
| WO | 9633181 A1 | 10/1996 | |
| WO | 9902497 A2 | 1/1999 | |
| WO | 0153274 A1 | 7/2001 | |
| WO | WO 2001/53274 * | 7/2001 | ........... C07D 241/18 |
| WO | 2004018428 A1 | 3/2004 | |
| WO | 2005094822 A1 | 10/2005 | |
| WO | 2005094882 A1 | 10/2005 | |
| WO | 2006029980 A1 | 3/2006 | |
| WO | 2006044823 A2 | 4/2006 | |
| WO | 2009143404 A1 | 11/2009 | |
| WO | WO 2009/143404 * | 11/2009 | ........... C07D 213/74 |
| WO | 2010124047 A1 | 10/2010 | |
| WO | WO 2010/124047 * | 10/2010 | ........... C07D 209/44 |
| WO | 2012139027 A1 | 10/2012 | |
| WO | 2012173521 A2 | 12/2012 | |
| WO | 2013101281 A1 | 7/2013 | |
| WO | WO 2013/101281 * | 7/2013 | ........... A61K 31/495 |
| WO | 2013162727 A1 | 10/2013 | |

OTHER PUBLICATIONS

Int'l Search Report dated Jul. 21, 2016 in Int'l Application No. PCT/CN2016/079496.
Cee et al., "Alkynylpyrimidine Amide Derivatives as Potent, Selective, and Orally Active Inhibitors of Tie-2 Kinase," J. Med. Chem., vol. 50, pp. 627-640 (2007).
Extended European Search Report dated Aug. 14, 2018 in EP Application No. 16779633.3.
Office Action dated May 21, 2018 in AU Application No. 2016248388.
Office Action dated Sep. 3, 2018 in JP Application No. 2017554023.
Office Action dated Oct. 30, 2018 in RU Application No. 2017139564/04.
Search Report dated Oct. 30, 2018 in RU Application No. 2017139564/04.

* cited by examiner

5-AROMATIC ALKYNYL SUBSTITUTED BENZAMIDE COMPOUND AND PREPARATION METHOD, PHARMACEUTICAL COMPOSITION, AND USE THEREOF

CROSS-REFERENCE TO RELATED APPLICATION

This application is a Section 371 of International Application No. PCT/CN2016/079496, filed Apr. 15, 2016, which was published in the Chinese language on Oct. 20, 2016, under International Publication No. WO 2016/165658 A1, which claims priority under 35 U.S.C. § 119 (b) to Chinese Application No. 201510179677.0, filed Apr. 15, 2015, the disclosures of which are incorporated herein by reference in their entirety.

FIELD OF THE INVENTION

The present invention relates to the field of pharmaceutical chemistry and pharmaceutical therapeutics, and particularly to a class of 5-aromatic alkynyl substituted benzamide compounds, a preparation method thereof, a pharmaceutical composition containing such compound, and use as a negative allosteric modulator of metabotropic glutamate receptor subtype 5 (MGluR5), in particular use in the preparation of a medicament for the treatment of central nervous system and psychiatric-related diseases such as fragile X chromosome syndrome, Parkinson's disease levodopa-induced dyskinesia (PD-LID), gastroesophageal reflux disease (GERD), autism, pain, anxiety, depression, drug addiction and the like.

BACKGROUND OF THE INVENTION

Glutamate which is the most important excitatory neurotransmitter in the central nervous system of mammals plays an important role in maintaining the normal function of nervous system and also plays an important role in many pathophysiological processes such as pain, neurodegenerative lesions and epilepsy. At the same time, the massive release and accumulation of glutamate in the nervous system is the pathology basis of a variety of nerve cell damage and neurodegenerative disease, i.e., the neurotoxic effect of glutamate, eventually leading to neuronal death. The excitotoxicity lead by glutamate activating its receptor and the oxidative toxicity lead by inhibiting of glutamate/cystine transporters on the cell membrane are the origins of many nervous system diseases such as cerebral ischemia, Parkinson's disease, epilepsy, thus making glutamate receptors become one of the therapeutic targets of these diseases.

Glutamate receptors (GluR) are mainly divided into ionotropic glutamate receptors (iGluRs) and metabotropic glutamate receptors (mGluRs). The ionotropic glutamate receptor antagonist has achieved some therapeutic effect in the animal model by directly blocking the postsynaptic effect of glutamate, but it also blocks normal excitatory transmission and produces serious side effects, such as psychiatric symptoms, dizziness, fatigue, etc., thus limiting the clinical application of such compounds; and metabotropic glutamate receptors inhibit the release of glutamate through the presynaptic mechanism, thus reducing the toxic and side effect of ionotropic glutamate receptor antagonist, and are expected to become a new target for the treatment of certain neurological diseases.

mGluRs is one of the members of the C family of the G protein coupled receptors (GPCRs) superfamily. According to its protein sequence homology, receptor-coupled second messenger system signal transduction mechanism and specificity for different agonists, it can be divided into three categories. The first category mGluRI (mGluR1, mGluR5) mainly is distributed in the postsynaptic region, the mGluR1 receptors are also distributed in the glial cells, and the mGluR5 receptors are distributed in the marginal cortex and basal ganglia, which are closely related to the morphology of dendritic spines and play an important role in synaptic transmission and plasticity. The second category mGluR II (mGluR2, mGluR3) mainly locates in the presynaptic region, wherein mGluR2 receptors locate in the cerebellum, cerebral cortex, thalamus synaptic axons, mGluR3 receptors are also widely distributed in the brain, including glia. The third category mGluRIII (mGluR4, mGluR6, mGluR7, mGluR8) is also distributed in the presynaptic region, mGluR 4/7/8 locates in the basal ganglia movement loop, and mGluR6 receptors are in the retinal neurons. There is about 70% homology in the same mGluR group, and only about 45% homology between the different groups. mGluR5 mainly locates in the neuronal postsynaptic excitatory terminal and glia, couples with Gα/q protein, activates phospholipase C, and enhances intracellular $Ca^{2+}$ release. Studies have shown that mGluR5 is highly expressed in the central nervous system (CNS), mainly in the areas associated with the nervous system and mental illness such as cerebral cortex, hippocampus and basal ganglia, etc. Thus, mGluR5 is one of the important targets for the treatment of central nervous system and psychiatric-related diseases.

Regarding to the design of medicine to the target, early studies mainly focused on the design of small molecule competitive antagonists for endogenous ligands, but because of the high conservation degree of the mGlu receptor binding sites, it is difficult to obtain a compound having good selectivity to receptor subtypes. In addition, many endogenous ligands are often glutamic acid derivatives, lacking suitable pharmacokinetic properties and CNS permeability makes these compounds difficult to use in clinical research. In recent years, allosteric modulators of mGlu receptors have attracted widespread attention. Compounds bind to non-endogenous ligand sites, do not directly activate or antagonize receptor function, but indirectly increase or decrease glutamate-induced activity, known as positive allosteric modulators (PAMs) and negative allosteric modulators (NAMs). mGlu receptor allosteric modulators act on the allosteric sites of the GPCR transmembrane region, thus providing greater possibilities for overcoming defects in the selectivity and poor permeability of the mGlu receptor endogenous site competitive antagonists.

In recent years, mGluR5 negative allosteric modulator has caused great concern of the majority of scientific research workers and major pharmaceutical companies as a potential treatment drug for fragile X chromosome syndrome, such as Parkinson's disease levodopa-induced dyskinesia (PD-LID), gastroesophageal reflux disease (GERD), autism, pain, anxiety, depression, drug addiction and the like. Since 2000, there have been more than 190 mGluR5 negative allosteric modulator patent applications, of which 66 patent applications are filed from 2009 to June 2013; so far at least 9 small molecules have entered the clinical trials, of which 4 compounds are currently undergoing II or III clinical trials such as Mavoglurant, Diproglurant, RG7090 and Fenobam. Therefore, mGluR5 negative allosteric regulatory site is regarded as ideal drug target, while designing novel mGluR5 negative allosteric modulator for the treatment of the central nervous system and psychiatric system-related diseases on this basis has very important significance and good application prospects.

In summary, there is an urgent need in the art for the development of novel mGluR5 negative allosteric modulator.

SUMMARY OF THE INVENTION

The object of the present invention is to provide novel mGluR5 negative allosteric modulator, in particular mGluR5 negative allosteric modulators having improved selectivity.

The first aspect of the present invention provides a 5-aromatic alkynyl-substituted benzamide compound having a structure represented by the following general formula I, and racemate, R-isomer, S-isomer, pharmaceutically acceptable salt, or mixture thereof:

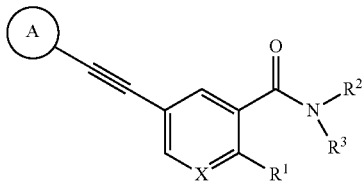

Formula I

X is CH or N;

$R^1$ is selected from the following group: hydrogen, halogen, C1-C6 alkyl, halogen substituted C1-C6 alkyl, cyano;

$R^2$ and $R^3$ are each independently selected from the group consisting of hydrogen, substituted or unsubstituted phenyl, substituted or unsubstituted 3-7 membered heteroaryl, substituted or unsubstituted 5-7 membered aryl-methylene, 3-7 membered heterocyclyl-methylene, each heterocyclyl independently contains 1 to 4 heteroatoms selected from oxygen, sulfur and nitrogen; and the $R^2$ and $R^3$ are not simultaneously hydrogen; or $R^2$ and $R^3$ together with the attached N atom form a group selected from the group consisting of substituted or unsubstituted 5-20 membered hetero spirocyclic ring, or substituted or unsubstituted 4-20 membered fused heterocyclic ring; wherein the substituted means one or more hydrogen atoms of the group are substituted by substituents selected from the group consisting of halogen, C1-C6 alkyl, halogen-substituted C1-C6 alkyl, C1-C6 alkoxy, C1-C6 alkoxycarbonyl, halogen-substituted C1-C6 alkoxy, C2-C6 alkenyl, C2-C6 alkynyl, C3-C8 cycloalkyl, cyano, nitro, amino, hydroxy, hydroxymethyl, carboxy, mercapto, sulfonyl, C6-C10 aryl, and 3-12 membered heterocyclyl; wherein the hetero spirocyclic ring, fused heterocyclic ring or heterocyclyl each independently contains 1 to 4 heteroatoms selected from oxygen, sulfur and nitrogen;

ring is selected from the group consisting of substituted or unsubstituted 5-6 membered aromatic heterocycle, substituted or unsubstituted 6-20 membered hetero aromatic fused ring, wherein the substituent is 1, 2, 3 or 4 substituents selected from the group consisting of halogen, C1-C6 alkyl, halogen-substituted C1-C6 alkyl, C1-C6 alkoxy, halogen-substituted C1-C6 alkoxy, C3-C8 cycloalkyl, C3-C8 halogenated cycloalkyl, cyano, nitro, amino (—$NH_2$), amino (preferably C1-C6 amino), hydroxy, hydroxymethyl, carboxy, mercapto, sulfonyl, C6-C10 aryl and 3-12 membered heterocyclyl, wherein the aromatic heterocycle, hetero aromatic fused ring or heterocyclyl each independently contains 1 to 4 heteroatoms selected from oxygen, sulfur and nitrogen;

and when $R^1$ is H,

ring is substituted or unsubstituted 5 membered aromatic heterocyclic ring;

the halogen is F, Cl, Br or I.

In another preferred embodiment, said $R^2$ and $R^3$ are each independently selected from the group consisting of hydrogen, substituted or unsubstituted phenyl, substituted or unsubstituted 3-7 membered heteroaryl, substituted or unsubstituted 5-7 membered aryl-methylene, 3-7 membered heterocyclyl-methylene, while each heterocyclyl independently contains 1 to 4 heteroatoms selected from oxygen, sulfur and nitrogen; $R^2$ and $R^3$ are not simultaneously hydrogen;

or $R^2$ and $R^3$ together with the attached N atom form a group selected from the group consisting of substituted or unsubstituted hetero spirocyclic ring, substituted or unsubstituted fused heterocyclic ring; wherein the substituted means one or more hydrogen atoms of the group are substituted by substituents selected from the group consisting of halogen, C1-C6 alkyl, C1-C6 alkoxy, halogen-substituted C1-C6 alkoxy, cyano, nitro, amino, hydroxy, hydroxymethyl, carboxy, mercapto, sulfonyl or trifluoromethyl.

In another preferred embodiment, the

ring is selected from the group consisting of

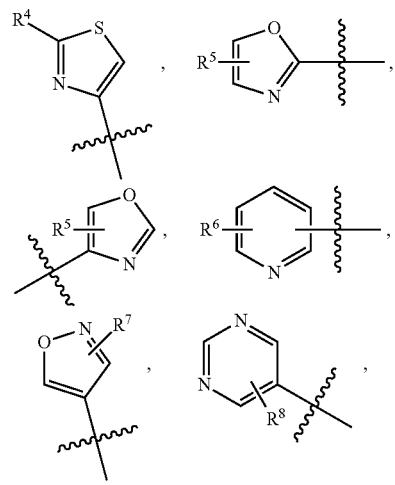

wherein $R^4$, $R^5$, $R^6$, $R^7$ and $R^8$ each represents 1-4 substituents on the heteroring, and each substituent is independently selected from the group consisting of halogen, C1-C6 alkyl, halogen-substituted C1-C6 alkyl, C1-C6 alkoxy, cyano, nitro, amino, hydroxy.

In another preferred embodiment, R² is selected from the group consisting of substituted or unsubstituted phenyl, substituted or unsubstituted pyridyl, substituted or unsubstituted pyrazinyl; wherein said substituted means the hydrogen atom(s) of the group is substituted by the substituent(s) selected from the group consisting of halogen, C1-C6 alkyl, halogen-substituted C1-C6 alkyl, C1-C6 alkoxy, cyano, nitro, amino, hydroxy;

R₃ is H;

or R² and R³ together with the connected N atom form substituted or unsubstituted group selected from the group consisting of

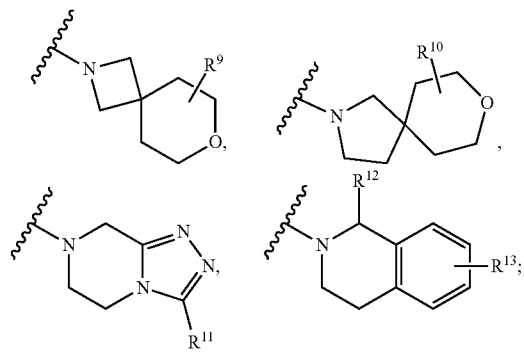

wherein R⁹, R¹⁰, R¹¹, R¹² and R¹³ each represent 1-4 substituents on any prosition of the ring, and each substituent is independently selected from the group consisting of halogen, C1-C6 alkyl, halogen-substituted C1-C6 alkyl, C1-C6 alkoxy, cyano, nitro, amino, hydroxy.

In another preferred embodiment,

Ⓐ is selected from the group consisting of substituted or unsubstituted pyridyl, substituted or unsubstituted thiazolyl, substituted or unsubstituted isoxazolyl, substituted or unsubstituted pyrimidinyl, or substituted or unsubstituted indazolyl; wherein the substitutent is selected from the group consisting of halogen, C1-C6 alkyl, halogen-substituted C1-C6 alkyl, C1-C6 alkoxy, cyano, nitro, amino, hydroxy.

In another preferred embodiment, R¹ is selected from H, F, Cl, CH₃, CN.

In another preferred embodiment, R² is selected from the group consisting of substituted or unsubstituted phenyl, substituted or unsubstituted pyridyl, or substituted or unsubstituted following groups:

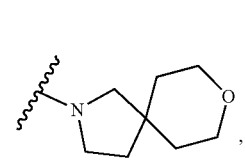

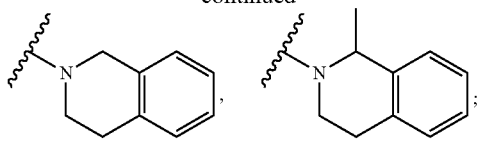

wherein said substituted means the hydrogen atom(s) of the group is substituted by the substituent(s) selected from the group consisting of halogen, C1-C6 alkyl, C1-C6 alkoxy, cyano.

In another preferred embodiment,

Ⓐ is selected from the group consisting of substituted or unsubstituted pyridyl, substituted or unsubstituted thiazolyl; wherein the substituent is defined as above.

In another preferred embodiment, the compound of formula I is a compound selected from the table A.

In the second aspect of the present invention, a pharmaceutical composition is provided, the pharmaceutical composition comprises: (a) a therapeutically effective amount of 5-aromatic alkynyl substituted benzamide compound of formula I, or a pharmaceutically acceptable salt, racemate, R-isomer, S-isomer thereof, or the combination thereof; and (ii) a pharmaceutically acceptable carrier.

In another preferred embodiment, the pharmaceutical composition is used in the treatment of diseases associated with the central nervous system and psychiatric system, preferably for the treatment of diseases selected from the group consisting of fragile X chromosome syndrome, Parkinson's disease levodopa-induced dyskinesia (PD-LID), gastroesophageal reflux disease (GERD), autism, pain, anxiety, depression, drug addiction, anxiety.

In another preferred embodiment, the pharmaceutical composition is an injection preparation.

In another preferred embodiment, the pharmaceutical composition is oral dosage preparation.

The third aspect of the present invention provides a mGluR5 negative allosteric modulator comprising a component selected from 5-aromatic alkynyl substituted benzamide compound of above general formula I, pharmaceutically acceptable salt thereof, racemate, R-isomer, S-isomer, or combination thereof.

In another preferred embodiment, the mGluR5 negative allosteric modulator selectively inhibits mGluR5.

In another preferred embodiment, the mGluR5 negative allosteric modulator has no inhibitory effect on mGluR1 (preferably, the ratio between the IC₅₀ value for mGluR5 to the IC₅₀ value for mGluR1 is ≥1000, preferably ≥2000; more preferably ≥5000, most preferably ≥10000).

In the fourth aspect of the present invention, use of the compound of formula I, or pharmaceutically acceptable salt, racemate, R-isomer, S-isomer thereof, or mixture thereof as described in the first aspect of the invention for preparing medicine for the treatment of disease associated with mGluR5 (metabotropic glutamate receptor subtype 5) is provided.

In another preferred embodiment, the disease is a disease associated with the central nervous system and psychiatric system, preferably for the treatment of disease selected from the group consisting of fragile X chromosome syndrome, Parkinson's disease levodopa-induced dyskinesia (PD-LID), gastroesophageal reflux disease (GERD), autism, pain, anxiety, depression, drug addiction, anxiety.

It should be understood that, in the present invention, each of the technical features specifically described above and below (such as those in the Examples) can be combined with each other, thereby constituting new or preferred technical solutions which need not be described one by one due to space limitation.

EMBODIMENTS FOR CARRYING OUT THE INVENTION

Figure 1:
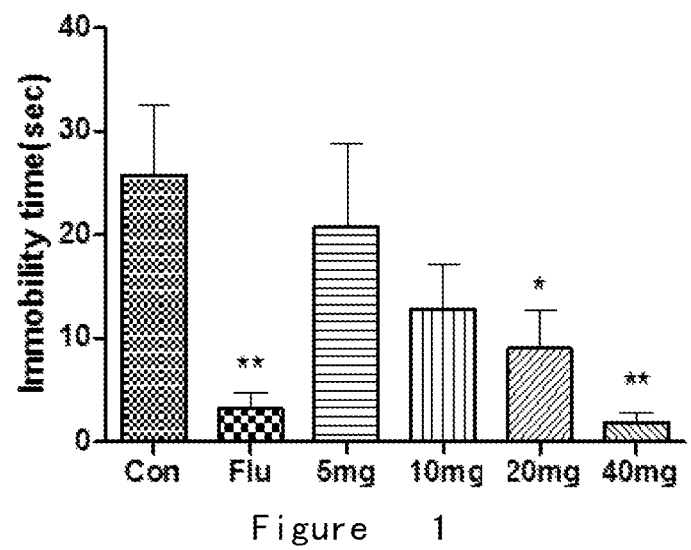
FIG. 1 shows the result of mouse tail suspension test of Example 7.

Through long-term and intensive study, the applicant has provided a mGluR5 negative allosteric modulator as shown in Formula I. The modulator can inhibit mGluR5 with high selectivity without showing inhibitory effect on other homologous metabolites glutamate receptors, or showing weak inhibitory effect, thus can be used for the preparation of medicine for treatment of mGluR5-related diseases, such as the central nervous system and psychiatric system-related diseases. The present invention is completed on this basis.

Terms

As used herein, the halogen is F, Cl, Br or I.

As used herein, the term "C1-C6 alkyl" refers to a straight or branched alkyl with 1 to 6 carbon atoms including, but not limited to methyl, ethyl, propyl, isopropyl, butyl, isobutyl, sec-butyl, tert-butyl, pentyl and hexyl, or the like.

As used herein, the term "C1-C6 alkoxy" refers to a straight or branched alkoxy having 1 to 6 carbon atoms including, but not limited to methoxy, ethoxy, propoxy, isopropoxy, butoxy, or the like.

As used herein, the term "C2-C6 alkenyl" refers to a straight or branched alkenyl containing one double bond having 2-6 carbon atoms including, but not limited to vinyl, propenyl, butenyl, isobutenyl, pentenyl and hexenyl.

As used herein, the term "C2-C6 alkynyl" refers to a straight or branched alkynyl containing one triple bond having from 2 to 6 carbon atoms, including, but not limited to ethynyl, propynyl, butynyl, isobutynyl, pentynyl, hexynyl and the like.

As used herein, the term "C3-C10 cycloalkyl" refers to a cyclic alkyl having 3 to 10 carbon atoms on the ring including, but not limited to cyclopropyl, cyclobutyl, cyclopentyl, cyclohexyl, cycloheptyl, cyclooctyl and cyclodecyl. The terms "C3-C8 cycloalkyl", "C3-C7 cycloalkyl" and "C3-C6 cycloalkyl" have similar meanings.

As used herein, the term "C6-C12 aryl" refers to an aryl group having 6 to 12 carbon atoms which does not comprise heteroatoms on the ring, such as phenyl, naphthyl and the like. The term "C6-C10 aryl" has a similar meaning.

As used herein, the term "3-12 membered heterocyclyl" refers to a saturated or unsaturated 3-12 membered ring group having 1 to 3 heteroatoms selected from oxygen, sulfur and nitrogen on the ring, such as dioxolanyl. The term "3-7 membered heterocyclyl" has a similar meaning.

The term "5-20 membered hetero spirocyclic ring" refers to a saturated or unsaturated spiro ring having 1 to 4 heteroatoms selected from N, O or S.

The term "4-20 membered fused heterocyclic ring" refers to a saturated, unsaturated or aromatic fused ring having 1-4 heteroatoms selected from N, O or S.

In the present invention, unless otherwise specified, the terms used have the general meaning known by those skilled in the art.

mGluR5 Negative Allosteric Modulator Related Diseases

Fragile X syndrome (FXS), also known as Martin-Bell syndrome, is a common hereditary mental retardation disease. The incidence is about 1/1250 in male and 1/2500 in female. It accounts for 2%-6% of non-specific mental retardation, and 40% of X-associated mental retardation. The clinical symptoms are various degrees of mental retardation, attention deficit, hyperactivity, anxiety with mood swings, obsessive-compulsive disorder, autism, and can also occur poor coordination of exercise and increased prevalence of epilepsy, as well as other non-neurological symptoms such as unusual face, large ears, excessive joint extension and postpubescent hyperorchidism. The virulence gene-FMR1 was successfully cloned by Verkerk, et al. (1991). The abnormal amplification of (CGG)n trinucleotide repeat sequence at the 5' end of the gene and the abnormal methylation of adjacent site CpG island lead to the transcription and translation termination of FMR1 gene, resulting in the reduction or deletion of the encoded product FMRP, i.e. fragile X mental retardation protein. The emergence of FMR1 knockout mice in 1994 was a milestone in the study of fragile X syndrome. Bakker et al. inserted a neomycin fragment in the FMR1 gene region, thus preventing the gene to express FMRP to produce a mouse model of fragile X syndrome. Many behavioral manifestations of FMR1 knockout mice are very similar to those of fragile X syndrome patients, most notably including the increase in spontaneous activity, the decreased open field habit ability, the increase of susceptibility of the audiogenic seizures, and the slight lack of learning ability.

For the fragile X chromosome syndrome, there are currently no approved drugs for the treatment of fragile X chromosome syndrome, while the existing treatment such as special education, behavioral therapy, social skills training and drug treatment can improve the prognosis of some affected individuals, and improve the secondary symptoms, but can not effectively solve the core defects of fragile X chromosome syndrome. Currently, commonly used drugs are mainly large doses of folic acid (which can improve patient's behavior and exercise ability, language quality, but can not improve intelligence obviously, and has no effect for adult patients), antidepressants, central nervous system stimulants (methylphenidate, dextroamphetamine, etc., which is effective for improving the lack of attention and excessive activity, but of great side effects) and anti-manic drugs (thioridazine, for the treatment of behavioral and emotional disorders).

Fragile X syndrome is caused by the mutation of a single gene FMR1. The FMR1 gene mutation will hinder the expression of protein FMRP, thus leading to the brain FMRP deletion. In normal circumstances, FMRP protein can control or block the mGluR5 activated signaling pathway in brain cells. When FMRP is absent, mGluR5 signal is overactivated, thus causing abnormalities in brain neurons relation and behavior and cognitive impairment associated with fragile X syndrome. The abnormalities of dendritic spine induced by fragile X syndrome may be due to the overactivation of mGluR-I pathway induced by FMRP deletion, which affects intracellular Ca2+ mobilization and protein synthesis. In the experiment, it was observed that when the FMR1 gene knockout mice cultured hippocampal neurons were given mGluRI inhibitor PHCCC, the content of microtubule-associated protein 1B (MAP1B) was significantly lower than that of untreated KO mice, thus confirming that the inhibitor could interfere with mGluR-I activation induced protein synthesis. It was also observed that the dendritic spine in the KO mouse inhibitory group was shorter than that in the untreated group, indicating that the inhibitor could partially reverse the dendritic spine morphological abnormality of the fragile X syndrome. This indicated that the mGluR-I inhibitor was able to partially replace the FMRP negative regulation function, thus affecting the function of these proteins. A number of studies have also shown that by specifically inhibiting mGluR5, the symptoms of FXS patients can be significantly improved, thus of good safety and less side effects. Therefore, mGluR5 negative allosteric regulatory site is regarded as ideal drug target for fragile X chromosome, while designing novel mGluR5 negative allosteric modulator for the treatment of such diseases on this basis has very important significance and good application prospects.

Gastroesophageal reflux disease (GERD) refers to a disease that discomfort and/or complications are caused by reflux of gastric contents. In addition to erosive esophagitis, Barrett's esophagus and esophageal adenocarcinoma, it also causes chronic cough, chronic laryngitis, bronchial asthma, tooth erosion and other extraesophageal manifestations. Beijing and Shanghai epidemiological survey showed that the prevalence of GERD was as high as 5.77%, which seriously affected the patients' daily work and life quality. With the change of life style and diet, the incidence of GERD in our country is increasing year by year.

At present, the main drug for clinical treatment of GERD is proton pump inhibitor (PPI), but there are PPI-resistant patients whose symptoms are not necessarily related to acid. Also, it often leads to recurrence of patients after drug discontinuance, and long-term use also leads to patients adverse reactions. And most of other drugs such as H2 receptor inhibitors, prokinetic agent, visceral pain regulators, antacids, etc. are only effective to mild patients, which limits its clinical application. The traditional treatment drugs can only relieve symptoms to a certain extent, and can not achieve the therapeutic effect for the pathogenesis.

Transient lower esophageal sphincter relaxation (TLESR) abnormality is one of the main pathogenesis of GERD. Studies have shown that about 90% of reflux in GERD patients is associated with TLESR. Glutamate can convey the sensory information in the intestine to the central nervous system, including the vagal signal that triggers TLESR. Studies have shown that selective mGluR5 negative allosteric modulators can effectively inhibit TLESR, reduce the number of patients reflux, and extend the interval of reflux. Other studies have shown that mGluR5 negative allosteric modulators can reduce colorectal pain sensibility. And visceral hyperalgesia plays a role in functional heartburn and PPI resistance GERD, indicating that it have a certain effect on GERD, especially PPI resistance GERD.

Although mGluR5 negative allosteric modulator is promising as anti-reflux drug for the treatment of GERD, but the drugs in the clinical are limited in efficacy, and there are some adverse reactions. Therefore, safe, effective and highly selective mGluR5 negative allosteric modulators need to be developed.

Parkinson's disease (PD), also known as tremor paralysis, is the second major central nervous system degenerative diseases after Alzheimer's disease, the main clinical symptoms are exercise retardation, resting tremor, muscle stiffness, gait and posture abnormalities. The widespread use of levodopa has resulted in a more satisfactory control of Parkinson's symptoms, but most patients experience levodopa-induced dyskinesia (LID) after long-term use (more than five years). LID are often expressed as dance-like movements, dystonia, athetosis, or simple repetitive involuntary movements, the severity often associated with the degree of degenerative lesions of dopaminergic neurons.

In PD, since the inhibitory effect of D2 receptor on the striatum-globus pallidus neurons is attenuated, and the glutamate conduction activity of the indirect pathway is significantly enhanced, therefore, reducing the activity of the indirect pathway is the main goal of PD treatment, which can be achieved by inhibition of glutamate neurotransmission. Blocking glutamate receptor activity by the drug can reduce the introduction of glutamatergic neurons, block intrastriatal gene abnormal expression caused by levodopa, and weaken the LID. mGluR5 is highly expressed on the projection neurons of the striatum, but not in the target organ of the autonomic nervous system, which overcomes the adverse effects of the traditional drugs acting directly on the dopamine system. Studies have also shown that mGluR5 negative allosteric modulators can reduce the probability of LID in PD rats; and clinical drugs have also showed that mGluR5 negative allosteric modulators have good safety, tolerance and anti-exercise disorder effectivity.

Compound of Formula I

The present invention provides a 5-aromatic alkynyl-substituted benzamide compound having a structure represented by the following general formula I, and racemate, R-isomer, S-isomer, pharmaceutically acceptable salt, or the mixture thereof:

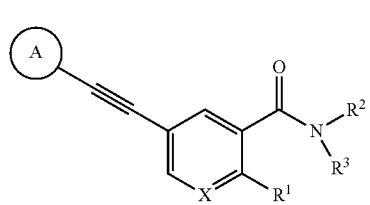

Formula I wherein:

X is CH or N;

$R^1$ is selected from the following group: hydrogen, halogen, C1-C6 alkyl, halogen substituted C1-C6 alkyl, cyano;

$R^2$ and $R^3$ are each independently selected from the group consisting of hydrogen, substituted or unsubstituted phenyl, substituted or unsubstituted 3-7 membered heteroaryl, substituted or unsubstituted 5-7 membered aryl-methylene, 3-7 membered heterocyclyl-methylene, each heterocyclyl independently contains 1 to 4 heteroatoms selected from oxygen, sulfur and nitrogen; and $R^2$ and $R^3$ are not simultaneously hydrogen; or $R^2$ and $R^3$ together with the attached N atom form a group selected from the group consisting of substituted or unsubstituted 5-20 membered hetero spirocyclic ring, or substituted or unsubstituted 4-20 membered fused heterocyclic ring; wherein the substituted means one or more hydrogen atoms of the group are substituted by substituents selected from the group consisting of halogen, C1-C6 alkyl, halogen-substituted C1-C6 alkyl, C1-C6 alkoxy, C1-C6 alkoxycarbonyl, halogen-substituted C1-C6 alkoxy, C2-C6 alkenyl, C2-C6 alkynyl, C3-C8 cycloalkyl, cyano, nitro, amino, hydroxy, hydroxymethyl, carboxy, mercapto, sulfonyl, C6-C10 aryl, and 3-12 membered heterocyclyl; wherein the hetero spirocyclic ring, fused heterocyclic ring or heterocyclyl each independently contains 1 to 4 heteroatoms selected from oxygen, sulfur and nitrogen;

(A)

ring is selected from the group consisting of substituted or unsubstituted 5-6 membered aromatic heterocycle, substituted or unsubstituted 6-20 membered hetero aromatic fused ring, wherein the substituent is 1, 2, 3 or 4 substituents selected from the group consisting of halogen, C1-C6 alkyl, halogen-substituted C1-C6 alkyl, C1-C6 alkoxy, halogen-substituted C1-C6 alkoxy, C3-C8 cycloalkyl, C3-C8 halogenated cycloalkyl, cyano, nitro, amino, amino (preferably C1-C6 amino), hydroxy, hydroxymethyl, carboxy, mercapto, sulfonyl, C6-C10 aryl and 3-12 membered heterocyclyl, wherein the aromatic heterocycle, hetero aromatic fused ring or heterocyclyl each independently contains 1 to 4 heteroatoms selected from oxygen, sulfur and nitrogen;
and when $R^1$ is H, (A)

ring is substituted or unsubstituted 5 membered aromatic heterocycle;
the halogen is F, Cl, Br or I.
In another preferred embodiment, said $R^2$ and $R^3$ are each independently selected from the group consisting of hydrogen, substituted or unsubstituted phenyl, substituted or unsubstituted 3-7 membered heteroaryl, substituted or unsubstituted 5-7 membered aryl-methylene, 3-7 membered heterocyclyl-methylene, while each heterocyclyl independently contains 1 to 4 heteroatoms selected from oxygen, sulfur and nitrogen; $R^2$ and $R^3$ are not simultaneously hydrogen;
or R2 and R3 together with the attached N atom form a group selected from the group consisting of substituted or unsubstituted hetero spirocyclic ring, substituted or unsubstituted fused heterocyclic ring; wherein the substituted means one or more hydrogen atoms of the group are substituted by substituents selected from the group consisting of halogen, C1-C6 alkyl, C1-C6 alkoxy, halogen-substituted C1-C6 alkoxy, cyano, nitro, amino, hydroxy, hydroxymethyl, carboxy, mercapto, sulfonyl, or trifluoromethyl.
In another preferred embodiment, (A)

ring is selected from the group consisting of

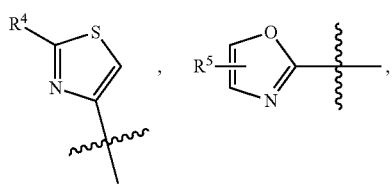

-continued

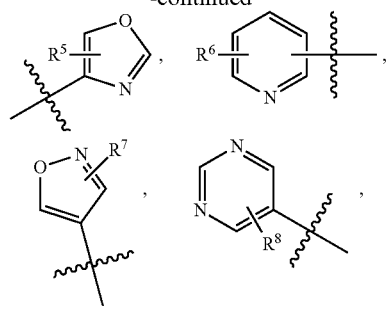

wherein $R^4$, $R^5$, $R^6$, $R^7$ and $R^8$ each represents 1-4 substituents on the heteroring, and each substituent is independently selected from the group consisting of halogen, C1-C6 alkyl, halogen-substituted C1-C6 alkyl, C1-C6 alkoxy, cyano, nitro, amino, hydroxy.
In another preferred embodiment, $R^2$ is selected from the group consisting of substituted or unsubstituted phenyl, substituted or unsubstituted pyridyl, substituted or unsubstituted pyrazinyl; wherein said substituted means the hydrogen atom(s) of the group is substituted by the substituent(s) selected from the group consisting of halogen, C1-C6 alkyl, halogen-substituted C1-C6 alkyl, C1-C6 alkoxy, cyano, nitro, amino, hydroxy;
$R_3$ is H;
or $R^2$ and $R^3$ together with the connected N atom form substituted or unsubstituted group selected from the group consisting of

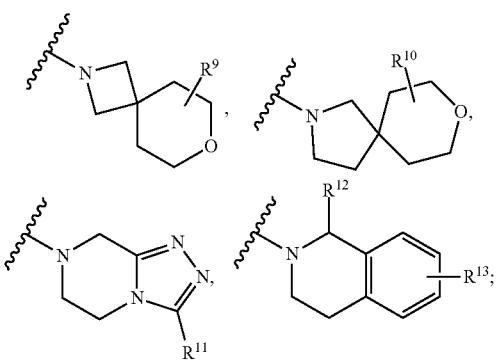

wherein $R^9$, $R^{10}$, $R^{11}$, $R^{12}$ and $R^{13}$ each represents 1-4 substituents on any prosition of the ring, and each substituent is independently selected from the group consisting of halogen, C1-C6 alkyl, halogen-substituted C1-C6 alkyl, C1-C6 alkoxy, cyano, nitro, amino, hydroxy.
In another preferred embodiment, (A)

is selected from the group consisting of substituted or unsubstituted pyridyl, substituted or unsubstituted thiazolyl, substituted or unsubstituted isoxazolyl, substituted or unsubstituted pyrimidinyl, or substituted or unsubstituted indazolyl; wherein the substitutent is selected from the group consisting of halogen, C1-C6 alkyl, halogen-substituted C1-C6 alkyl, C1-C6 alkoxy, cyano, nitro, amino, hydroxy.

In another preferred embodiment, $R^1$ is selected from H, F, Cl, $CH_3$, CN.

In another preferred embodiment, $R^2$ is selected from the group consisting of substituted or unsubstituted phenyl, substituted or unsubstituted pyridyl, or substituted or unsubstituted following groups:

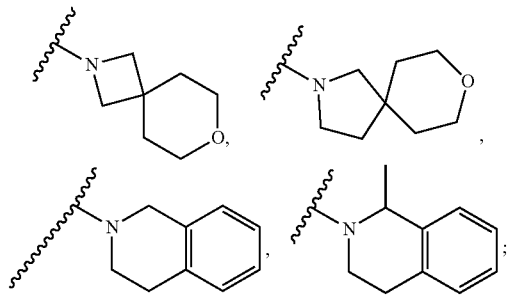

wherein said substituted means the hydrogen atom(s) of the group is substituted by the substituent(s) selected from the group consisting of halogen, C1-C6 alkyl, 1-C6 alkoxy, cyano.

In another preferred embodiment,

is selected from the group consisting of substituted or unsubstituted pyridyl, substituted or unsubstituted thiazolyl; wherein the substituent is defined as above.

In a more preferred embodiment of the present invention, the compounds of general formula I of the present invention are preferably specific compounds as follows:

TABLE A

| No. | Name | Structure |
|---|---|---|
| ZD001 | 2-fluoro-5-(pyridin-2-ethynyl)-N-(4-fluorophenyl)benzamide | 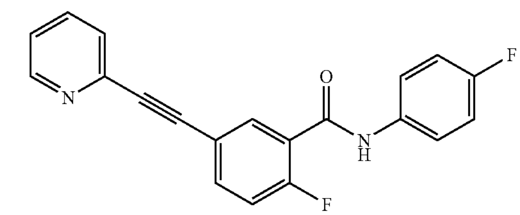 |
| ZD002 | (2-chloro-5-(pyridin-2-ethynyl)phenyl)(7-oxa-2-aza-spiro[3.5]nonan-2-yl)methanone | 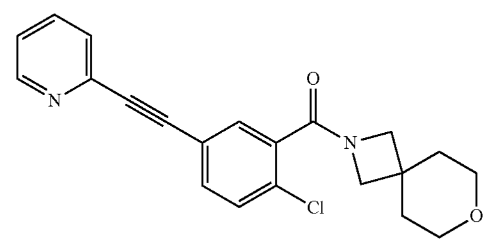 [SMILES: O=C(c1cc(C#Cc2ccccn2)ccc1Cl)N1CC2(CCOCC2)C1] |
| ZD003 | (2-chloro-5-(pyridin-2-ethynyl)phenyl)(8-oxa-2-aza-spiro[4.5]dec-2-yl)methanone | 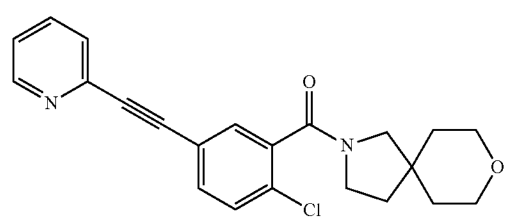 [SMILES: O=C(c1cc(C#Cc2ccccn2)ccc1Cl)N1CCC2(CCOCC2)C1] |
| ZD004 | 2-fluoro-N-(4-fluorophenyl)-5-((2-methyl-thiZaol-4-yl)ethynyl)benzamide | 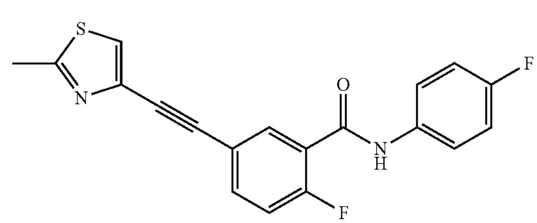 [SMILES: Cc1nc(C#Cc2ccc(F)c(C(=O)Nc3ccc(F)cc3)c2)cs1] |

TABLE A-continued

| No. | Name | Structure |
|---|---|---|
| ZD005 | (3-((2-methylthiazol-4-yl)ethynyl)phenyl)(3-trifluoromethyl-5,6-dihydro-[1,2,4]triazolo[4,3-a]pyrazin-7(8H)-yl)methanone | 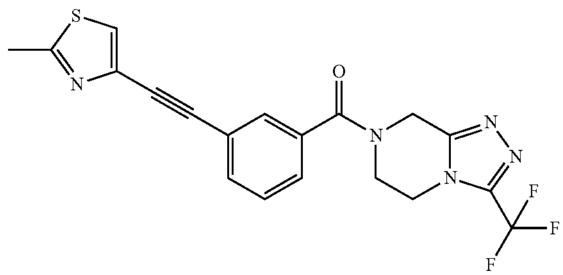 [SMILES: Cc1nc(C#Cc2cccc(C(=O)N3CCn4c(nnc4C(F)(F)F)C3)c2)cs1] |
| ZD006 | 5-((1H-indazol-5-yl)ethynyl)-2-fluoro-N-(4-fluorophenyl)benzamide | 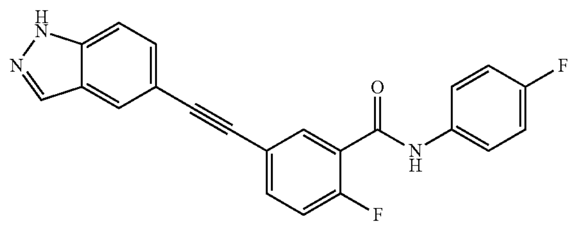 [SMILES: O=C(Nc1ccc(F)cc1)c1cc(C#Cc2ccc3[nH]ncc3c2)ccc1F] |
| ZD007 | (3-((2-methylthiazol-4-yl)phenyl)(7-oxa-2-aza-spiro[3.5]nonan-2-yl)methanone | 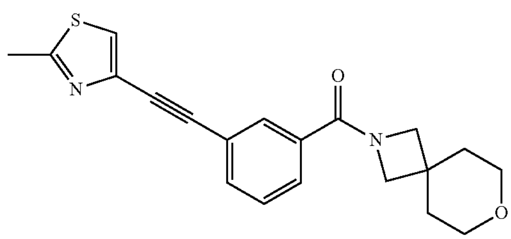 [SMILES: Cc1nc(C#Cc2cccc(C(=O)N3CC4(CCOCC4)C3)c2)cs1] |
| ZD008 | (3-((2-methylthiazol-4-yl)phenyl)(8-oxa-2-aza-spiro[4.5]dec-2-yl)methanone | 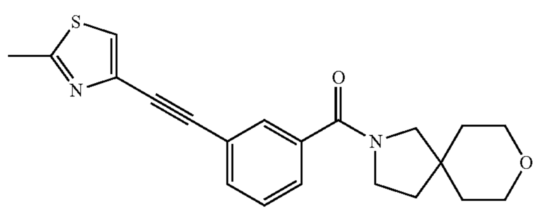 [SMILES: Cc1nc(C#Cc2cccc(C(=O)N3CCC4(CCOCC4)C3)c2)cs1] |
| ZD009 | N-(4-fluorophenyl)-3-((2-methylthiazol-4-yl)ethynyl)benzamide | 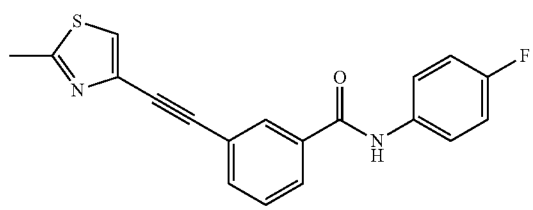 [SMILES: Cc1nc(C#Cc2cccc(C(=O)Nc3ccc(F)cc3)c2)cs1] |
| ZD010 | N-(4-cyanophenyl)-3-((2-methylthiazol-4-yl)ethynyl)benzamide | 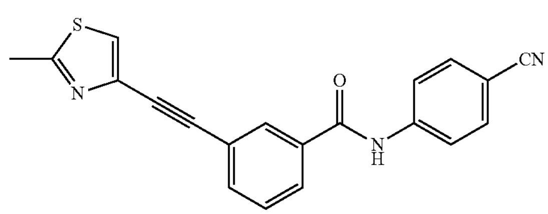 [SMILES: Cc1nc(C#Cc2cccc(C(=O)Nc3ccc(C#N)cc3)c2)cs1] |
| ZD011 | (1-methyl-3,4-dihydro-isoquinolin-2(1H)-yl-3-((2-methyl-thiazol-4-yl)ethynyl)phenyl)methanone | 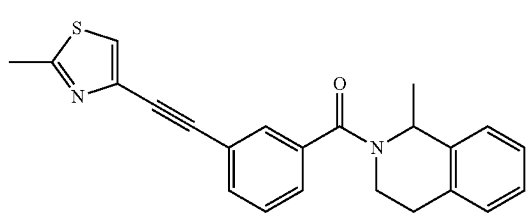 [SMILES: Cc1nc(C#Cc2cccc(C(=O)N3CCc4ccccc4C3C)c2)cs1] |

TABLE A-continued

| No. | Name | Structure |
|---|---|---|
| ZD012 | (3,4-dihydro-isoquinolin-2(1H)-yl)(3-((2-methyl-thiazol-4-yl)ethynyl)phenyl)methanone | 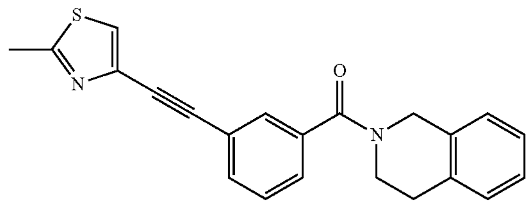 [SMILES: Cc1nc(C#Cc2cccc(C(=O)N3CCc4ccccc4C3)c2)cs1] |
| ZD013 | 3-((2-methylthiazol-4-ylethynyl)-N-(pyridin-3-yl)benzamide | 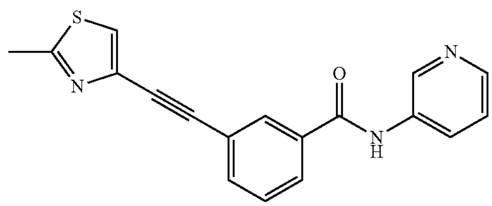 [SMILES: Cc1nc(C#Cc2cccc(C(=O)Nc3cccnc3)c2)cs1] |
| ZD014 | 3-((2-methylthiazol-4-ylethynyl)-N-phenylbenzamide | 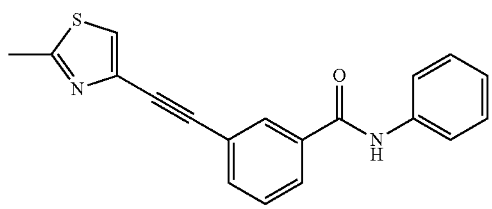 [SMILES: Cc1nc(C#Cc2cccc(C(=O)Nc3ccccc3)c2)cs1] |
| ZD015 | 3-((2-methylthiazol-4-ylethynyl)-N-(4-(trifluoromethyl)phenyl)benzamide | 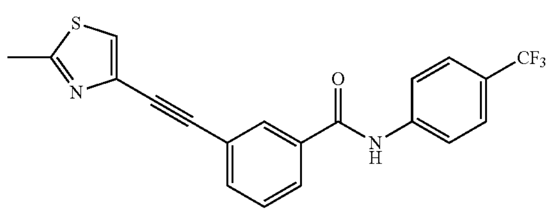 [SMILES: Cc1nc(C#Cc2cccc(C(=O)Nc3ccc(C(F)(F)F)cc3)c2)cs1] |
| ZD017 | N-(3-fluorophenyl)-3-((2-methylthiazol-4-yl)ethynyl)benzamide | 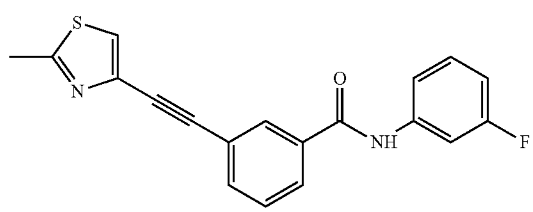 [SMILES: Cc1nc(C#Cc2cccc(C(=O)Nc3cccc(F)c3)c2)cs1] |
| ZD019 | N-(3-cyanophenyl)-3-((2-methylthiazol-4-yl)ethynyl)benzamide | 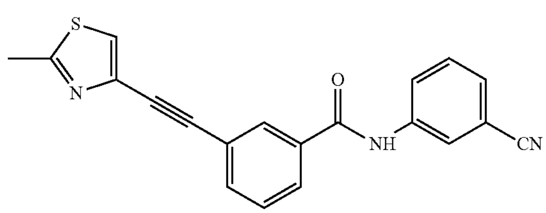 [SMILES: Cc1nc(C#Cc2cccc(C(=O)Nc3cccc(C#N)c3)c2)cs1] |
| ZD036 | 2-chloro-N-(4-fluorophenyl)-5-(pyridin-2-ethynyl)benzamide | 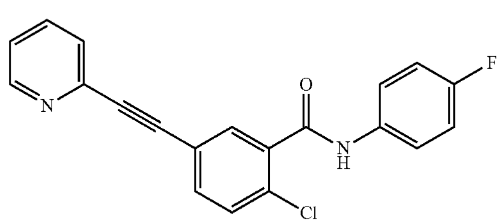 [SMILES: O=C(Nc1ccc(F)cc1)c1cc(C#Cc2ccccn2)ccc1Cl] |

TABLE A-continued

| No. | Name |
|---|---|
| ZD037 | 2-chloro-N-(4-fluorophenyl)-5-((2-methyl-thiazol-4-yl)ethynyl)benzamide |
| ZD038 | 2-fluoro-N-(4-fluorophenyl)-5-(pyridin-3-ethynyl)benzamide |
| ZD039 | 2-fluoro-N-(4-fluorophenyl)-5-(pyridin-4-ethynyl)benzamide |
| ZD040 | N-(4-fluorophenyl)-2-methyl-5-(pyridin-2-ethynyl)benzamide |
| ZD041 | N-(4-fluorophenyl)-2-methyl-5-((2-methyl-thiazol-4-yl)ethynyl)benzamide |
| ZD042 | 2-fluoro-5-(pyridin-2-ethynyl)-N-(pyridin-3-yl)benzamide |
| ZD043 | 2-fluoro-5-((2-methylthiazol-4-ylethynyl)-N-(pyridin-3-yl)benzamide |

TABLE A-continued

| No. | Name |
|---|---|
| ZD044 | N-(4-cyanophenyl)-2-fluoro-5-(pyridin-2-ethynyl)benzamide |
| ZD045 | N-(4-cyanophenyl)2-fluoro-5-((2-methyl-thiazol-4-yl)ethynyl)benzamide |
| ZD046 | (3,4-dihydro-isoquinolin-2(1H)-yl)(2-fluoro-5-(pyridin-2-ylethynyl)phenyl)methanone |
| ZD047 | (3,4-dihydro-isoquinolin-2(1H)-yl)(2-fluoro-5-((2-methyl-thiazol-4-yl)ethynyl)phenyl)methanone |
| ZD048 | (2-fluoro-5-(pyridin-2-ylethynyl)phenyl)(1-methyl-3,4-dihydro-isoquinolin-2(1H)-yl)methanone |
| ZD049 | (2-fluoro-5-((2-methyl-thiazol-4-yl)ethynyl)phenyl)(1-methyl-3,4-dihydro-isoquinolin-2(1H)-yl)methanone |
| ZD050 | 2-fluoro-5-((2-methylthiazol-4-ylethynyl)-N-(pyridin-3-yl)nicotinainide |

TABLE A-continued

| No. | Name |
|---|---|
| ZD051 | 2-fluoro-N-(4-fluorophenyl)-5-(pyridin-2-ylethynyl)nicotinamide |
| ZD052 | (3,4-dihydro-isoquinolin-2(1H)-yl)(2-fluoro-5-((2-methyl-thiazol-4-yl)ethynyl)pyridin-3-yl)methanone |
| ZD053 | 2-fluoro-N-(4-fluorophenyl)-5-((2-methyl-thiazol-4-yl)ethynyl)nicotinamide |
| ZD054 | 2-chloro-N-(4-fluorophenyl)-5-((2-methyl-thiazol-4-yl)ethynyl)nicotinamide |
| ZD055 | 2-fluoro-5-(pyridin-2-ylethynyl)-N-(pyridin-3-yl)nicotinamide |
| ZD056 | (3,4-dihydro-isoquinolin-2(1H)-yl)(2-fluoro-5-(pyridin-2-ylethynyl)pyridin-3-yl)methanone |
| ZD057 | 2-fluoro-5-((2-methylthiazol-4-yl)ethynyl)-N-benzoylaniline |

TABLE A-continued

| No. | Name | Structure |
|---|---|---|
| ZD058 | 2-cyano-5-((2-methylthiazol-4-ylethynyl)-N-(pyridin-3-yl)benzamide | 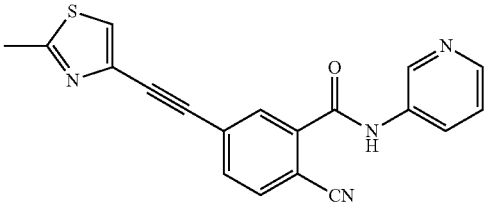 [SMILES: Cc1nc(C#Cc2ccc(C#N)c(C(=O)Nc3cccnc3)c2)cs1] |
| ZD059 | 5-((2-methylthiazol-4-ylethynyl)-N-(pyridin-3-yl)-2-(trifluoromethyl)benzamide | 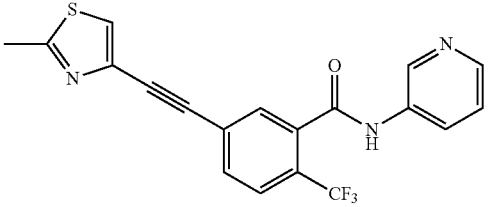 [SMILES: Cc1nc(C#Cc2ccc(C(F)(F)F)c(C(=O)Nc3cccnc3)c2)cs1] |
| ZD060 | N-(4-fluorophenyl)-5-((2-methylthiazol-4-yl)ethynyl)-2-(trifluoromethyl)benzamide | 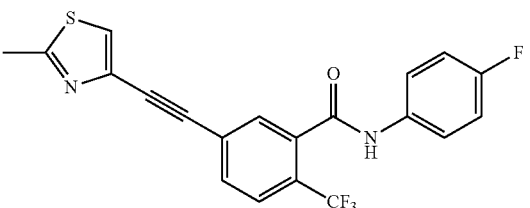 |
| ZD061 | 2-cyano-N-(4-fluorophenyl)-5-((2-methylthiazol-4-yl)ethynyl)benzamide | 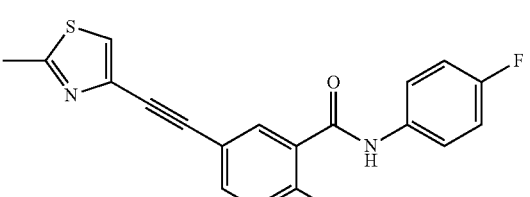 |
| ZD062 | 4-((2-methylthiazol-4-yl)ethynyl)-2-(1,2,3,4-dihydroisoquinolin-2-carbonyl)benzonitrile | 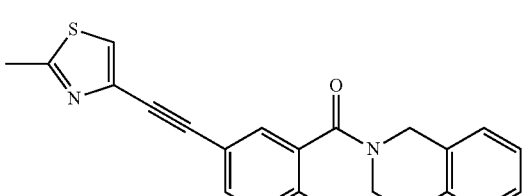 |
| ZD063 | (3,4-dihydro-isoquinolin-2(1H)-yl)(5-((2-methyl-thiazol-4-yl)ethynyl)-2-(trifluoromethyl)phenyl)methanone | 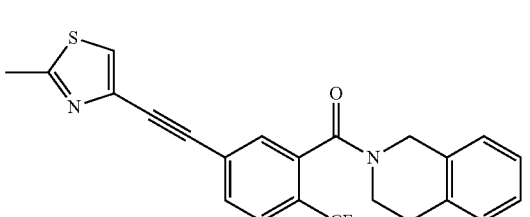 |
| ZD064 | 2-fluoro-N-(2-fluorophenyl)-5-((2-methylthiazol-4-yl)ethynyl)benzamide | 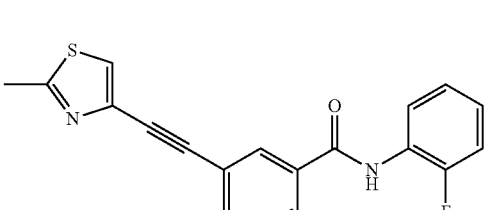 |

TABLE A-continued

| No. | Name | Structure |
|---|---|---|
| ZD065 | 2-fluoro-N-(3-fluorophenyl)-5-((2-methylthiazol-4-yl)ethynyl)benzamide | 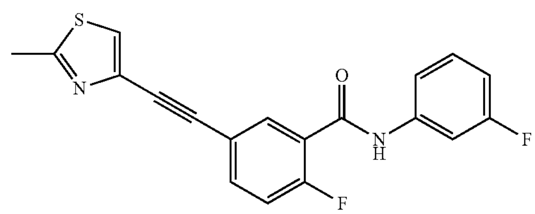 [SMILES: Cc1nc(C#Cc2ccc(F)c(C(=O)Nc3cccc(F)c3)c2)cs1] |
| ZD066 | N-(3,4-difluorophenyl)-2-fluoro-5-((2-methylthiazol-4-yl)ethynyl)benzamide | 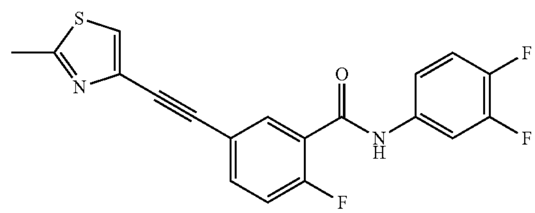 [SMILES: Cc1nc(C#Cc2ccc(F)c(C(=O)Nc3ccc(F)c(F)c3)c2)cs1] |
| ZD067 | N-(2,4-difluorophenyl)-2-fluoro-5-((2-methylthiazol-4-yl)ethynyl)benzamide | 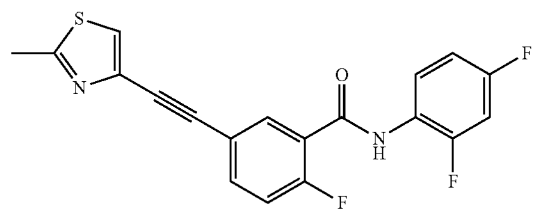 [SMILES: Cc1nc(C#Cc2ccc(F)c(C(=O)Nc3ccc(F)cc3F)c2)cs1] |
| ZD068 | N-(4-chlorophenyl)-2-fluoro-5-((2-methyl-thiazol-4-yl)ethynyl)benzamide | 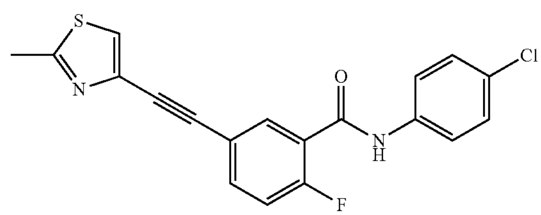 [SMILES: Cc1nc(C#Cc2ccc(F)c(C(=O)Nc3ccc(Cl)cc3)c2)cs1] |
| ZD069 | 2-fluoro-5-((2-methylthiazol-4-ylethynyl)-N-(4-(trifluoromethyl)phenyl)benzamide | 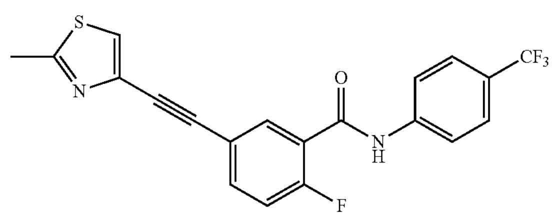 [SMILES: Cc1nc(C#Cc2ccc(F)c(C(=O)Nc3ccc(C(F)(F)F)cc3)c2)cs1] |
| ZD070 | 2-fluoro-N-(4-methoxyphenyl)-5-((2-methylthiazol-4-yl)ethynyl)benzamide | 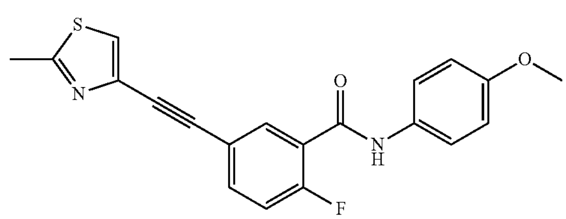 |
| ZD071 | 2-fluoro-5-((2-methylthiazol-4-ylethynyl)-N-(pyridin-2-yl)benzamide | 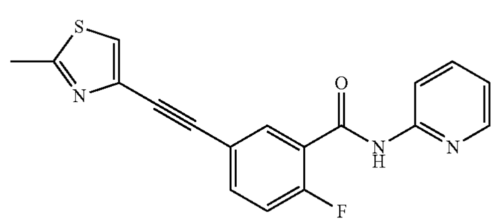 [SMILES: Cc1nc(C#Cc2ccc(F)c(C(=O)Nc3ccccn3)c2)cs1] |

TABLE A-continued

| No. | Name |
|---|---|
| ZD072 | 2-fluoro-5-((2-methylthiazol-4-ylethynyl)-N-(pyridin-4-yl)benzamide |
| ZD073 | 2-fluoro-N-(6-fluoropyridin-3-yl)-5-((2-methylthiazol-4-yl)ethynyl)benzamide |
| ZD074 | N-(6-chloropyridin-3-yl)-2-fluoro-5-((2-methylthiazol-4-yl)ethynyl)benzamide |
| ZD075 | 2-fluoro-5-((2-methylthiazol-4-ylethynyl)-N-(p-methylphenyl)benzamide |
| ZD076 | 2-fluoro-N-(pyridin-3-yl)-5-(thiazol-4-ylethynyl)benzamide |
| ZD077 | 2-fluoro-5-((2-fluorothiazol-4-yl)ethynyl)-N-(pyridin-3-yl)benzamide |
| ZD078 | 5-((2-chlorothiazol-4-ylethynyl)-2-fluoro-N-(pyridin-3-yl)benzamide |

TABLE A-continued

| No. | Name |
|---|---|
| ZD079 | 2-fluoro-N-(pyridin-3-yl)-5-((2-(trifluoromethyl)thiazol-4-yl)ethynyl)benzamide |
| ZD080 | 2-fluoro-5-((6-methylpyridin-2-yl)ethynyl)-N-(pyridin-3-yl)benzamide |
| ZD081 | 2-fluoro-5-((6-fluoropyridin-2-yl)ethynyl)-N-(pyridin-3-yl)benzamide |
| ZD082 | 5-((6-chloropyridin-2-yl)ethynyl)-2-fluoro-N-(pyridin-3-yl)benzamide |
| ZD083 | 2-fluoro-N-(pyridin-3-yl)-5-((6-(trifluoromethyl)pyridin-2-yl)ethynyl)benzamide |
| ZD084 | 5-((6-cyanopyridin-2-yl)ethynyl)-2-fluoro-N-(pyridin-3-yl)benzamide |
| ZD085 | 2-fluoro-N-(pyridin-3-yl)-5-(pyrimidin-5-ylethynyl)benzamide |

TABLE A-continued

| No. | Name | Structure |
|---|---|---|
| ZD086 | 2-fluoro-5-((2-methylpyrimidin-5-yl)ethynyl)-N-(pyridin-3-yl)benzamide | 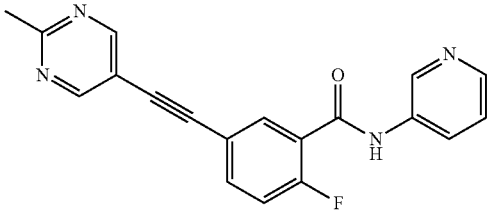 [SMILES: Cc1ncc(C#Cc2ccc(F)c(C(=O)Nc3cccnc3)c2)cn1] |
| ZD087 | 2-fluoro-N-(4-fluorophenyl)-5-((2-methylpyrimidin-5-yl)ethynyl)benzamide | 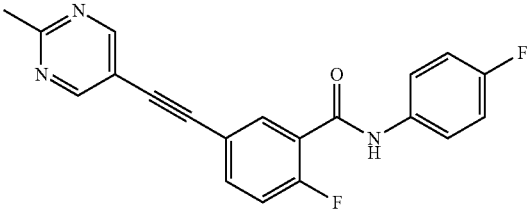 [SMILES: Cc1ncc(C#Cc2ccc(F)c(C(=O)Nc3ccc(F)cc3)c2)cn1] |
| ZD088 | (3,4-dihydro-isoquinolin-2(1H)-yl)(2-fluoro-5-((2-methylpyrimidin-5-yl)ethynyl)phenylmethanone | 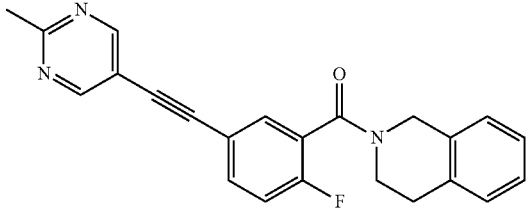 [SMILES: Cc1ncc(C#Cc2ccc(F)c(C(=O)N3CCc4ccccc4C3)c2)cn1] |
| ZD089 | 2-fluoro-5-((2-methyloxazol-4-ylethynyl)-N-(pyridin-3-yl)benzamide | 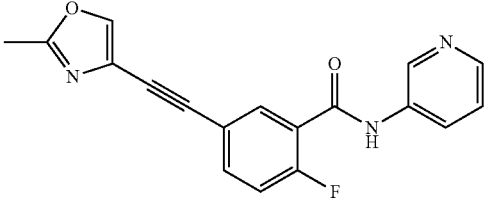 |
| ZD090 | 2-fluoro-N-(4-fluorophenyl)-5-((2-methyloxazol-4-yl)ethynyl)benzamide | 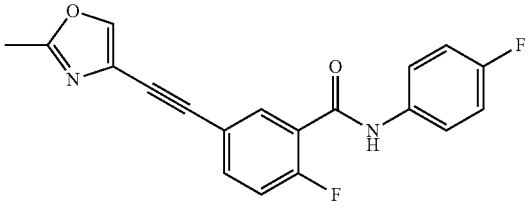 |
| ZD091 | (3,4-dihydro-isoquinolin-2(1H)-yl)(2-fluoro-5-((2-methyloxazol-4-yl)ethynyl)phenyl)methanone | 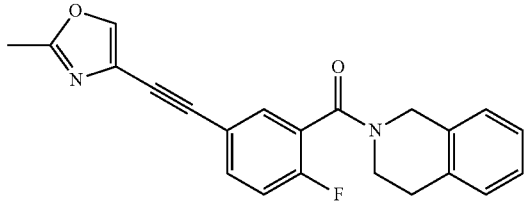 |
| ZD092 | (3,4-dihydro-isoquinolin-2(1H)-yl)(5-((3-5-dimethylisoxazol-4-yl)ethynyl)-2-fluorophenyl)methanone | 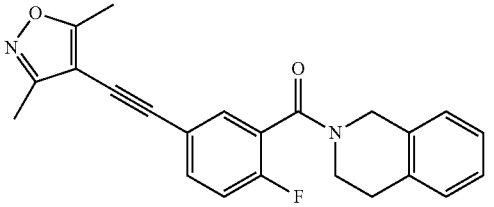 [SMILES: Cc1noc(C)c1C#Cc1ccc(F)c(C(=O)N2CCc3ccccc3C2)c1] |

TABLE A-continued

| No. | Name | Structure |
|---|---|---|
| ZD093 | 5-((3,5-dimethylisoxazol-4-ylethynyl)-2-fluoro-N-(pyridin-3-yl)benzamide | 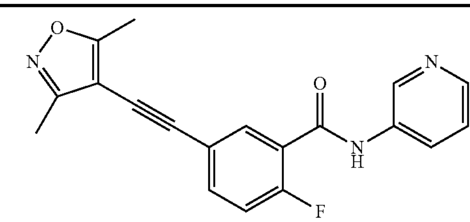 |
| ZD094 | 5-((3,5-dimethylisoxazol-4-ylethynyl)-2-fluoro-N-(4-fluorophenyl)benzamide | 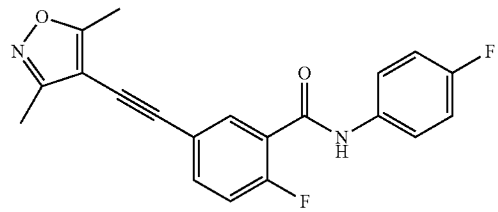 [SMILES: Cc1noc(C)c1C#Cc1ccc(F)c(C(=O)Nc2ccc(F)cc2)c1] |

Pharmaceutically Acceptable Salts

The present invention provides a pharmaceutically acceptable salt of the compound of formula I, in particular a conventional pharmaceutically acceptable salt formed by the reaction of the compound of formula I with an inorganic or organic acid. For example, the conventional pharmaceutically acceptable salt may be prepared by reacting the compound of formula I with an inorganic acid including hydrochloric acid, hydrobromic acid, sulfuric acid, nitric acid, aminosulfonic acid, phosphoric acid and the like, or an organic acid including citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid, isethionic acid etc.; or may be sodium, potassium salt, calcium salt, aluminum salt or ammonium salt formed by the compound of formula I with an inorganic base; or may be methanamine salt, ethylamine salt or ethanolamine salt formed by the compound of formula I with an organic base.

The Preparation Method of Compound of Formula I

Another aspect of the present invention provides a process for the preparation of the compound of formula I, which is carried out according to the following scheme (example):

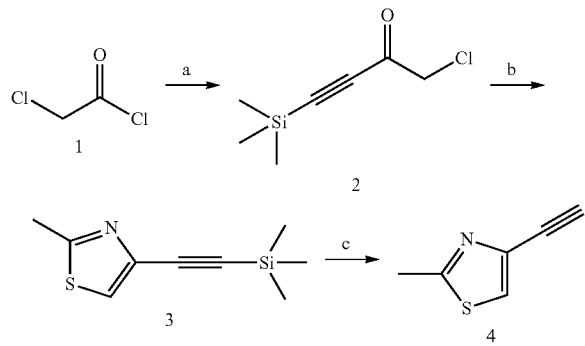

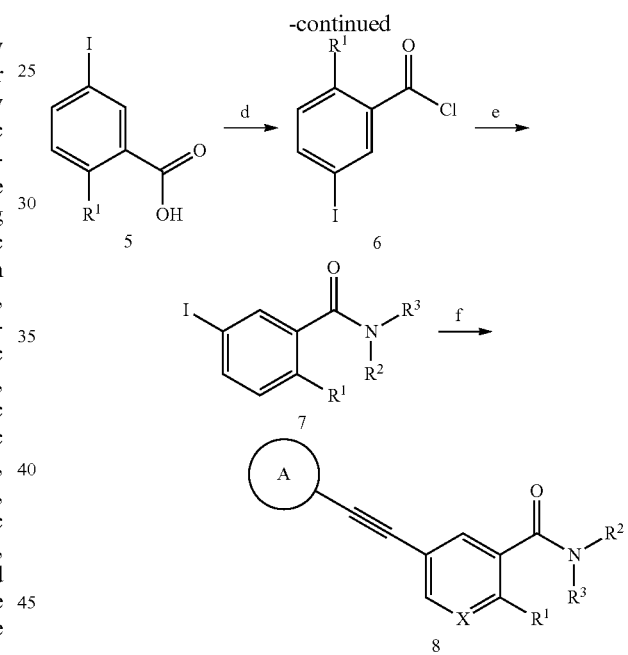

Step a: Aluminum trichloride is dissolved in an organic solvent, and then bis(trimethylsilyl)acetylene and compound 1 are added under ice bath and reacted to give compound 2; the organic solvent is tetrahydrofuran, diethyl ether, dimethylformamide, glycol dimethyl ether, ethylene glycol diethyl ether, dioxane, ethanol, methanol, ethyl acetate, dichloromethane or mixture thereof;

Step b: Compound 2 is dissolved in an organic solvent, and thioacetamide is added and stirred until the reaction is completed to give compound 3; the organic solvent is tetrahydrofuran, diethyl ether, dimethylformamide, glycol dimethyl ether, ethylene glycol diethyl ether, dioxane, ethanol, methanol, ethyl acetate, dichloromethane or mixture thereof;

Step c: Compound 3 is dissolved in an organic solvent and a strong base is added to complete reaction to obtain compound 4; the organic solvent is tetrahydrofuran, diethyl ether, dimethylformamide, glycol dimethyl ether, ethylene glycol diethyl ether, dioxane, ethanol, methanol, ethyl acetate, dichloromethane or mixture thereof; the strong base is NaOH, KOH, sodium ethoxide or sodium methoxide;

Step d: Thionyl chloride is added to compound 5 and heated to reflux to give an intermediate 6; the heating temperature ranges from 60-80° C.;

Step e: An amine is dissolved in an organic solvent and a certain amount of base is added. After the compound 6 is dissolved in an organic solvent, it is added dropwise to the amine solution under ice-bath to give an intermediate 7; the amine is selected from the group consisting of substituted or unsubstituted aniline, substituted or unsubstituted pyridinamine, tetrahydroisoquinoline, 2-methyltetrahydroisoquinoline, 7-oxa-2-azaspiro[3.5]nonane, 8-oxa-2-azaspiro[4.5] decane, 3-trifluoromethyl-5,6,7,8-tetrahydro-[1,2,4]triazolo [4,3-a]pyrazine hydrochloride; the organic solvent is tetrahydrofuran, diethyl ether, dimethylformamide, glycol dimethyl ether, ethylene glycol diethyl ether, dioxane, ethanol, methanol, ethyl acetate, dichloromethane or mixture thereof; the base is sodium acetate, NaOH, KOH, sodium ethoxide, sodium methoxide, sodium carbonate, potassium carbonate, triethylamine or diisopropylamine;

Step f: The intermediate 7 is dissolved in an organic solvent, a certain amount of base and alkynyl substrate are added, and then copper iodide and bis-triphenylphosphine palladium dichloride are added and heated to reflux to obtain compound 8; the organic solvent is tetrahydrofuran, toluene, diethyl ether, dimethylformamide, glycol dimethyl ether, ethylene glycol diethyl ether, dioxane, ethanol, methanol, ethyl acetate, dichloromethane or mixture thereof; and the base is sodium acetate, NaOH, KOH, sodium ethoxide, sodium methoxide, sodium carbonate, potassium carbonate, triethylamine or diisopropylamine; and the heating temperature ranges from 80 to 120° C.

The other compounds may be prepared by similar methods by selecting different starting materials.

Pharmaceutical Composition and the Administration Thereof

The compounds of the present invention possess outstanding activity of mGluR5 negative allosteric regulation. Therefore, the compounds of the present invention, and various crystal forms, pharmaceutically acceptable inorganic or organic salts, hydrates or solvates thereof, and the pharmaceutical composition comprising the compound of the present invention as a main active ingredient can be used for treating, preventing and alleviating diseases related to mGluR5 negative allosteric regulation, such as central nervous system and psychiatric system related diseases, etc.

The pharmaceutical composition of the invention comprises the compound of the present invention or the pharmaceutically acceptable salt thereof in a safe and effective dosage range and a pharmaceutically acceptable excipient or carrier. Wherein the "safe and effective dosage" means that the amount of compound is sufficient to significantly ameliorate the condition without causing significant side effects. Generally, the pharmaceutical composition contains 1-3000 (active dose range 3-30 mg/kg) mg compound of the invention per dose, preferably, 10-2000 mg compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compounds or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or the mixture thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

The liquid dosage forms for oral administration include pharmaceutically acceptable emulsions, solutions, suspensions, syrups or tinctures. In addition to the active compound, the liquid dosage form may contain any conventional inert diluent known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers and suspending agents, sweeteners, flavoring agents and perfumes.

In addition to the active compound, the suspension may contain suspending agent, for example, ethoxylated isooctadecanol, polyoxyethylene sorbitol and sorbitan ester, microcrystalline cellulose, aluminum methoxide and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosols, and inhalants. The active ingredient is mixed with physiologically acceptable carrier and any preservative, buffer, or propellant if necessary, under sterile conditions.

The compound of the present invention can be administrated alone, or in combination with any other pharmaceutically acceptable compound.

When the pharmaceutical composition is used, a safe and effective amount of compound of the present invention is applied to a mammal (such as human) in need of treatment, wherein the dose of administration is a pharmaceutically effective dose. For a person weighed 60 kg, the daily dose is usually 1-2000 mg, preferably 6-600 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight. The starting materials used in the present invention are commercially available without being specifically described.

EXAMPLE 1

The Preparation of 2-fluoro-5-(pyridin-2-ethynyl)-N-(4-fluorophenyl) benzamide (ZD001)

1.1 Synthesis of 2-fluoro-5-iodo-benzoyl chloride 500 mg of 2-fluoro-5-iodobenzoic acid was added to a 50 ml eggplant flask, and then 3 ml of thionyl chloride was added, and heated at 77° C. for 2 hours. The reaction was monitored by thin layer chromatography (TLC). After the reaction was completed, the mixture was cooled to room temperature and dried by rotary evaporation to remove thionyl chloride to give 524 mg 2-fluoro-5-iodo-benzoyl chloride as colorless liquid.

1.2 Synthesis of 2-fluoro-N-(4-fluorophenyl)-5-iodobenzamide 200 mg of 4-fluoroaniline was dissolved in 5 ml of ethyl acetate, and 260 μl of triethylamine was added. Then 2-fluoro-5-iodo-benzoyl chloride in ethyl acetate was added dropwise under ice-cooling, and the reaction was completed after 1.5 hours. 10 ml ethyl acetate was added to dilute, and 20 ml water was added to extract. The mixture was extracted with ethyl acetate for three times, washed once with saturated brine, dried over anhydrous sodium sulfate, and dried by rotary evaporation to obtain 620 mg 2-fluoro-N-(4-fluorophenyl)-5-iodobenzamide as light yellow solid.

1.3 Synthesis of Final Product ZD001

625 mg 2-fluoro-N-(4-fluorophenyl)-5-iodobenzamide was dissolved in toluene, 1.5 eq 2-ethynylpyridine and 2.2 eq triethylamine were added followed by 0.2 eq cuprous iodide, 0.2 eq bis(triphenyl-phosphine)palladium dichloride. The mixture was heated and stirred at 100° C. for 6 hours under an inert atmosphere. The reaction liquid was dried by rotary evaporation and purified to give 460 mg ZD001 as tan solid, yield 79%. $^1$H NMR (400 MHz, CDCl$_3$) δ 10.61 (s, 1H), 8.62 (d, J=4.1 Hz, 1H), 7.95-7.80 (m, 3H), 7.78-7.71 (m, 2H), 7.68 (d, J=7.8 Hz, 2H), 7.51-7.41 (m, 2H), 7.22 (t, J=8.9 Hz, 2H). LRMS (EI) m/z 335 (M+).

EXAMPLE 2

The Preparation of (2-chloro-5-(pyridin-2-ethynyl) phenyl) (7-oxa-2-aza-spiro [3.5] nonan-2-yl) methanone (ZD002)

2-fluoro-5-iodobenzoic acid was replaced by 2-chloro-5-iodobenzoic acid, and 4-fluoroaniline was replaced by 7-oxa-2-azaspiro [3.5] nonane, while the remaining raw materials, reagents and the preparation method were the same as those in Example 1 to give the product ZD002, yield 80%. $^1$H NMR (400 MHz, CDCl$_3$) δ 8.62 (m, J=4.9, 1.8, 0.9 Hz, 1H), 7.70 (m, J=7.7, 1.8 Hz, 1H), 7.56-7.55 (m, 1H), 7.54-7.50 (m, 2H), 7.40 (dd, J=8.1, 0.7 Hz, 1H), 7.30-7.26 (m, 1H), 3.94 (s, 4H), 3.65-3.49 (m, 4H), 1.89-1.70 (m, 4H). LRMS (EI) m/z 367 (M+).

EXAMPLE 3

The Preparation of (2-chloro-5-(pyridin-2-ethynyl) phenyl) (8-oxa-2-aza-spiro [4.5] dec-2-yl) methanone (ZD003)

2-fluoro-5-iodobenzoic acid was replaced by 2-chloro-5-iodobenzoic acid, and 4-fluoroaniline was replaced by 8-oxa-2-azaspiro [4.5] decane, while the remaining raw materials, reagents and the preparation method were the same as those in Example 1 to give the product ZD003, yield 80%. $^1$H NMR (400 MHz, CDCl$_3$) δ 8.63 (d, J=4.1 Hz, 1H), 7.70 (t, J=7.8 Hz, 1H), 7.57-7.49 (m, 3H), 7.43-7.38 (m, 1H), 7.28 (d, J=7.5 Hz, 1H), 3.83-3.65 (m, 4H), 3.44 (dd, J=104.9, 12.7 Hz, 2H), 1.87 (dt, J=27.5, 7.2 Hz, 3H), 1.64 (t, J=5.3 Hz, 2H), 1.60-1.48 (m, 3H). LRMS (EI) m/z 381 (M+).

EXAMPLE 4

The Preparation of 2-fluoro-N-(4-fluorophenyl)-5-((2-methylthiazol-4-yl) ethynyl) benzamide (ZD004)

2-ethynylpyridine was replaced by 4-ethynyl-2-methylthiazole, while the remaining raw materials, reagents and the preparation method were the same as those in Example 1 to give the product ZD004, yield 80%. $^1$H NMR (400 MHz, CDCl$_3$) δ 8.34 (dd, J=7.5, 2.1 Hz, 1H), 7.68 (dd, J=5.4, 3.1 Hz, 1H), 7.65-7.58 (m, 2H), 7.41 (s, 1H), 7.18 (dd, J=11.7, 8.6 Hz, 1H), 7.08 (t, J=8.6 Hz, 2H), 2.75 (s, 3H). LRMS (EI) m/z 355 (M+).

EXAMPLE 5

The Preparation of 2-chloro-N-(4-fluorophenyl)-5-(pyridine-2-ethynyl) benzamide (ZD036)

2-fluoro-5-iodobenzoic acid was replaced by 2-chloro-5-iodobenzoic acid, while the remaining raw materials, reagents and the preparation method were the same as those in Example 1 to give the product ZD036, yield 80%. $^1$H NMR (400 MHz, CDCl$_3$) δ 8.65 (s, 1H), 7.99 (s, 2H), 7.80 (s, 1H), 7.63 (d, J=8.3 Hz, 4H), 7.45 (d, J=8.1 Hz, 1H), 7.37 (s, 1H), 7.08 (t, J=8.3 Hz, 2H). LRMS (EI) m/z 351 (M+)

EXAMPLE 6

The Preparation of 2-chloro-N-(4-fluorophenyl)-5-((2-methylthiazol-4-yl) ethynyl) benzamide (ZD037)

2-fluoro-5-iodobenzoic acid was replaced by 2-chloro-5-iodobenzoic acid, and 2-ethynylpyridine was replaced by 4-ethynyl-2-methylthiazole, while the remaining raw materials, reagents and the preparation method were the same as those in Example 1 to give the product ZD037, yield 80%. $^1$H NMR (400 MHz, DMSO) δ 10.63 (s, 1H), 7.96 (s, 1H), 7.79 (d, J=1.7 Hz, 1H), 7.76-7.70 (m, 2H), 7.67 (dt, J=15.5, 5.2 Hz, 2H), 7.21 (t, J=8.9 Hz, 2H), 2.68 (s, 3H). LRMS (EI) m/z 371 (M+)

EXAMPLE 7

The Preparation of 2-fluoro-N-(4-fluorophenyl)-5-(pyridine-3-ethynyl) benzamide (ZD038)

2-ethynylpyridine was replaced by 3-ethynylpyridine, while the remaining raw materials, reagents and the preparation method were the same as those in Example 1 to give the product ZD038, yield 80%. $^1$H NMR (400 MHz, CDCl$_3$) δ 9.28-8.51 (s, 1H), 8.47-8.30 (m, 2H), 7.85 (d, J=7.8 Hz, 1H), 7.73-7.55 (m, 3H), 7.53-7.32 (m, 1H), 7.21 (dd, J=11.7, 8.6 Hz, 1H), 7.08 (t, J=8.6 Hz, 2H). LRMS (EI) m/z 335 (M+)

EXAMPLE 8

The Preparation of 2-fluoro-N-(4-fluorophenyl)-5-(pyridine-4-ethynyl) benzamide (ZD039)

2-ethynylpyridine was replaced by 4-ethynylpyridine, while the remaining raw materials, reagents and the preparation method were the same as those in Example 1 to give the product ZD039, yield 80%. $^1$H NMR (400 MHz, CDCl$_3$) δ 8.44-8.34 (m, 3H), 7.93-7.79 (m, 1H), 7.70 (s, 1H), 7.63 (dd, J=8.6, 4.6 Hz, 3H), 7.24-7.18 (m, 1H), 7.09 (t, J=8.5 Hz, 3H). LRMS (EI) m/z 335 (M+)

EXAMPLE 9

The Preparation of N-(4-fluorophenyl)-2-methyl-5-(pyridine-2-ethynyl) benzamide (ZD040)

2-fluoro-5-iodobenzoic acid was replaced by 2-methyl-5-iodobenzoic acid, while the remaining raw materials, reagents and the preparation method were the same as those in Example 1 to give the product ZD040, yield 80%. $^1$H NMR (400 MHz, CDCl$_3$) δ 8.57 (d, J=4.3 Hz, 1H), 8.23 (s, 1H), 7.73-7.57 (m, 4H), 7.49 (td, J=6.7, 3.2 Hz, 2H), 7.25-7.20 (m, 2H), 7.02 (t, J=8.6 Hz, 2H), 2.47 (s, 3H). LRMS (EI) m/z 331 (M+)

EXAMPLE 10

The Preparation of N-(4-fluorophenyl)-2-methyl-5-((2-methylthiazol-4-yl) ethynyl) benzamide (ZD041)

2-fluoro-5-iodobenzoic acid was replaced by 2-methyl-5-iodobenzoic acid, and 2-ethynylpyridine was replaced by 4-ethynyl-2-methylthiazole, while the remaining raw materials, reagents and the preparation method were the same as those in Example 1 to give the product ZD041, yield 80%. $^1$H NMR (400 MHz, CDCl$_3$) δ 7.79 (s, 1H), 7.66 (s, 1H), 7.60 (dd, J=8.5, 4.7 Hz, 2H), 7.49 (s, 1H), 7.36 (s, 1H), 7.24 (d, J=7.8 Hz, 1H), 7.05 (t, J=8.5 Hz, 2H), 2.74 (s, 3H), 2.50 (s, 3H). LRMS (EI) m/z 351 (M+)

EXAMPLE 11

The Synthesis of 2-fluoro-5-(pyridin-2-ethynyl)-N-(pyridin-3-yl)benzamide (ZD042)

4-fluoroaniline was replaced by 3-aminopyridine, while the remaining raw materials, reagents and the preparation method were the same as those in Example 1 to give the product ZD042, yield 80%. $^1$H NMR (400 MHz, CDCl$_3$) δ 8.72 (d, J=13.1 Hz, 2H), 8.65-8.59 (m, 1H), 8.41 (d, J=3.5 Hz, 1H), 8.31 (dd, J=7.4, 2.2 Hz, 2H), 7.74-7.68 (m, 2H), 7.53 (dt, J=7.8, 1.0 Hz, 1H), 7.35 (dd, J=8.3, 4.7 Hz, 1H), 7.30-7.26 (m, 1H), 7.19 (dd, J=11.5, 8.6 Hz, 1H). LRMS (EI) m/z 318 (M+)

EXAMPLE 12

The Synthesis of 2-fluoro-5-((2-methylthiazol-4-yl) ethynyl)-N-(pyridin-3-yl)benzamide (ZD043)

2-ethynylpyridine was replaced by 4-ethynyl-2-methylthiazole, 4-fluoroaniline was replaced by 3-aminopyridine, while the remaining raw materials, reagents and the preparation method were the same as those in Example 1 to give the product ZD043, yield 80%. $^1$H NMR (400 MHz, CDCl$_3$) δ 8.74 (s, 1H), 8.67 (d, J=13.8 Hz, 1H), 8.41 (s, 1H), 8.33 (d, J=8.1 Hz, 1H), 8.27 (dd, J=7.4, 2.2 Hz, 1H), 7.67 (ddd, J=8.4, 4.9, 2.3 Hz, 1H), 7.40 (s, 1H), 7.36 (s, 1H), 7.17 (dd, J=11.6, 8.6 Hz, 1H), 2.73 (s, 3H). LRMS (EI) m/z 338 (M+)

EXAMPLE 13

The Preparation of N-(4-cyanophenyl)-2-fluoro-5-(pyridine-2-ethynyl) benzamide (ZD044)

4-fluoroaniline was replaced by 4-cyanoaniline, while the remaining raw materials, reagents and the preparation method were the same as those in Example 1 to give the product ZD044, yield 80%. $^1$H NMR (400 MHz, CDCl$_3$) δ 8.70 (d, J=14.4 Hz, 1H), 8.35 (d, J=7.2 Hz, 1H), 7.82 (d, J=8.7 Hz, 2H), 7.75 (s, 2H), 7.67 (d, J=8.6 Hz, 2H), 7.62-7.50 (m, 1H), 7.39-7.27 (m, 1H), 7.21 (dd, J=11.6, 8.5 Hz, 1H). LRMS (EI) m/z 342 (M+)

EXAMPLE 14

The Preparation of N-(4-cyanophenyl)-2-fluoro-5-((2-methylthiazol-4-yl) ethynyl) benzamide (ZD045)

2-ethynylpyridine was replaced by 4-ethynyl-2-methylthiazole, 4-fluoroaniline was replaced by 4-cyanoaniline, while the remaining raw materials, reagents and the preparation method were the same as those in Example 1 to give the product ZD045, yield 80%. $^1$H NMR (400 MHz, DMSO) δ 10.95 (s, 1H), 7.94 (s, 1H), 7.92 (s, 1H), 7.91-7.88 (m, 2H), 7.85 (s, 1H), 7.83 (s, 1H), 7.82-7.77 (m, 1H), 7.47 (s, 1H), 2.68 (s, 3H). LRMS (EI) m/z 362 (M+)

EXAMPLE 15

The Preparation of (3,4-dihydro-isoquinolin-2(1H)-yl)(2-fluoro-5-(pyridin-2-ylethynyl)phenyl)methanone (ZD046)

4-fluoroaniline was replaced by 3,4-dihydroisoquinoline, while the remaining raw materials, reagents and the preparation method were the same as those in Example 1 to give the product ZD046, yield 80%. $^1$H NMR (400 MHz, CDCl$_3$) δ 8.62 (s, 1H), 7.73-7.61 (m, 3H), 7.54-7.49 (m, 1H), 7.30-7.26 (m, 1H), 7.25-7.17 (m, 3H), 7.14 (dd, J=11.5, 6.5 Hz, 2H), 4.72 (d, J=170.6 Hz, 2H), 3.58 (t, J=5.8 Hz, 2H), 2.93 (dt, J=42.1, 5.6 Hz, 2H). LRMS (EI) in/z 357 (M+)

EXAMPLE 16

The Preparation of (3,4-dihydro-isoquinolin-2(1H)-yl)(2-fluoro-5-((2-methylthiazol-4-yl)ethynyl)phenyl)methanone (ZD047)

2-ethynylpyridine was replaced by 4-ethynyl-2-methylthiazole, 4-fluoroaniline was replaced by 3,4-dihydroisoquinoline, while the remaining raw materials, reagents and the preparation method were the same as those in Example 1 to give the product ZD047, yield 80%. $^1$H NMR (400 MHz, CDCl$_3$) δ 7.62-7.56 (m, 2H), 7.36 (d, J=7.0 Hz, 1H), 7.25-7.16 (m, 3H), 7.12 (t, J=9.0 Hz, 2H), 4.71 (d, J=171.9 Hz, 2H), 3.57 (t, J=5.8 Hz, 2H), 2.92 (d, J=43.6 Hz, 2H), 2.73 (d, J=3.6 Hz, 3H). LRMS (EI) m/z 377 (M+)

EXAMPLE 17

The Preparation of (2-fluoro-5-(pyridin-2-ylethynyl)phenyl)(1-methyl-3,4-dihydro-isoquinolin-2(1H)-yl)methanone (ZD048)

4-fluoroaniline was replaced by 1-methyl-3,4-dihydroisoquinoline, while the remaining raw materials, reagents and the preparation method were the same as those in Example 1 to give the product ZD048, yield 80%. $^1$H NMR (400 MHz, CDCl$_3$) δ 8.62 (d, J=4.7 Hz, 1H), 7.74-7.59 (m, 3H), 7.51 (d, J=7.8 Hz, 1H), 7.25-7.23 (m, 1H), 7.23-7.09 (m, 5H), 5.81 (d, J=6.7 Hz, 1H), 3.72-3.42 (m, 2H), 2.73 (d, J=16.0 Hz, 2H), 1.60 (d, J=6.8 Hz, 3H). LRMS (EI) m/z 371 (M+)

EXAMPLE 18

The Preparation of (2-fluoro-5-((2-methyl-thiazol-4-yl)ethynyl)phenyl)(1-methyl-3,4-dihydro-isoquinolin-2(1H)-yl)methanone (ZD049)

2-ethynylpyridine was replaced by 4-ethynyl-2-methylthiazole, 4-fluoroaniline was replaced by 1-methyl-3,4-dihydroisoquinoline, while the remaining raw materials, reagents and the preparation method were the same as those in Example 1 to give the product ZD049, yield 80%. $^1$H NMR (400 MHz, CDCl$_3$) δ 7.62-7.55 (m, 2H), 7.37 (s, 1H), 7.18 (ddd, J=11.5, 9.2, 5.7 Hz, 3H), 7.11 (dd, J=11.8, 5.7 Hz, 2H), 5.80 (d, J=6.7 Hz, 1H), 3.54 (dd, J=50.6, 6.1 Hz, 2H), 3.34-2.81 (m, 2H), 2.73 (s, 3H), 1.59 (d, J=6.8 Hz, 3H). LRMS (EI) m/z 391 (M+).

EXAMPLE 19

The Synthesis of 2-fluoro-5-((2-methylthiazol-4-ylethynyl)-N-(pyridin-3-yl)nicotinamide (ZD050)

2-ethynylpyridine was replaced by 4-ethynyl-2-methylthiazole, 4-fluoroaniline was replaced by 3-aminopyridine, 2-fluoro-5-iodobenzoic acid was replaced by 2-fluoro-5-iodo-picolinic acid, while the remaining raw materials, reagents and the preparation method were the same as those in Example 1 to give the product ZD050, yield 80%. $^1$H NMR (400 MHz, CDCl$_3$) δ7.699 (s, 1H), 2.501 (s, 3H), 8.869 (1H, d), 8.894 (d, 1H), 8.402 (ddd, 1H), 7.476 (ddd, 1H), 7.316 (ddd, 1H), 8.404 (ddd, 1H). LRMS (EI) m/z 339 (M+).

EXAMPLE 20

The Preparation of 2-fluoro-N-(4-fluorophenyl)-5-(pyridin-2-ylethynyl)nicotinamide (ZD051)

2-fluoro-5-iodobenzoic was replaced by 2-fluoro-5-iodopicolinic acid, while the remaining raw materials, reagents and the preparation method were the same as those in Example 1 to give the product ZD051, yield 80%. $^1$H NMR (400 MHz, CDCl$_3$) δ8.719 (1H, d), 8.813 (1H, d), 7.743 (1H, ddd), 7.743 (1H, ddd), 7.017 (1H, ddd), 7.017 (1H, ddd), 7.492 (1H, ddd), 8.729 (1H, ddd), 7.848 (1H, ddd), 7.221 (1H, ddd). LRMS (EI) m/z 336 (M+).

EXAMPLE 21

The Preparation of (3,4-dihydro-isoquinolin-2(1H)-yl)(2-fluoro-5-((2-methyl-thiazol-4-yl)ethynyl)pyridin-3-yl)methanone (ZD052)

2-ethynylpyridine was replaced by 4-ethynyl-2-methylthiazole, 4-fluoroaniline was replaced by 3,4-dihydroisoquinoline, 2-fluoro-5-iodobenzoic acid was replaced by 2-fluoro-5-iodo-picolinic acid, while the remaining raw materials, reagents and the preparation method were the same as those in Example 1 to give the product ZD052, yield 80%. $^1$H NMR (400 MHz, CDCl$_3$) δ7.264 (1H), 2.455 (s, 3H), 8.688 (1H, d), 8.758 (1H, d), 4.354 (1H, d), 4.467 (1H, d), 3.658 (1H, ddd), 3.359 (1H, ddd), 2.926 (1H, ddd), 3.020 (1H, ddd), 6.866 (1H, ddd), 7.240 (1H, ddd), 7.041 (1H, ddd), 7.168 (1H, ddd). LRMS (EI) m/z 378 (M+).

EXAMPLE 22

The Preparation of 2-fluoro-N-(4-fluorophenyl)-5-((2-methylthiazol-4-yl)ethynyl)nicotinamide (ZD053)

2-ethynylpyridine was replaced by 4-ethynyl-2-methylthiazole, 2-fluoro-5-iodobenzoic acid was replaced by 2-fluoro-5-iodo-picolinic acid, while the remaining raw materials, reagents and the preparation method were the same as those in Example 1 to give the product ZD053, yield 80%. $^1$H NMR (400 MHz, CDCl$_3$) δ7.265 (s, 1H), 2.454 (s, 3H), 8.690 (1H, d), 8.766 (1H, d), 7.743 (1H, ddd), 7.743 (1H, ddd), 7.017 (1H, ddd), 7.017 (1H, ddd). LRMS (EI) m/z 356 (M+).

EXAMPLE 23

The Preparation of 2-chloro-N-(4-fluorophenyl)-5-((2-methylthiazol-4-yl)ethynyl)nicotinamide (ZD054)

2-ethynylpyridine was replaced by 4-ethynyl-2-methyl-thiazole, 2-fluoro-5-iodobenzoic acid was replaced by 2-chloro-5-iodo-picolinic acid, while the remaining raw materials, reagents and the preparation method were the same as those in Example 1 to give the product ZD054, yield 80%. $^1$H NMR (400 MHz, CDCl$_3$) δ8.690 (1H, d), 8.703 (1H, d), 7.744 (1H, ddd), 7.744 (1H, ddd), 7.018 (1H, ddd), 7.018 (1H, ddd), 7.284 (s, 1H), 2.408 (s, 3H). LRMS (EI) m/z 373 (M+).

EXAMPLE 24

The Synthesis of 2-fluoro-5-(pyridin-2-ylethynyl)-N-(pyridin-3-yl)nicotinamide (ZD055)

2-fluoro-5-iodobenzoic acid was replaced by 2-fluoro-5-iodopicolinic acid, 4-fluoroaniline was replaced by 3-aminopyridine, while the remaining raw materials, reagents and the preparation method were the same as those in Example 1 to give the product ZD055, yield 80%. $^1$H NMR (400 MHz, CDCl$_3$) δ8.719 (1H, d), 8.813 (1H, d), 8.402 (1H, ddd), 7.476 (1H, ddd), 7.315 (1H, ddd), 7.492 (1H, ddd), 8.404 (1H, ddd), 8.729 (1H, ddd), 7.848 (1H, ddd), 7.221 (1H, ddd). LRMS (EI) m/z 319 (M+).

EXAMPLE 25

The Preparation of (3,4-dihydro-isoquinolin-2(1H)-yl)(2-fluoro-5-(pyridin-2-ylethynyl)pyridin-3-yl)methan one (ZD056)

2-fluoro-5-iodobenzoic acid was replaced by 2-fluoro-5-iodopicolinic acid, 4-fluoroaniline was replaced by 3,4-dihydroisoquinoline, while the remaining raw materials, reagents and the preparation method were the same as those in Example 1 to give the product ZD056, yield 80%. $^1$H NMR (400 MHz, CDCl$_3$) δ8.718 (1H, d), 8.807 (1H, d), 4.356 (1H, d), 4.468 (1H, d), 3.659 (1H, ddd), 3.359 (1H, ddd), 2.926 (1H, ddd), 3.020 (1H, ddd), 6.866 (1H, ddd), 7.492 (1H, ddd), 7.240 (1H, ddd), 7.041 (1H, ddd), 8.729 (1H, ddd), 7.848 (1H, ddd), 7.168 (1H, ddd), 7.221 (1H, ddd). LRMS (EI) m/z 358 (M+).

EXAMPLE 26

The Preparation of 2-fluoro-5-((2-methylthiazol-4-yl)ethynyl)-N-benzoyl-aniline (ZD057)

2-ethynylpyridine was replaced by 4-ethynyl-2-methyl-thiazole, 4-fluoroaniline was replaced by aniline, while the remaining raw materials, reagents and the preparation method were the same as those in Example 1 to give the product ZD057, yield 80%. $^1$H NMR (400 MHz, CDCl$_3$) δ7.264 (s, 1H), 2.406 (s, 3H), 8.503 (1H, dd), 7.857 (1H, dd), 7.401 (1H, dd), 7.481 (1H, dddd), 7.481 (1H, dddd), 7.272 (1H, dddd), 7.272 (1H, dddd), 7.069 (1H, tt). LRMS (EI) m/z 337 (M+).

EXAMPLE 27

The Synthesis of 2-cyano-5-((2-methylthiazol-4-yl)ethynyl)-N-(pyridin-3-yl)benzamide (ZD058)

2-ethynylpyridine was replaced by 4-ethynyl-2-methyl-thiazole, 2-fluoro-5-iodobenzoic acid was replaced by 2-cyano-5-iodo-picolinic acid, 4-fluoroaniline was replaced by 3-aminopyridine, while the remaining raw materials, reagents and the preparation method were the same as those in Example 1 to give the product ZD058, yield 80%. $^1$H NMR (400 MHz, CDCl$_3$) δ7.411 (s, 1H), 2.554 (s, 3H), 8.561 (1H, dd), 7.793 (1H, dd), 8.051 (1H, dd), 8.404 (1H, ddd), 7.455 (1H, ddd), 7.317 (1H, ddd), 8.405 (1H, ddd). LRMS (EI) m/z 345 (M+).

EXAMPLE 28

The Synthesis of 5-((2-methylthiazol-4-yl)ethynyl)-N-(pyridin-3-yl)-2-(trifluoromethyl)benzamide (ZD059)

2-ethynylpyridine was replaced by 4-ethynyl-2-methyl-thiazole, 2-fluoro-5-iodobenzoic acid was replaced by 2-trifluoromethyl-5-iodo-picolinic acid, 4-fluoroaniline was replaced by 3-aminopyridine, while the remaining raw materials, reagents and the preparation method were the same as those in Example 1 to give the product ZD059, yield 80%. $^1$H NMR (400 MHz, CDCl$_3$) δ7.461 (s, 1H), 2.478 (s, 3H), 8.585 (1H, dd), 7.899 (1H, dd), 7.781 (1H, dd), 8.404 (1H, ddd), 7.455 (1H, ddd), 7.317 (1H, ddd), 8.405 (1H, ddd). LRMS (EI) m/z 388 (M+).

EXAMPLE 29

The Preparation of N-(4-fluorophenyl)-5-((2-methylthiazol-4-yl)ethynyl)-2-(trifluoromethyl)benzamide (ZD060)

2-ethynylpyridine was replaced by 4-ethynyl-2-methyl-thiazole, 2-fluoro-5-iodobenzoic acid was replaced by 2-trifluoromethyl-5-iodo-picolinic acid, while the remaining raw materials, reagents and the preparation method were the same as those in Example 1 to give the product ZD060, yield 80%. $^1$H NMR (400 MHz, CDCl$_3$) δ7.461 (s, 1H), 2.478 (s, 3H), 8.585 (1H, dd), 7.899 (1H, dd), 7.781 (1H, dd), 7.745 (1H, ddd), 7.746 (1H, ddd), 7.018 (1H, ddd), 7.018 (1H, ddd). LRMS (EI) m/z 405 (M+).

EXAMPLE 30

The Preparation of 2-cyano-N-(4-fluorophenyl)-5-((2-methylthiazol-4-yl) ethynyl) benzamide (ZD061)

2-ethynylpyridine was replaced by 4-ethynyl-2-methyl-thiazole, 2-cyano-5-iodobenzoic acid was replaced by 2-cyano-5-iodo-picolinic acid, while the remaining raw materials, reagents and the preparation method were the same as those in Example 1 to give the product ZD061, yield 80%. $^1$H NMR (400 MHz, CDCl$_3$) δ7.379 (s, 1H), 8.556

(1H, dd), 7.794 (1H, dd), 8.044 (1H, dd), 7.745 (1H, ddd), 7.745 (1H, ddd), 7.018 (1H, ddd), 7.018 (1H, ddd). LRMS (EI) m/z 362 (M+).

EXAMPLE 31

The Preparation of 4-((2-methylthiazol-4-yl)ethynyl)-2-(1,2,3,4-dihydroisoquinoline-2-carbonyl)benzonitrile (ZD062)

2-ethynylpyridine was replaced by 4-ethynyl-2-methylthiazole, 2-fluoro-5-iodobenzoic acid was replaced by 2-cyano-5-iodo-picolinic acid, 4-fluoroaniline was replaced by 3,4-dihydroisoquinoline, while the remaining raw materials, reagents and the preparation method were the same as those in Example 1 to give the product ZD062, yield 80%. $^1$H NMR (400 MHz, CDCl$_3$) δ7.410 (s, 1H), 2.554 (s, 3H), 8.544 (1H, dd), 7.790 (1H, dd), 8.046 (1H, dd), 4.330 (1H, d), 4.474 (1H, d), 3.665 (1H, ddd), 3.375 (1H, ddd), 2.928 (1H, ddd), 3.023 (1H, ddd), 6.867 (1H, ddd), 7.240 (1H, ddd), 7.042 (1H, ddd), 7.168 (1H, ddd). LRMS (EI) m/z 384 (M+).

EXAMPLE 31

The Preparation of (3,4-dihydro-isoquinolin-2 (1H)-yl)(5-((2-methyl-thiazol-4-yl) ethynyl)-2-(trifluoromethyl)phenyl)methanone (ZD063)

2-ethynylpyridine was replaced by 4-ethynyl-2-methylthiazole, 2-fluoro-5-iodobenzoic acid was replaced by 2-trifluoromethyl-5-iodo-picolinic acid, 4-fluoroaniline was replaced by 3,4-dihydroisoquinoline, while the remaining raw materials, reagents and the preparation method were the same as those in Example 1 to give the product ZD063, yield 80%. $^1$H NMR (400 MHz, CDCl$_3$) δ7.459 (s, 1H), 2.477 (s, 3H), 8.567 (1H, dd), 7.896 (1H, dd), 7.779 (1H, dd), 4.325 (1H, d), 4.467 (1H, d), 3.663 (1H, ddd), 3.374 (1H, ddd), 2.928 (1H, ddd), 3.023 (1H, ddd), 6.867 (1H, ddd), 7.240 (1H, ddd), 7.042 (1H, ddd), 7.168 (1H, ddd). LRMS (EI) m/z 427 (M+).

EXAMPLE 33

The Preparation of 2-fluoro-N-(2-fluorophenyl)-5-((2-methylthiazol-4-yl) ethynyl) benzamide (ZD064)

2-ethynylpyridine was replaced by 4-ethynyl-2-methylthiazole, 4-fluoroaniline was replaced by 2-fluoroaniline, while the remaining raw materials, reagents and the preparation method were the same as those in Example 1 to give the product ZD064, yield 80%. $^1$H NMR (400 MHz, CDCl$_3$) δ7.264 (s, 1H), 2.406 (s, 3H), 8.504 (1H, dd), 7.858 (1H, dd), 7.401 (1H, dd), 8.107 (1H, ddd), 7.025 (1H, ddd), 7.235 (1H, ddd), 7.035 (1H, ddd). LRMS (EI) m/z 355 (M+).

EXAMPLE 34

The Preparation of 2-fluoro-N-(3-fluorophenyl)-5-((2-methylthiazol-4-yl) ethynyl) benzamide (ZD065)

2-ethynylpyridine was replaced by 4-ethynyl-2-methylthiazole, 4-fluoroaniline was replaced by 3-fluoroaniline, while the remaining raw materials, reagents and the preparation method were the same as those in Example 1 to give the product ZD065, yield 80%. $^1$H NMR (400 MHz, CDCl$_3$) δ7.264 (s, 1H), 2.406 (s, 3H), 8.503 (1H, dd), 7.858 (1H, dd), 7.401 (1H, dd), 7.722 (1H, ddd), 7.533 (1H, ddd), 7.335 (1H, ddd), 7.013 (1H, ddd). LRMS (EI) m/z 355 (M+).

EXAMPLE 35

The Preparation of N-(3,4-difluorophenyl)-2-fluoro-5-((2-methylthiazol-4-yl) ethynyl) benzamide (ZD066)

2-ethynylpyridine was replaced by 4-ethynyl-2-methylthiazole, 4-fluoroaniline was replaced by 3,4-difluoroaniline, while the remaining raw materials, reagents and the preparation method were the same as those in Example 1 to give the product ZD066, yield 80%. $^1$H NMR (400 MHz, CDCl$_3$) δ7.264 (s, 1H), 2.406 (s, 3H), 8.504 (1H, dd), 7.858 (1H, dd), 7.401 (1H, dd), 7.725 (1H, dd), 7.278 (1H, dd), 7.299 (1H, dd). LRMS (EI) m/z 373 (M+).

EXAMPLE 36

The Preparation of N-(2,4-difluorophenyl)-2-fluoro-5-((2-methylthiazol-4-yl) ethynyl) benzamide (ZD067)

2-ethynylpyridine was replaced by 4-ethynyl-2-methylthiazole, 4-fluoroaniline was replaced by 2,4-difluoroaniline, while the remaining raw materials, reagents and the preparation method were the same as those in Example 1 to give the product ZD067, yield 80%. $^1$H NMR (400 MHz, CDCl$_3$) δ7.566 (s, 1H), 2.523 (s, 3H), 7.887 (1H, dd), 7.988 (1H, dd), 7.516 (1H, dd), 7.538 (1H, dd), 7.397 (1H, dd), 6.877 (1H, dd). LRMS (EI) m/z 373 (M+).

EXAMPLE 37

The Preparation of N-(4-chlorophenyl)-2-fluoro-5-((2-methylthiazol-4-yl) ethynyl) benzamide (ZD068)

2-ethynylpyridine was replaced by 4-ethynyl-2-methylthiazole, 4-fluoroaniline was replaced by 4-chloroaniline, while the remaining raw materials, reagents and the preparation method were the same as those in Example 1 to give the product ZD068, yield 80%. $^1$H NMR (400 MHz, CDCl$_3$) δ7.417 (1H, ddd), 7.417 (1H, ddd), 7.750 (1H, ddd), 7.750 (1H, ddd), 8.503 (1H, dd), 7.392 (1H, dd), 7.903 (1H, dd), 7.264 (s, 1H), 2.406 (s, 3H). LRMS (EI) m/z 372 (M+).

EXAMPLE 38

The Preparation of 2-fluoro-5-((2-methylthiazol-4-yl)ethynyl)-N-(4-(trifluoromethyl)phenyl)benzamide (ZD069)

2-ethynylpyridine was replaced by 4-ethynyl-2-methylthiazole, 4-fluoroaniline was replaced by 4-trifluoromethylaniline, while the remaining raw materials, reagents and the preparation method were the same as those in Example 1 to give the product ZD069, yield 80%. $^1$H NMR (400 MHz, CDCl$_3$) δ7.264 (s, 1H), 2.406 (s, 3H), 8.503 (1H, dd), 7.858

(1H, dd), 7.401 (1H, dd), 7.251 (1H, ddd), 7.251 (1H, ddd), 7.573 (1H, ddd), 7.573 (1H, ddd). LRMS (EI) m/z 405 (M+).

EXAMPLE 39

The Preparation of 2-fluoro-N-(4-methoxyphenyl)-5-((2-methylthiazol-4-yl)ethynyl) benzamide (ZD070)

2-ethynylpyridine was replaced by 4-ethynyl-2-methylthiazole, 4-fluoroaniline was replaced by 4-methoxyaniline, while the remaining raw materials, reagents and the preparation method were the same as those in Example 1 to give the product ZD070, yield 80%. $^1$H NMR (400 MHz, CDCl$_3$) δ7.264 (s, 1H), 2.406 (s, 3H), 8.503 (1H, dd), 7.858 (1H, dd), 7.401 (1H, dd), 7.277 (1H, ddd), 7.277 (1H, ddd), 6.636 (1H, ddd), 6.636 (1H, ddd), 3.760 (s, 3H). LRMS (EI) m/z 367 (M+).

EXAMPLE 40

The Preparation of 2-fluoro-5-((2-methylthiazol-4-yl)ethynyl)-N-(pyridin-2-yl)benzamide (ZD071)

2-ethynylpyridine was replaced by 4-ethynyl-2-methylthiazole, 4-fluoroaniline was replaced by 2-aminopyridine, while the remaining raw materials, reagents and the preparation method were the same as those in Example 1 to give the product ZD071, yield 80%. $^1$H NMR (400 MHz, CDCl$_3$) δ7.265 (s, 1H), 2.406 (s, 3H), 8.507 (1H, dd), 7.859 (1H, dd), 7.402 (1H, dd), 7.661 (1H, ddd), 8.404 (1H, ddd), 7.755 (1H, ddd), 7.106 (1H, ddd). LRMS (EI) m/z 338 (M+).

EXAMPLE 41

The Preparation of 2-fluoro-5-((2-methylthiazol-4-yl)ethynyl)-N-(pyridin-4-yl)benzamide (ZD072)

2-ethynylpyridine was replaced by 4-ethynyl-2-methylthiazole, 4-fluoroaniline was replaced by 4-aminopyridine, while the remaining raw materials, reagents and the preparation method were the same as those in Example 1 to give the product ZD072, yield 80%. $^1$H NMR (400 MHz, CDCl$_3$) δ7.264 (s, 1H), 2.406 (s, 3H), 8.505 (1H, dd), 7.858 (1H, dd), 7.401 (1H, dd), 7.971 (1H, ddd), 7.971 (1H, ddd), 8.501 (1H, ddd), 8.500 (1H, ddd). LRMS (EI) m/z 338 (M+).

EXAMPLE 42

The Preparation of 2-fluoro-N-(6-fluoropyridin-3-yl)-5-((2-methylthiazol-4-yl) ethynyl) benzamide (ZD073)

2-ethynylpyridine was replaced by 4-ethynyl-2-methylthiazole, 4-fluoroaniline was replaced by 6-fluoro-3-aminopyridine, while the remaining raw materials, reagents and the preparation method were the same as those in Example 1 to give the product ZD073, yield 80%. $^1$H NMR (400 MHz, CDCl$_3$) δ7.264 (s, 1H), 2.406 (s, 3H), 8.504 (1H, dd), 7.858 (1H, dd), 7.400 (1H, dd), 7.805 (1H, dd), 7.410 (1H, dd), 7.284 (1H, dd). LRMS (EI) m/z 356 (M+).

EXAMPLE 43

The Preparation of N-(6-chloropyridin-3-yl)-2-fluoro-5-((2-methylthiazol-4-yl) ethynyl) benzamide (ZD074)

2-ethynylpyridine was replaced by 4-ethynyl-2-methylthiazole, 4-fluoroaniline was replaced by 6-chloro-3-aminopyridine, while the remaining raw materials, reagents and the preparation method were the same as those in Example 1 to give the product ZD074, yield 80%. $^1$H NMR (400 MHz, CDCl$_3$) δ7.303 (1H, dd), 7.929 (1H, dd), 7.423 (1H, dd), 8.504 (1H, dd), 7.391 (1H, dd), 7.902 (1H, dd), 7.264 (s, 1H), 2.406 (s, 3H). LRMS (EI) m/z 373 (M+).

EXAMPLE 44

The Preparation of 2-fluoro-5-((2-methylthiazol-4-yl)ethynyl)-N-(p-methylphenyl)benzamide (ZD075)

2-ethynylpyridine was replaced by 4-ethynyl-2-methylthiazole, 4-fluoroaniline was replaced by 6-methyl-3-aminopyridine, while the remaining raw materials, reagents and the preparation method were the same as those in Example 1 to give the product ZD075, yield 80%. $^1$H NMR (400 MHz, CDCl$_3$) δ7.264 (s, 1H), 2.406 (s, 3H), 8.503 (1H, dd), 7.857 (1H, dd), 7.401 (1H, dd), 7.186 (1H, ddd), 7.187 (1H, ddd), 7.079 (1H, ddd), 7.079 (1H, ddd), 2.210 (s, 3H). LRMS (EI) m/z 351 (M+).

EXAMPLE 45

The Preparation of 2-fluoro-N-(pyridin-3-yl)-5-(thiazol-4-ylethynyl) benzamide (ZD076)

2-ethynylpyridine was replaced by 4-ethynylthiazole, 4-fluoroaniline was replaced by 3-aminopyridine, while the remaining raw materials, reagents and the preparation method were the same as those in Example 1 to give the product ZD076, yield 80%. $^1$H NMR (400 MHz, CDCl$_3$) δ8.388 (1H, d), 7.214 (1H, d), 8.514 (1H, dd), 7.858 (1H, dd), 7.411 (1H, dd), 8.402 (1H, ddd), 7.474 (1H, ddd), 7.315 (1H, ddd), 8.404 (1H, ddd). LRMS (EI) m/z 324 (M+).

EXAMPLE 46

The Preparation of 2-fluoro-5-((2-fluorothiazol-4-yl)ethynyl)-N-(pyridin-3-yl)benzamide (ZD077)

2-ethynylpyridine was replaced by 4-ethynyl-2-fluorothiazole, 4-fluoroaniline was replaced by 3-aminopyridine, while the remaining raw materials, reagents and the preparation method were the same as those in Example 1 to give the product ZD077, yield 80%. 1H NMR (400 MHz, CDCl3) δ7.139 (s, 1H), 8.503 (1H, dd), 7.858 (1H, dd), 7.401 (1H, dd), 8.402 (1H, ddd), 7.474 (1H, ddd), 7.315 (1H, ddd), 8.404 (1H, ddd). LRMS (EI) m/z 342 (M+).

EXAMPLE 47

The Preparation of 5-((2-chlorothiazol-4-ylethynyl)-2-fluoro-N-(pyridin-3-yl)benzamide (ZD078)

2-ethynylpyridine was replaced by 4-ethynyl-2-chlorothiazole, 4-fluoroaniline was replaced by 3-aminopyridine, while the remaining raw materials, reagents and the preparation method were the same as those in Example 1 to give the product ZD078, yield 80%. $^1$H NMR (400 MHz, CDCl$_3$) δ7.174 (s, 1H), 8.505 (1H, dd), 7.858 (1H, dd), 7.403 (1H, dd), 8.402 (1H, ddd), 7.474 (1H, ddd), 7.315 (1H, ddd), 8.404 (1H, ddd). LRMS (EI) m/z 359 (M+).

EXAMPLE 48

The Preparation of 2-fluoro-N-(pyridin-3-yl)-5-((2-(trifluoromethyl)thiazol-4-yl) ethynyl) benzamide (ZD079)

2-ethynylpyridine was replaced by 4-ethynyl-2-trifluoromethylthiazole, 4-fluoroaniline was replaced by 3-aminopyridine, while the remaining raw materials, reagents and the preparation method were the same as those in Example 1 to give the product ZD079, yield 80%. $^1$H NMR (400 MHz, CDCl$_3$) δ7.236 (s, 1H), 8.515 (1H, dd), 7.858 (1H, dd), 7.412 (1H, dd), 8.402 (1H, ddd), 7.474 (1H, ddd), 7.315 (1H, ddd), 8.404 (1H, ddd). LRMS (EI) m/z 392 (M+).

EXAMPLE 49

The Preparation of 2-fluoro-5-((6-methylpyridin-2-yl)ethynyl)-N-(pyridin-3-yl)benzamide (ZD080)

2-ethynylpyridine was replaced by 2-ethynyl-6-methylpyridine, 4-fluoroaniline was replaced by 3-aminopyridine, while the remaining raw materials, reagents and the preparation method were the same as those in Example 1 to give the product ZD080, yield 80%. $^1$H NMR (400 MHz, CDCl$_3$) δ7.567 (1H, dd), 8.587 (1H, dd), 7.954 (1H, dd), 8.402 (1H, ddd), 7.474 (1H, ddd), 7.315 (1H, ddd), 8.404 (1H, ddd), 7.294 (1H, dd), 7.653 (1H, dd), 7.008 (1H, dd), 2.565 (s, 3H). LRMS (EI) m/z 332 (M+).

EXAMPLE 50

The Preparation of 2-fluoro-5-((6-fluoropyridin-2-yl)ethynyl)-N-(pyridin-3-yl)benzamide (ZD081)

2-ethynylpyridine was replaced by 2-ethynyl-6-fluoropyridine, 4-fluoroaniline was replaced by 3-aminopyridine, while the remaining raw materials, reagents and the preparation method were the same as those in Example 1 to give the product ZD081, yield 80%. $^1$H NMR (400 MHz, CDCl$_3$) δ7.660 (1H, dd), 7.723 (1H, dd), 7.396 (1H, dd), 8.605 (1H, dd), 7.784 (1H, dd), 7.571 (1H, dd), 8.402 (1H, ddd), 7.474 (1H, ddd), 7.315 (1H, ddd), 8.404 (1H, ddd). LRMS (EI) m/z 336 (M+).

EXAMPLE 51

The Preparation of 5-((6-chloropyridin-2-yl)ethynyl)-2-fluoro-N-(pyridin-3-yl)benzamide (ZD082)

2-ethynylpyridine was replaced by 2-ethynyl-6-chloropyridine, 4-fluoroaniline was replaced by 3-aminopyridine, while the remaining raw materials, reagents and the preparation method were the same as those in Example 1 to give the product ZD082, yield 80%. $^1$H NMR (400 MHz, CDCl$_3$) δ7.455 (1H, dd), 7.718 (1H, dd), 7.426 (1H, dd), 8.604 (1H, dd), 7.780 (1H, dd), 7.572 (1H, dd), 8.402 (1H, ddd), 7.474 (1H, ddd), 7.315 (1H, ddd), 8.404 (1H, ddd). LRMS (EI) m/z 353 (M+).

EXAMPLE 52

The Preparation of 2-fluoro-N-(pyridin-3-yl)-5-((6-(trifluoromethyl)pyridn-2-yl) ethynyl) benzamide (ZD083)

2-ethynylpyridine was replaced by 2-ethynyl-6-trifluoromethylpyridine, 4-fluoroaniline was replaced by 3-aminopyridine, while the remaining raw materials, reagents and the preparation method were the same as those in Example 1 to give the product ZD083, yield 80%. $^1$H NMR (400 MHz, CDCl$_3$) δ7.572 (1H, dd), 8.615 (1H, dd), 7.961 (1H, dd), 8.402 (1H, ddd), 7.474 (1H, ddd), 7.315 (1H, ddd), 8.404 (1H, ddd), 7.331 (1H, dd), 7.916 (1H, dd), 7.346 (1H, dd). LRMS (EI) m/z 386 (M+).

EXAMPLE 53

The Preparation of 5-((6-cyanopyridin-2-ylethynyl)-2-fluoro-N-(pyridin-3-yl)benzamide (ZD084)

2-ethynylpyridine was replaced by 2-ethynyl-6-cyanopyridine, 4-fluoroaniline was replaced by 3-aminopyridine, while the remaining raw materials, reagents and the preparation method were the same as those in Example 1 to give the product ZD084, yield 80%. $^1$H NMR (400 MHz, CDCl$_3$) δ7.575 (1H, dd), 8.647 (1H, dd), 7.783 (1H, dd), 8.402 (1H, ddd), 7.474 (1H, ddd), 7.315 (1H, ddd), 8.404 (1H, ddd), 7.507 (1H, dd), 7.892 (1H, dd), 7.780 (1H, dd). LRMS (EI) m/z 343 (M+).

EXAMPLE 54

The Preparation of 2-fluoro-N-(pyridin-3-yl)-5-(pyrimidin-5-ylethynyl) benzamide (ZD085)

2-ethynylpyridine was replaced by 5-ethynylpyrimidine, 4-fluoroaniline was replaced by 3-aminopyridine, while the remaining raw materials, reagents and the preparation method were the same as those in Example 1 to give the product ZD085, yield 80%. $^1$H NMR (400 MHz, CDCl$_3$) δ7.645 (1H, dd), 8.552 (1H, dd), 7.859 (1H, dd), 8.402 (1H, ddd), 7.474 (1H, ddd), 7.315 (1H, ddd), 8.404 (1H, ddd), 9.058 (1H, dd), 8.767 (1H, dd), 8.849 (1H, dd). LRMS (EI) m/z 319 (M+).

EXAMPLE 55

The Preparation of 2-fluoro-5-((2-methylpyrimidin-5-yl)ethynyl)-N-(pyridin-3-yl)benzamide (ZD086)

2-ethynylpyridine was replaced by 2-methyl-5-ethynylpyrimidine, 4-fluoroaniline was replaced by 3-aminopyridine, while the remaining raw materials, reagents and the preparation method were the same as those in Example 1 to give the product ZD086, yield 80%. $^1$H NMR (400 MHz, CDCl$_3$) δ7.640 (1H, dd), 8.552 (1H, dd), 7.859 (1H, dd), 8.402 (1H, ddd), 7.474 (1H, ddd), 7.315 (1H, ddd), 8.404 (1H, ddd), 8.751 (1H, d), 8.726 (1H, d), 2.603 (s, 3H). LRMS (EI) m/z 333 (M+).

EXAMPLE 56

The Preparation of 2-fluoro-N-(4-fluorophenyl)-5-((2-methylpyrimidin-5-yl)ethynyl) benzamide (ZD087)

2-ethynylpyridine was replaced by 2-methyl-5-ethynylpyrimidine, while the remaining raw materials, reagents and the preparation method were the same as those in Example 1 to give the product ZD087, yield 80%. $^1$H NMR (400 MHz, CDCl$_3$) δ7.640 (1H, dd), 8.552 (1H, dd), 7.859 (1H, dd), 7.741 (1H, ddd), 7.741 (1H, ddd), 7.017 (1H, ddd), 7.018 (1H, ddd), 8.751 (1H, d), 8.726 (1H, d), 2.603 (s, 3H). LRMS (EI) m/z 350 (M+).

EXAMPLE 57

The Preparation of (3,4-dihydro-isoquinolin-2(1H)-yl)(2-fluoro-5-((2-methylpyrimidin-5-yl)ethynyl)phenyl methanone (ZD088)

2-ethynylpyridine was replaced by 2-methyl-5-ethynylpyrimidine, 4-fluoroaniline was replaced by 3,4-dihydroisoquinoline, while the remaining raw materials, reagents and the preparation method were the same as those in Example 1 to give the product ZD088, yield 80%. $^1$H NMR (400 MHz, CDCl$_3$) δ7.614 (1H, dd), 8.513 (1H, dd), 7.856 (1H, dd), 4.270 (1H, d), 4.461 (1H, d), 3.652 (1H, ddd), 3.376 (1H, ddd), 2.927 (1H, ddd), 3.020 (1H, ddd), 6.867 (1H, ddd), 7.240 (1H, ddd), 7.042 (1H, ddd), 8.751 (1H, d), 8.727 (1H, d), 7.168 (1H, ddd), 2.603 (s, 3H). LRMS (EI) m/z 372 (M+).

EXAMPLE 58

The Preparation of 2-fluoro-5-((2-methyloxazol-4-yl)ethynyl)-N-(pyridin-3-yl)benzamide (ZD089)

2-ethynylpyridine was replaced by 2-methyl-4-ethynyloxazole, 4-fluoroaniline was replaced by 3-aminopyridine, while the remaining raw materials, reagents and the preparation method were the same as those in Example 1 to give the product ZD086, yield 80%. $^1$H NMR (400 MHz, CDCl$_3$) δ7.392 (1H, dd), 8.492 (1H, dd), 7.892 (1H, dd), 8.402 (1H, ddd), 7.474 (1H, ddd), 7.315 (1H, ddd), 8.404 (1H, ddd), 7.383 (s, 1H), 2.547 (s, 3H). LRMS (EI) m/z 322 (M+).

EXAMPLE 59

The Preparation of 2-fluoro-N-(4-fluorophenyl)-5-((2-methyloxazol-4-yl) ethynyl) benzamide (ZD090)

2-ethynylpyridine was replaced by 2-methyl-4-ethynyloxazole, while the remaining raw materials, reagents and the preparation method were the same as those in Example 1 to give the product ZD090, yield 80%. $^1$H NMR (400 MHz, CDCl$_3$) δ7.393 (1H, dd), 8.492 (1H, dd), 7.892 (1H, dd), 7.741 (1H, ddd), 7.741 (1H, ddd), 7.017 (1H, ddd), 7.018 (1H, ddd), 7.383 (s, 1H), 2.547 (s, 3H). LRMS (EI) m/z 339 (M+).

EXAMPLE 60

The Preparation of (3,4-dihydro-isoquinolin-2(1H)-yl)(2-fluoro-5-((2-methyloxazol-4-yl)ethynyl)phenyl)methanone (ZD091)

2-ethynylpyridine was replaced by 2-methyl-4-ethynyloxazole, 4-fluoroaniline was replaced by 3,4-dihydroisoquinoline, while the remaining raw materials, reagents and the preparation method were the same as those in Example 1 to give the product ZD091, yield 80%. $^1$H NMR (400 MHz, CDCl$_3$) δ7.390 (1H, dd), 8.481 (1H, dd), 7.847 (1H, dd), 4.269 (1H, d), 4.460 (1H, d), 3.651 (1H, ddd), 3.353 (1H, ddd), 2.927 (1H, ddd), 3.034 (1H, ddd), 6.867 (1H, ddd), 7.240 (1H, ddd), 7.042 (1H, ddd), 7.382 (1H), 7.168 (1H, ddd), 2.547 (s, 3H). LRMS (EI) m/z 361 (M+).

EXAMPLE 61

The Preparation of (3,4-dihydro-isoquinolin-2(1H)-yl)(5-((3,5-dimethyl-isoxazol-4-yl)ethynyl)-2-fluoro-phenyl)methanone (ZD092)

2-ethynylpyridine was replaced by 3,5-dimethyl-4-ethynylisoxazole, 4-fluoroaniline was replaced by 3,4-dihydroisoquinoline, while the remaining raw materials, reagents and the preparation method were the same as those in Example 1 to give the product ZD092, yield 80%. $^1$H NMR (400 MHz, CDCl$_3$) δ7.380 (1H, dd), 8.483 (1H, dd), 7.895 (1H, dd), 4.269 (1H, d), 4.460 (1H, d), 3.652 (1H, ddd), 3.375 (1H, ddd), 2.927 (1H, ddd), 3.020 (1H, ddd), 6.867 (1H, ddd), 7.240 (1H, ddd), 7.042 (1H, ddd), 7.168 (1H, ddd), 2.546 (s, 3H), 2.234 (s, 3H). LRMS (EI) m/z 375 (M+).

EXAMPLE 62

The Preparation of 5-((3,5-dimethylisoxazol-4-yl)ethynyl)-2-fluoro-N-(pyridin-3-yl)benzamide (ZD093)

2-ethynylpyridine was replaced by 3,5-dimethyl-4-ethynylisoxazole, 4-fluoroaniline was replaced by 3-aminopyridine, while the remaining raw materials, reagents and the preparation method were the same as those in Example 1 to give the product ZD093, yield 80%. $^1$H NMR (400 MHz, CDCl$_3$) δ7.382 (1H, dd), 8.495 (1H, dd), 7.899 (1H, dd), 8.402 (1H, ddd), 7.474 (1H, ddd), 7.315 (1H, ddd), 8.404 (1H, ddd), 2.546 (s, 3H), 2.234 (s, 3H). LRMS (EI) m/z 336 (M+).

EXAMPLE 63

The Preparation of 5-((3,5-dimethylisoxazol-4-yl)ethynyl)-2-fluoro-N-(4-fluorophenyl)benzamide (ZD094)

2-ethynylpyridine was replaced by 3,5-dimethyl-4-ethynylisoxazole, while the remaining raw materials, reagents and the preparation method were the same as those in Example 1 to give the product ZD094, yield 80%. $^1$H NMR (400 MHz, CDCl$_3$) δ7.383 (1H, dd), 8.494 (1H, dd), 7.899 (1H, dd, J=8.455), 7.741 (1H, ddd), 7.741 (1H, ddd), 7.017 (1H, ddd), 7.018 (1H, ddd), 2.546 (s, 3H), 2.234 (s, 3H). LRMS (EI) m/z 353 (M+).

EXAMPLE 64

The Preparation of N-(4-fluorophenyl)-3-((2-methylthiazol-4-yl)ethynyl)benzamide (ZD009)

2-ethynylpyridine was replaced by 4-ethynyl-2-methylthiazole, 2-fluoro-5-iodobenzoic acid was replaced by 3-iodobenzoic acid, while the remaining raw materials, reagents and the preparation method were the same as those in Example 1 to give the product ZD009, yield 80%. $^1$H NMR (400 MHz, DMSO) δ 10.41 (s, 1H), 8.16 (s, 1H), 8.02-7.95 (m, 2H), 7.79 (m, J=10.9, 8.1, 6.4 Hz, 3H), 7.61 (t, J=7.8 Hz, 1H), 7.20 (dd, J=12.3, 5.5 Hz, 2H), 2.69 (s, 3H). LRMS (EI) m/z 336 (M+)

EXAMPLE 65

The Preparation of (3,4-dihydro-isoquinolin-2(1H)-yl)(3-((2-methylthiazol-4-yl)ethynyl)phenyl)methanone (ZD012)

2-ethynylpyridine was replaced by 4-ethynyl-2-methylthiazole, 2-fluoro-5-iodobenzoic acid was replaced by 3-iodobenzoic acid, 4-fluoroaniline was replaced by 3,4-dihydroisoquinoline, while the remaining raw materials, reagents and the preparation method were the same as those in Example 1 to give the product ZD012, yield 80%. $^1$H NMR (400 MHz, CDCl3) δ 7.61 (m J=4.0, 1.6 Hz, 2H), 7.42 (d, J=6.8 Hz, 2H), 7.38 (d, J=3.2 Hz, 1H), 7.24-7.12 (m, 4H), 4.74 (d, J=123.5 Hz, 2H), 3.81 (d, J=140.1 Hz, 2H), 2.93 (d, J=36.6 Hz, 2H), 2.74 (s, 3H). LRMS (EI) m/z 358 (M+)

EXAMPLE 66

The Preparation of 3-((2-methylthiazol-4-ylethynyl)-N-(pyridin-3-yl)benzamide (ZD013)

2-ethynylpyridine was replaced by 4-ethynyl-2-methylthiazole, 2-fluoro-5-iodobenzoic acid was replaced by 3-iodobenzoic acid, 4-fluoroaniline was replaced by 3-aminopyridine, while the remaining raw materials, reagents and the preparation method were the same as those in Example 1 to give the product ZD013, yield 80%. $^1$H NMR (400 MHz, DMSO) δ 10.56 (s, 1H), 8.94 (s, 1H), 8.33 (d, J=4.0 Hz, 1H), 8.21 (d, J=11.1 Hz, 2H), 8.02 (d, J=7.8 Hz, 1H), 7.97 (s, 1H), 7.79 (d, J=7.7 Hz, 1H), 7.63 (t, J=7.7 Hz, 1H), 7.41 (dd, J=8.2, 4.7 Hz, 1H), 2.69 (s, 3H). LRMS (EI) m/z 319 (M+)

EXAMPLE 67

The Preparation of 3-((2-methylthiazol-4-yl)ethynyl)-N-phenylbenzamide (ZZD014)

2-ethynylpyridine was replaced by 4-ethynyl-2-methylthiazole, 2-fluoro-5-iodobenzoic acid was replaced by 3-iodobenzoic acid, 4-fluoroaniline was replaced by aniline, while the remaining raw materials, reagents and the preparation method were the same as those in Example 1 to give the product ZD014, yield 80%. $^1$H NMR (400 MHz, DMSO) δ 10.36 (s, 1H), 8.17 (s, 1H), 7.99 (dd, J=5.3, 4.2 Hz, 1H), 7.97 (s, 1H), 7.78 (dd, J=12.4, 4.4 Hz, 3H), 7.61 (t, J=7.8 Hz, 1H), 7.36 (t, J=7.9 Hz, 2H), 7.12 (t, J=7.4 Hz, 1H), 2.72-2.65 (m, 3H). LRMS (EI) m/z 318 (M+)

EXAMPLE 68

The Preparation of (3-(2-methylthiazol-4-yl)ethynyl) phenyl)(3-trifluoromethyl-5,6-dihydro-[1,2,4] triazolo [4,3-a]pyrazin-7(8H)-yl)methanone (ZD005)

2-fluoro-5-iodobenzoic acid was replaced by 3-iodobenzoic acid, 4-fluoroaniline was replaced by 3-trifluoromethyl-5,6,7,8-tetrahydro-[1,2,4]triazolo[4,3-a]pyrazine, 2-ethynylpyridine was replaced by 4-ethynyl-2-methylthiazole, while the remaining raw materials, reagents and the preparation method were the same as those in Example 1 to give the product ZD005, yield 80%. $^1$H NMR (400 MHz, CDCl$_3$) δ 7.68 (s, 1H), 7.65 (s, 1H), 7.47 (d, J=5.6 Hz, 2H), 7.41 (s, 1H), 5.06 (s, 2H), 4.26 (s, 2H), 4.12 (s, 2H), 2.74 (s, 3H). LRMS (EI) m/z 418 (M+).

EXAMPLE 69

The Preparation of 5-((1H-indazol-5-yl)ethynyl)-2-fluoro-N-(4-fluorophenyl)benzamide (ZD006)

2-ethynylpyridine was replaced by 5-ethynyl-1H-indazole, while the remaining raw materials, reagents and the preparation method were the same as those in Example 1 to give the product ZD006, yield 80%. $^1$H NMR (400 MHz, DMSO) δ 13.31 (s, 1H), 10.58 (s, 1H), 8.14 (s, 1H), 8.04 (s, 1H), 7.86 (dd, J=6.7, 2.2 Hz, 1H), 7.79-7.72 (m, 3H), 7.60 (d, J=8.6 Hz, 1H), 7.53-7.48 (m, 1H), 7.47-7.40 (m, 1H), 7.21 (dd, J=12.2, 5.6 Hz, 2H). LRMS (EI) m/z 374 (M+).

EXAMPLE 70

The Preparation of (3-((2-methylthiazol-4-yl)ethynyl)phenyl)(7-oxa-2-azaspiro[3.5]nonan-2-yl) methanone (ZD007)

2-fluoro-5-iodobenzoic acid was replaced by 3-iodobenzoic acid, 4-fluoroaniline was replaced by 7-oxa-2-azaspiro [3.5]nonane, 2-ethynylpyridine was replaced by 4-ethynyl-2-methylthiazole, while the remaining raw materials, reagents and the preparation method were the same as those in Example 1 to give the product ZD007, yield 80%. $^1$H NMR (400 MHz, DMSO) δ 7.95 (s, 1H), 7.77 (s, 2H), 7.52 (t, J=7.7 Hz, 2H), 4.08 (s, 4H), 3.79 (t, 4H), 2.68 (s, 3H), 1.71 (s, 4H). LRMS (EI) m/z 353 (M+)

EXAMPLE 71

The Preparation of (3-((2-methylthiazol-4-yl)ethynyl)phenyl)(8-oxa-2-azaspiro [4.5]dec-2-yl) methanone (ZD008)

2-fluoro-5-iodobenzoic acid was replaced by 3-iodobenzoic acid, 4-fluoroaniline was replaced by 8-oxa-2-azaspiro [4.5]decane, 2-ethynylpyridine was replaced by 4-ethynyl-2-methylthiazole, while the remaining raw materials, reagents and the preparation method were the same as those in Example 1 to give the product ZD008, yield 80%. $^1$H NMR (400 MHz, CDCl$_3$) δ 7.65 (s, 1H), 7.60 (t, J=7.2 Hz, 1H), 7.51-7.46 (m, 1H), 7.39 (m, J=7.2, 4.2 Hz, 2H), 3.80-3.61 (m, 4H), 3.60-3.45 (m, 4H), 2.73 (s, 3H), 1.69-1.43 (m, 6H). LRMS (EI) m/z 367 (M+)

EXAMPLE 72

The Preparation of N-(4-cyanophenyl)-3-((2-methylthiazol-4-yl) ethynyl) benzamide (ZD010)

2-fluoro-5-iodobenzoic acid was replaced by 3-iodobenzoic acid, 4-fluoroaniline was replaced by 4-cyanoaniline, 2-ethynylpyridine was replaced by 4-ethynyl-2-methylthiazole, while the remaining raw materials, reagents and the preparation method were the same as those in Example 1 to give the product ZD010, yield 80%. $^1$H NMR (400 MHz, DMSO) δ 10.74 (s, 1H), 8.17 (s, 1H), 7.99 (t, J=9.4 Hz, 4H), 7.82 (dd, J=15.8, 8.2 Hz, 3H), 7.61 (dd, J=20.0, 12.4 Hz, 1H), 2.69 (s, 3H). LRMS (EI) m/z 344 (M+)

EXAMPLE 73

The Preparation of (1-methyl-3,4-dihydro-isoquinolin-2(1H)-yl)(3-((2-methylthiazol-4-yl)ethynyl)phenyl)methanone (ZD011)

2-fluoro-5-iodobenzoic acid was replaced with 3-iodobenzoic acid, 4-fluoroaniline was replaced by 1-methyl-3,4-dihydroisoquinoline, 2-ethynylpyridine was replaced by 4-ethynyl-2-methylthiazole, while the remaining raw materials, reagents and the preparation method were the same as those in Example 1 to give the product ZD011, yield 80%. $^1$H NMR (400 MHz, CDCl$_3$) δ 7.64-7.53 (m, 2H), 7.39 (d, J=7.5 Hz, 3H), 7.24-7.06 (m, 4H), 5.77 (d, J=6.0 Hz, 1H), 4.81 (s, 1H), 3.75 (s, 1H), 3.53-2.90 (m, 2H), 2.74 (s, 3H), 1.70-1.53 (m, 3H). LRMS (EI) m/z 373 (M+)

EXAMPLE 74

The Synthesis of 3-((2-methylthiazol-4-yl)ethynyl)-N-(4-(trifluoromethyl)phenyl)benzamide (ZD015)

2-fluoro-5-iodobenzoic acid was replaced by 3-iodobenzoic acid, 4-fluoroaniline was replaced by 4-trifluoromethylaniline, 2-ethynylpyridine was replaced by 4-ethynyl-2-methylthiazole, while the remaining raw materials, reagents and the preparation method were the same as those in Example 1 to give the product ZD015, yield 80%. $^1$H NMR (400 MHz, DMSO) δ 10.68 (s, 1H), 8.18 (s, 1H), 8.02 (t, J=6.3 Hz, 3H), 7.97 (s, 1H), 7.79 (d, J=7.7 Hz, 1H), 7.74 (d, J=8.6 Hz, 2H), 7.63 (t, J=7.8 Hz, 1H), 2.69 (s, 3H). LRMS (EI) m/z 387 (M+)

EXAMPLE 75

The Preparation of N-(3-fluorophenyl)-3-((2-methylthiazol-4-yl)ethynyl)benzamide (ZD017)

2-fluoro-5-iodobenzoic acid was replaced by 3-iodobenzoic acid, 4-fluoroaniline was replaced by 3-fluoroaniline, 2-ethynylpyridine was replaced by 4-ethynyl-2-methylthiazole, while the remaining raw materials, reagents and the preparation method were the same as those in Example 1 to give the product ZD017, yield 80%. $^1$H NMR (400 MHz, CDCl$_3$) δ 8.05 (s, 1H), 7.87 (dd, J=7.9, 1.3 Hz, 1H), 7.72-7.65 (min, 2H), 7.48 (t, J=7.8 Hz, 1H), 7.41 (s, 1H), 7.32-7.30 (m, 1H), 6.85 (m, J=9.5 Hz, 2H), 6.69 (s, 1H), 2.76 (s, 3H). LRMS (EI) m/z 337 (M+)

EXAMPLE 76

The Preparation of N-(3-cyanophenyl)-3-((2-methylthiazol-4-yl)ethynyl) benzamide (ZD019)

2-fluoro-5-iodobenzoic acid was replaced by 3-iodobenzoic acid, 4-fluoroaniline was replaced by 3-cyanoaniline, 2-ethynylpyridine was replaced by 4-ethynyl-2-methylthiazole, while the remaining raw materials, reagents and the preparation method were the same as those in Example 1 to give the product ZD019, yield 80%. $^1$H NMR (400 MHz, DMSO) δ 10.66 (s, 1H), 8.26 (d, J=1.1 Hz, 1H), 8.18 (d, J=1.5 Hz, 1H), 8.06 (m, J=6.0, 3.6, 2.2 Hz, 1H), 8.03-7.99 (m, 1H), 7.97 (s, 1H), 7.82-7.77 (m, 1H), 7.66-7.57 (m, 3H), 2.69 (s, 3H). LRMS (EI) m/z 344 (M+)

Pharmacological Activity Test Example

EXAMPLE 1

Physical and Chemical Properties of the Compound

TABLE 1

Parameters of the physicochemical properties of the compounds

| No. | LogP | CLogP | tPSA |
|---|---|---|---|
| ZD001 | 4.18 | 3.99516 | 41.46 |
| ZD002 | 3.04 | 2.2036 | 41.9 |
| ZD003 | 3.32 | 2.7626 | 41.9 |
| ZD004 | 4.93 | 4.33516 | 41.46 |
| ZD005 | 4.19 | 2.18697 | 60.63 |
| ZD006 | 4.25 | 4.97516 | 53.49 |
| ZD007 | 3.23 | 1.755 | 41.9 |
| ZD008 | 3.51 | 2.314 | 41.9 |
| ZD009 | 4.77 | 4.5316 | 41.46 |
| ZD010 | 4.65 | 4.162 | 65.25 |
| ZD011 | 5.22 | 5.08 | 32.67 |
| ZD012 | 4.9 | 4.561 | 32.67 |
| ZD013 | 3.28 | 3.462 | 53.82 |
| ZD014 | 4.61 | 4.131 | 41.46 |
| ZD015 | 5.54 | 5.4648 | 41.46 |
| ZD017 | 4.77 | 4.5316 | 41.46 |
| ZD019 | 4.65 | 4.162 | 65.25 |
| ZD036 | 4.58 | 4.14516 | 41.46 |
| ZD037 | 5.33 | 4.48516 | 41.46 |
| ZD038 | 3.76 | 3.99516 | 41.46 |
| ZD039 | 3.76 | 3.99516 | 41.46 |
| ZD040 | 4.51 | 4.3506 | 41.46 |
| ZD041 | 5.26 | 4.6906 | 41.46 |
| ZD042 | 2.69 | 2.92556 | 53.82 |
| ZD043 | 3.44 | 3.26556 | 53.82 |
| ZD044 | 4.06 | 3.62556 | 65.25 |
| ZD045 | 4.81 | 3.96556 | 65.25 |
| ZD046 | 4.31 | 4.4396 | 32.67 |
| ZD047 | 5.06 | 4.7796 | 32.67 |
| ZD048 | 4.63 | 4.9586 | 32.67 |
| ZD049 | 5.37 | 5.2986 | 32.67 |
| ZD050 | 2.57 | 2.05432 | 66.18 |
| ZD051 | 3.31 | 3.03768 | 53.82 |
| ZD052 | 4.19 | 3.64034 | 45.03 |
| ZD053 | 4.06 | 3.37768 | 53.82 |
| ZD054 | 4.34 | 3.52768 | 53.82 |
| ZD055 | 1.82 | 1.71432 | 66.18 |
| ZD056 | 3.44 | 3.30034 | 45.03 |
| ZD057 | 4.77 | 4.0656 | 41.46 |
| ZD058 | 3.31 | 3.0588 | 77.61 |
| ZD059 | 4.2 | 3.25848 | 53.82 |
| ZD060 | 5.69 | 4.38996 | 41.46 |
| ZD061 | 4.81 | 4.26516 | 65.25 |
| ZD062 | 4.93 | 4.1695 | 56.46 |
| ZD063 | 5.82 | 5.5763 | 32.67 |
| ZD064 | 4.93 | 3.73516 | 41.46 |
| ZD065 | 4.93 | 4.33516 | 41.46 |
| ZD066 | 5.09 | 4.45246 | 41.46 |
| ZD067 | 5.09 | 3.92246 | 41.46 |
| ZD068 | 5.33 | 4.90516 | 41.46 |
| ZD069 | 5.69 | 5.26836 | 41.46 |
| ZD070 | 4.65 | 4.03934 | 50.69 |
| ZD071 | 4.15 | 3.26556 | 53.82 |
| ZD072 | 3.44 | 3.26556 | 53.82 |
| ZD073 | 4.06 | 3.47806 | 53.82 |
| ZD074 | 4.34 | 4.04806 | 53.82 |
| ZD075 | 5.26 | 4.5646 | 41.46 |

TABLE 1-continued

Parameters of the physicochemical properties of the compounds

| No. | LogP | CLogP | tPSA |
|---|---|---|---|
| ZD076 | 2.76 | 2.76656 | 53.82 |
| ZD077 | 3.66 | 2.95897 | 53.82 |
| ZD078 | 3.93 | 3.52897 | 53.82 |
| ZD079 | 4.34 | 3.76528 | 53.82 |
| ZD080 | 3.39 | 3.42456 | 53.82 |
| ZD081 | 3.31 | 3.15256 | 53.82 |
| ZD082 | 3.59 | 3.72256 | 53.82 |
| ZD083 | 4.03 | 3.95556 | 53.82 |
| ZD084 | 3.15 | 2.75356 | 77.61 |
| ZD085 | 1.67 | 1.96856 | 66.18 |
| ZD086 | 2.58 | 2.46756 | 66.18 |
| ZD087 | 4.07 | 3.53716 | 53.82 |
| ZD088 | 4.2 | 3.9816 | 45.03 |
| ZD089 | 2.07 | 2.37056 | 63.05 |
| ZD090 | 3.56 | 3.44016 | 50.69 |
| ZD091 | 3.69 | 3.8846 | 41.9 |
| ZD092 | 4.44 | 4.4536 | 41.9 |
| ZD093 | 2.82 | 2.93956 | 63.05 |
| ZD094 | 4.31 | 4.00916 | 50.69 |
| MPEP | 3.77 | 3.782 | 12.36 |
| CTEP | 5.7 | 5.70617 | 37.19 |

Note:
The physical and chemical properties of the compounds (LogP, CLogP and tPSA values) are Chemdraw software predictions in the ChemOffice package.

The results show that the physical and chemical properties of these compounds (Log P, C Log P and tPSA, etc.) are comparable to those of the positive drugs, thus leading to good druggability.

EXAMPLE 2

In Vitro Activity Test for mGluR5

Experimental material: HEK293/mGluR5 cell line, Fluo-8 calcium ion fluorescent dye, positive control MPEP, CTEP Experimental instrument: FLIPR Tetra real-time fluorescence imaging analysis system Experimental method: HDB Fluo-8 calcium fluorescence detection method Experimental principle: HDB Fluo-8 calcium ion fluorescence detection method is a fast, simple and reliable fluorescence detection method of intracellular calcium concentration changes. The Fluo 8-AM fluorescent dye is an acetyl methyl ester derivative of Fluo 8 which can easily penetrate the cell membrane into the cell by culture. The fluorescent dye into the cell will be hydrolyzed by intracellular esterase, the resulting Fluo 8 cannot easily pass through the lipid bimolecular membrane as a polar molecule, and will retain in the cell, and combine with calcium ($Ca^{2+}$) to produce fluoresces.

Cells expressing GPCR receptor protein (mGluR5) were first calibrated with a calcium ion sensitive fluorescent probe and then stimulated with the compound. After stimulation, the activation of the receptor lead to the calcium ion mobilization, and the fluorescent probe captures the calcium ion to induce the fluorescence signal. The signal can be read by a fluorescent plate reader. The fluorescent plate reader contains a sampling head for compound addition, thus enabling the change of the fluorescence value of the compound be read in real time. If the selected compound can activate mGluR5, the calcium flow reaction can be greatly increased; conversely, if the selected compound is able to antagonize mGluR5, the calcium flow reaction can be greatly reduced. Experimental results:

TABLE 2

Inhibitory effects of compounds on mGluR5

| No. | mGluR5 $IC_{50}$ |
|---|---|
| ZD001 | 13.9 nM |
| ZD004 | 11 nM |
| ZD036 | 20.29 nM |
| ZD037 | 7.312 nM |
| ZD039 | 382 nM |
| ZD040 | 104.1 nM |
| ZD041 | 108.5 nM |
| ZD042 | 19.4 nM |
| ZD043 | 5.601 nM |
| ZD044 | 86.53 nM |
| ZD045 | 53.53 nM |
| ZD046 | 15.15 nM |
| ZD047 | 6.647 nM |
| ZD048 | 71.32 nM |
| ZD049 | 37.99 nM |
| ZD009 | 40.6 nM |
| ZD012 | 14.4 nM |
| ZD010 | 86.6 nM |
| ZD011 | 32.56 nM |
| ZD013 | 14.2 nM |
| ZD014 | 14.8 nM |
| ZD017 | 133 nM |
| ZD019 | 134 nM |
| CTEP | 539 nM |
| MPEP | 4 nM |

The structures of positive compounds are as follows:

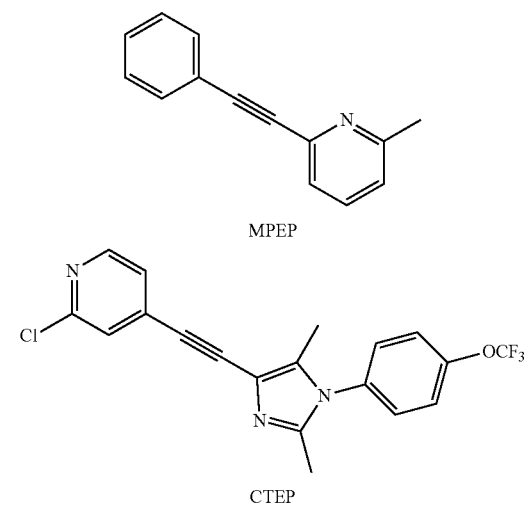

Experimental results: In the bioactivity evaluation, we use the tool molecule MPEP as positive control, of which the $IC_{50}$ value is 4 nM. From the data already obtained in the above table, it can be seen that the $IC_{50}$ values of some of the newly synthesized compound are comparable to that of the positive control compound, and the $IC_{50}$ values to mGluR5 of several compounds are less than 10 nM, which show good inhibitory effect on mGluR5.

EXAMPLE 3 mGluR5/1 Selectivity Test

Experimental material: HEK293/mGluR5 cell line, HEK293/mGluR1 cell line, Fluo-8 calcium ion fluorescent dye, positive control JNJ16259685

Compounds with better mGluR5 $IC_{50}$ were used in selectivity test, the results are shown in Table 3:

TABLE 3 mGluR5/1 selectivity test results

| No. | mGluR5 IC$_{50}$ | mGluR1 IC$_{50}$ | mGluR5/mGluR1 |
|---|---|---|---|
| ZD001 | 13.9 nM | >100 μM | >7194 |
| ZD004 | 11 nM | >100 μM | >9091 |
| ZD012 | 14.4 nM | >100 μM | >6944 |
| ZD013 | 14.2 nM | >100 μM | >7042 |
| ZD014 | 14.8 nM | >100 μM | >6757 |
| ZD016 | 29.2 nM | >100 μM | >3425 |
| ZD036 | 20.29 nM | >100 μM | >4929 |
| ZD037 | 7.312 nM | >100 μM | >13676 |
| ZD042 | 19.4 nM | >100 μM | >5155 |
| ZD043 | 5.601 nM | >100 μM | >17854 |
| ZD046 | 15.15 nM | >100 μM | >6601 |
| ZD047 | 6.647 nM | >100 μM | >15044 |
| ZD049 | 37.99 nM | >100 μM | >2632 |
| JNJ16259685 | — | 91.23 nM | — |

Conclusion: Most of these compounds have weak inhibitory effect on mGluR1 which is of high homology to mGluR5 (almost no inhibitory effect), indicating that these compounds have good selectivity and high specificity.

EXAMPLE 4

Animal In Vivo Activity Test

Experimental principle: Fragile X chromosome syndrome is common genetic disease by mutations during X chromosome formation in the human body, and is the most common genetic cause of autism and mental retardation. The main clinical manifestations include moderate and severe mental retardation, such as lacking of learning ability, cognitive disorder and epilepsy susceptibility. Although it has been confirmed that the pathogenic gene is Fmr1 gene, so far there is no effective intervention and treatment in clinical therapy.

Inserting a neomycin fragment in the Fmr1 gene region to prevent the gene to express FMRP can produce a mouse model of fragile X syndrome. Many behavioral manifestations of Fmr1 knockout mice are very similar to those of fragile X syndrome patients, most notably the increased spontaneous activity, decreased open field habit ability, increased susceptibility to the audiogenic seizures, and a slight lack of learning ability.

In this study, we used audiogenic epilepsy induced animal model of Fmr1 knockout mice, and evaluated the efficacy of compound ZD043 with epilepsy seizure latency, seizure level and epileptic mortality as evaluation indexes.

Laboratory Animals and Breeding:
Species, strain: Fmr1 knockout mice, FVB.129P2-Pde6b$^+$ Tyr$^{c-ch}$ Fmr1$^{tm1Cgr}$/J (strain number 004624)
Age: 19-21 days
Weight: about 7-10 g
Gender: female and male
Number of animal: 24
Feeding conditions: SPF class animal room of Institute of Biological Sciences, Chinese Academy of Sciences, temperature: 22-24° C., humidity: 50-70%, light: 150-300 Lx, 12 hours alternating day and night (7:00-19:00 daytime).

Test reagent and preparation method: before the experiment, 2.0 mg ZD043 was weighed in 2 mL centrifuge tube, 10 uL DMSO was taken with a precise pipette to dissolve ZD043 powder, then 10 uL Tween80 was added, mixed and 980 uL of saline was added, well mixed to form a suspension liquid.

Solvent control: 0.9% NaCl solution containing 1% DMSO, 1% Tween 80

The main experimental equipment: cylindrical transparent organic glass bucket (diameter 10 cm, 25 cm high)

Video surveillance system: Shanghai Panorama Digital Technology Co., Ltd., Model: IPC-5201-BNS High-decibel siren loudspeaker (≥120 dB): AIDEXIN company, model: ES626

Decibel Tester: Tektronix Electronic Instrument Holdings Limited, Model: TM824

Methods: The mice were weighed on the day of the experiment. The mice were injected intraperitoneally into 19 to 22 days Fmr1 knockout mice respectively according to the experimental design group 30 minutes before the convulsive test. The mice to be tested were transferred to a sonic seizure test laboratory, placed in a transparent organic glass bucket, and a high-decibel siren loudspeaker was fixed on the top of organic glass bucket. Before delivering the stimulate sound, the mouse was allowed to explore freely for 1 minute, then turn on the loudspeaker, video recorded for the whole process by surveillance system, sound stimulated (≥120 dB) for 3 minutes, or stop after the animal was died, and the experiment was ended.

Test method: After the end of the experiment, the epilepsy seizure latency (2 grade appearance was regarded as seizures, and the longest latency period was recorded as 300 seconds if no epilepsy was observed) and seizure level (Level 0: no epileptic response; Level 1: rapid running and continuous jump; Level 2: paroxysmal epilepsy; Level 3: tonic epilepsy; Level 4: death) were analyzed according to video record.

Data processing: calculate the mean and standard error of the epilepsy seizure latency and seizure level as well as the percentage of epilepsy death of each group.

The shorter the latency of epilepsy, the higher the incidence level, indicating that the more likely to induce epilepsy, while prolonged latency after drug intervention and a decrease in epilepsy level indicate that the compound can inhibit the occurrence of epilepsy or reduce the degree of epilepsy.

After the end of the experiment, the epilepsy seizure latency (2 grade appearance was regarded as seizures, and the longest latency period was recorded as 300 seconds if no epilepsy was observed) and seizure level (Level 0: no epileptic response; Level 1: rapid running and continuous jump; Level 2: paroxysmal epilepsy; Level 3: tonic epilepsy; Level 4: death) were analyzed according to video record.

Experimental Results:

TABLE 4

Experimental results of ZD043 interfering audiogenic epilepsy in Fmr1 knockout mice

| ID | Drug (mg/kg) | Latency (s) | Seizure level | Mortality (%) |
|---|---|---|---|---|
| 1 | Veh | 37.8 | 4 | 100 |
| 2 | 10 | 133.9 | 1.4 | 25 |
| 3 | 20 | 123.1 | 1.5 | 12.5 |
| 4 | 30 | 180 | 0 | 0 |

Note:
Veh: 1% DMSO, 1% Tween 80, 0.9% NaCl;
Age: P20;
seizure level (level 0: no epileptic response; level 1: fast running and continuous jump; level 2: paroxysmal epilepsy; level 3: tonic epilepsy; level 4: death)

Conclusion: Compared with the control solvent group, single ZD043 (10 and 20 mg/kg) injection can effectively prolong the seizure latency of audiogenic epilepsy in Fmr1 knockout mice, inhibit seizure level and reduce epilepsy mortality (Veh 100%; ZD043-10 mg/kg 25%). That is to say compound ZD043 can effectively intervene the behavior phenotype of the audiogenic epilepsy in Fmr1 knockout mice.

EXAMPLE 5

Pharmacokinetic Experiment in Rats

Dosing Regimen:

Six healthy rats weighing 150-200 g were randomly divided into 3 groups (n=3). The rats were given 10 mL/kg ZD043 by gavage and intravenous injection. The dose of gavage was 20 mg/kg, and the dose of intravenous administration was 10 mg/kg. The drug was formulated in DMSO/Tween 80/saline (5:5:90, v/v/v). The rats were fasted for 12 h before testing, and drinked water ad libitum. 2 h after administration, all rats ate together.

Sampling Time Point and Sample Preparation:

Gavage administration: 0, 0.25, 0.5, 1.0, 2.0, 4.0, 6.0, 8.0 and 24 h after administration;

Intravenous administration: 0, 5 min, 0.25, 0.5, 1.0, 2.0, 4.0, 6.0, 8.0 and 24 h after administration;

0.3 mL of blood was collected at the above time points from the rat eye vein venous plexus, placed in heparinized test tube and centrifugated at 11000 rpm for 5 min. Plasma was separated and the sample was frozed in −20° C. refrigerator.

Experimental Results:

TABLE 3

Pharmacokinetic parameters of rats after gavage and intravenous administration of ZD043

| method of administration | dosage mg/kg | $T_{max}$ h | $C_{max}$ ng/mL | $AUC_{0-t}$ ng/mL * h | $AUC_{0-\infty}$ ng/mL * h | MRT h | $t_{1/2}$ h | F % |
|---|---|---|---|---|---|---|---|---|
| gavage | 20 | 0.25 | 7124.8 | 10491.2 | 10491.2 | 1.06 | 1.30 | 31.6 |
| vein | 10 | 0.083 | 75448.5 | 66417.0 | 66417.0 | 0.62 | 0.43 | / |

After the rats were given 20 mg/kg ZD043 by gavage, plasma concentration peak time $T_{max}$ was 0.25 h, maximal concentration $C_{max}$ was 7124.8 ng/ml; area under the curve $AUC_{0-t}$ was 10491.2 ng·h/ml; and terminal elimination half-life $t_{1/2}$ is 1.302 h. After the rats were administered 10 mg/kg ZD043 by intravenous injection, $AUC_{0-t}$ was 66417.0 ng·h/ml; after normalized the dose, the absolute bioavailability of was 31.6% after the rats was given with 20 mg/kg ZD043 by gavage.

Experimental Conclusion:

From the above experimental results, it can be seen that in the rat pharmacokinetic experiments, the compound ZD043 showed a good absolute bioavailability, up to 31.6%.

EXAMPLE 6

Determination of Brain Tissue Content in Rats

Experimental Procedures:

Six healthy rats weighing 150-200 g were randomly divided into 3 groups (n=3). The rats were given 10 mL/kg by gavage and intravenous injection, and the dose of gavage was 20 mg/kg, and the dose of intravenous administration was 10 mg/kg. The drug was formulated in DMSO/Tween 80/saline (5:5:90, v/v/v). The rats were fasted for 12 h before testing, and drinked water ad libitum. 2 h after administration, all rats ate together.

24 h after administration, the rats were sacrificed by cervical dislocation, and the left and right hippocampus, anterior cortex and cortex were removed under ice bath, and frozen in −20° C. refrigerator.

A physiological saline solution was added (1:10, weight: volume) and the mixture was sufficiently homogenized to form a homogenate. 100 uL homogenate was taken, and 300 uL dichloromethane:methanol (3:2) solution was added, mixed uniformly through vortex oscillation and centrifugated at 14000 rpm for 10 min. The clear liquor was taken. The sample was dried with nitrogen and stored in the 4° C. refrigerator.

Experimental Results:

TABLE 8

The concentration of the drug in the brain tissue of rats after gavage and intravenous administration of ZD043

| Sampling time h | Plasma ng/ml | Cerebrospinal fluid ng/ml | brain ng/g | Csf/P | B/P |
|---|---|---|---|---|---|
| 0.25 | 1240 | 25.5 | 589 | 1/48.6 | 1/2 |
| 1 | 1130 | 21.3 | 559 | 1/53 | 1/2 |
| 3 | 358 | 7.99 | 164 | 1/45 | 1/2.2 |

Experimental Conclusion:

After administration, the compound ZD043 was rapidly absorbed and crossed the blood-brain barrier to the brain tissue, and the drug concentration ratio in the brain and plasma can reach 1/2. Therefore, compound ZD043 has good brain targeting.

EXAMPLE 7

In Vivo Pharmacodynamics Study—Mouse Tail Suspension Experiment

Experimental principle: Tail Suspension Test (TST) is a classic method which can quickly evaluate the efficacy of antidepressant drugs, excitement drugs, and sedative drugs. The principle is to use the status that the mouse give up struggle and enter the unique depression status after the tail was suspended and the attempt to escape was failed. During the experimental process, the immobility time of the animals was recorded to reflect the state of depression, and antidepressants, excitatory drugs can significantly shorten the time.

Experimental method: 20-24 g male mice were selected and the site at 2 cm part from the end of the tail was attached to a horizontal stick, so that the animal entered inverted state, and it's head was about 5 cm from the table, and boards were hung on both sides to separate the animal's sight. The immobility time of the administration group and the control group within 6 min were compared.

Experimental results: The results were shown in FIG. 1.

Experimental conclusion: positive control fluoxetine can significantly improve the "immobility time" in the mouse tail suspension test. The compound ZD043 significantly reduced the "immobility time" in the mouse tail suspension test at 20 mg/kg dose.

EXAMPLE 8

In Vivo Pharmacodynamics Study—Head Twitches Test

Experimental principle: Model Head Thrust Test (HTT) is first raised by Corne et al. in 1963, head twitches syndrome caused by 5-HT receptor excitement may be mediated through the 5-HT$_2$ receptor. The head twitches behavior induced by 5-HTP in mice is more sensitive to antidepressants with different action mechanisms, such as citalopram, fluvoxamine and other 5-HT retake inhibitors, desipramine, maprotiline, nomifensine and other NA retake inhibitors and imipramine acting on both 5-HT and NA system.

Experimental method: 20-24 g male mice were selected. 3 h before the test, 100 mg/kg pargyline was intraperitoneal injected and then intraperitoneal injected with test drugs or saline. 5-HTP (5 mg/kg, ip) was injected 30 min later. After 10 min, the observation was started and the number of mice head twitches in 6 min was recorded. The numbers of the head twitches of experimental group and the saline control group were compared.

Figure 2:
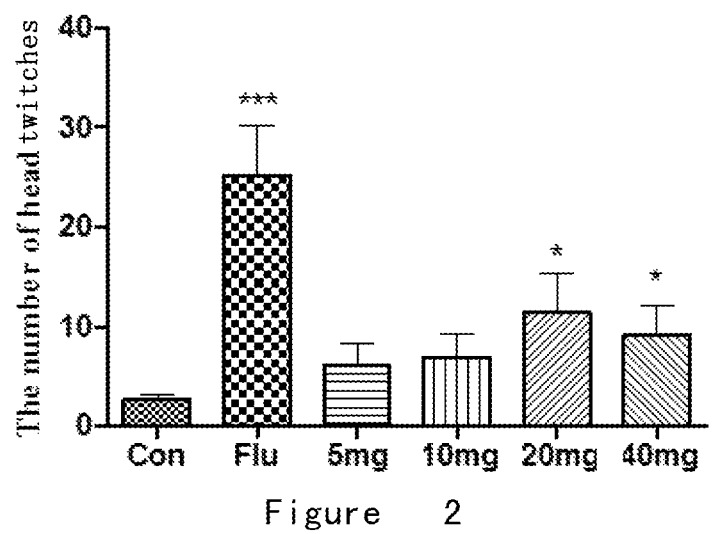
FIG. 2 shows the result of mouse head-twitch test.

The experimental results were shown in FIG. 2.

Experimental conclusion: positive control fluoxetine can significantly improve the "number of head twitches" in the mouse head twitches test. The compound ZD043 was able to increase the "number of head twitches" in the mouse head twitches experiment at 20 mg/kg, which has shown good in vivo pharmacodynamics.

EXAMPLE 9

In Vivo Pharmacodynamics Study—Mouse Forced Swimming Experiment

Experimental principle: The principle of Mouse Forced Swimming Test (FST) is to allow the mouse to swim in a limited space from which it can not escape, thus inducing animal to non-movement state which reflects the animal's desperate behavior.

Experiment name: mouse swimming depression test

Experiment objectives: to observe the effect of the test compound on the depressive status of mice Experimental animals: ICR mice, 20-28 g, both male and female Experimental equipment: organic glass bucket: cylindrical, 25 cm high, 15 cm inner diameter Sample treatment: The test compounds were ground with 1% CMC (sodium carboxymethyl cellulose) aqueous solution to prepare a homogeneous solution. In vivo dose was 5 mg/kg, 10 mg/kg and 20 mg/kg, the compound was oral administered at 0.1 ml/10 g volume/body weight. Positive control drugs (amitriptyline and fluoxetine) were dissolved with 0.9% saline, in vivo dose was 10 mg/kg, administered by intraperitoneal injection at 0.1 ml/10 g volume/body weight. (Note: the mice were fasted for 8 h and drinked water ad libitum before the compound was given.)

Experimental Methods: mice were grouped randomly. On the first day the mice with comparable performances were selected after 15 minutes swimming depression modeling. On the second day of the test, the mice were orally administered the compound. After 1 hour (0.5 hours after intraperitoneal injection), the mice were then put in water to record the immobility time in the later 4 min of 6 min. The compound was tested whether it can significantly shorten the immobility time of forced swimming mice, thus reflecting whether the test compound has antidepressant effects.

Results: (*P<0.05; P<0.01, *P<0.005 vs control.)

TABLE 9 after the mice were orally administrated with ZD043, the immobility time during mice forced swimming experiment

| Group | Dose mg/kg | Number of animal | immobility time (%) Mean ± SEM |
|---|---|---|---|
| Control | / | 10 | 100.00 ± 22.38 |
| CCAmitriptyline | 10 | 10 | 15.34 ± 5.96** |
| Fluoxetine | 10 | 10 | 84.79 ± 12.73 |
| D043 | 5 | 10 | 74.97 ± 18.79 |
|  | 10 | 10 | 66.01 ± 21.08 |
|  | 20 | 10 | 46.50 ± 13.03 |

The results showed that the positive control amitriptyline can significantly improve the "immobility time" during the forced swimming of mice. The compound ZD043 has reduced the "immobility time" during mouse forced swimming process at varying degrees at dose 5 mg/kg, 10 mg/kg and 20 mg/kg, while the improvement effect increases with the dose increases.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula I, or a racemate, R-isomer, S-isomer, pharmaceutically acceptable salt, or mixture thereof:

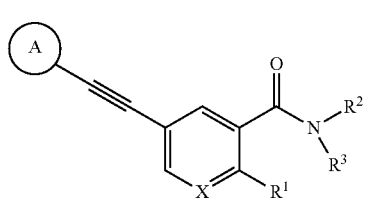

Formula I

X is CH;

R$^1$ is selected from the group consisting of hydrogen, halogen, C1-C6 alkyl, halogen substituted C1-C6 alkyl, and cyano;

R$^2$ and R$^3$ are each independently selected from the group consisting of hydrogen, substituted or unsubstituted phenyl, substituted or unsubstituted 3-7 membered heteroaryl, substituted or unsubstituted 5-7 membered aryl-methylene, and 3-7 membered heterocyclyl-methylene, wherein each heterocyclyl independently contains 1 to 4 heteroatoms selected from oxygen, sulfur and nitrogen; provided that R$^2$ and R$^3$ are not simultaneously hydrogen;

or R² and R³ together with the attached N atom form a group selected from the group consisting of substituted or unsubstituted 5-20 membered hetero spirocyclic ring, and substituted or unsubstituted 4-20 membered fused heterocyclic ring; wherein substituted means one or more hydrogen atoms of the group are substituted by substituents selected from the group consisting of halogen, C1-C6 alkyl, halogen-substituted C1-C6 alkyl, C1-C6 alkoxy, C1-C6 alkoxycarbonyl, halogen-substituted C1-C6 alkoxy, C2-C-6 alkenyl, C2-C6 alkynyl, C3-C8 cycloalkyl, cyano, nitro, amino, hydroxy, hydroxymethyl, carboxy, mercapto, sulfonyl, C6-C10 aryl, and 3-12 membered heterocyclyl; wherein the hetero spirocyclic ring, fused heterocyclic ring or heterocyclyl each independently contains 1 to 4 heteroatoms selected from oxygen, sulfur and nitrogen;

Ⓐ ring is selected from the group consisting of:

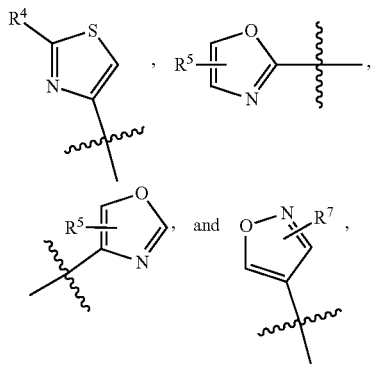

wherein $R^4$, $R^5$, and $R^7$ each represents 1-2 substituents on the heteroring, and each $R^4$, $R^5$, and $R^7$ is a substituent independently selected from the group consisting of hydrogen, halogen, C1-C6 alkyl, halogen-substituted C1-C6 alkyl, C1-C6 alkoxy, cyano, nitro, amino, hydroxyl; and the halogen is F, Cl, Br or I.

2. The compound of claim 1, wherein R² and R³ are each independently selected from the group consisting of hydrogen, substituted or unsubstituted phenyl, substituted or unsubstituted 3-7 membered heteroaryl, substituted or unsubstituted 5-7 membered aryl-methylene, and 3-7 membered heterocyclyl-methylene, wherein each heterocyclyl independently contains 1 to 4 heteroatoms selected from oxygen, sulfur and nitrogen; provided that R² and R³ are not simultaneously hydrogen;

or R² and R³ together with the attached N atom form a group selected from the group consisting of substituted or unsubstituted hetero spirocyclic ring, and substituted or unsubstituted fused heterocyclic ring; wherein substituted means one or more hydrogen atoms of the group are substituted by substituents selected from the group consisting of halogen, C1-C6 alkyl, C1-C6 alkoxy, halogen-substituted C1-C6 alkoxy, cyano, nitro, amino, hydroxy, hydroxymethyl, carboxy, mercapto, sulfonyl, and trifluoromethyl.

3. The compound of claim 1, wherein the

Ⓐ ring is selected from the group consisting of

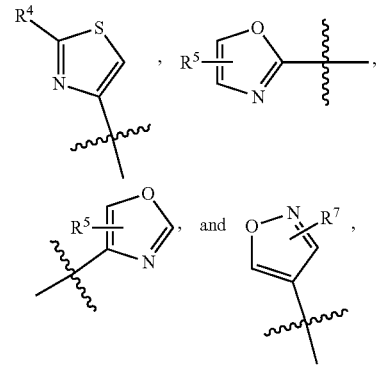

wherein $R^4$, $R^5$, and $R^7$ each represents 1-2 substituents on the heteroring, and each substituent is independently selected from the group consisting of halogen, C1-C6 alkyl, halogen-substituted C1-C6 alkyl, C1-C6 alkoxy, cyano, nitro, amino, and hydroxy.

4. The compound of claim 1, wherein R² is selected from the group consisting of substituted or unsubstituted phenyl, substituted or unsubstituted pyridyl, and substituted or unsubstituted pyrazinyl; wherein substituted means one or more hydrogen atoms of the group are substituted by substituents selected from the group consisting of halogen, C1-C6 alkyl, halogen-substituted C1-C6 alkyl, C1-C6 alkoxy, cyano, nitro, amino, and hydroxy;

R₃ is H;

or R² and R³ together with the connected N atom form a substituted or unsubstituted group selected from the group consisting of:

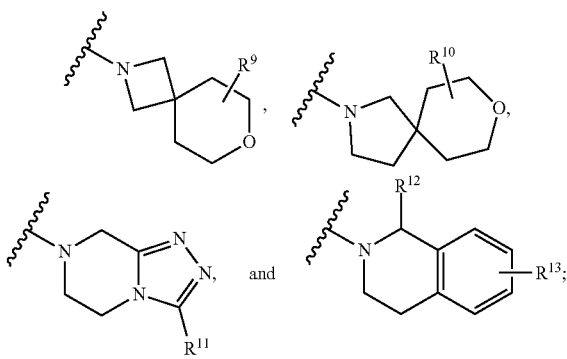

wherein $R^9$, $R^{10}$, and $R^{13}$ each represent 1-4 substituents on any position of the ring, and $R^{11}$ and $R^{12}$ each represent substituents of the ring, and each substituent is independently selected from the group consisting of halogen, C1-C6 alkyl, halogen-substituted C1-C6 alkyl, C1-C6 alkoxy, cyano, nitro, amino, and hydroxy.

5. The compound of claim 1, wherein the compound is selected from the following group:

| No. | Name | Structure |
|---|---|---|
| ZD004 | 2-fluoro-N-(4-fluorophenyl)-5-((2-methyl-thiaZol-4-yl)ethynyl)benzamide | 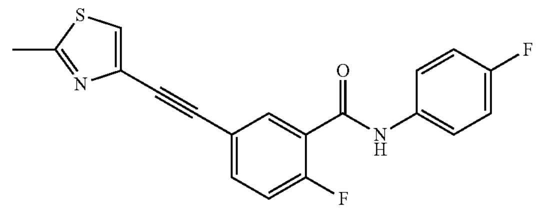 [SMILES: Cc1nc(C#Cc2ccc(F)c(C(=O)Nc3ccc(F)cc3)c2)cs1] |
| ZD005 | (3-((2-methylthiazol-4-yl)ethynyl)phenyl)(3-trifluoromethyl-5,6-dihydro-[1,2,4]triazolo[4,3-a]pyrazin-7(8H)-yl)methanone | 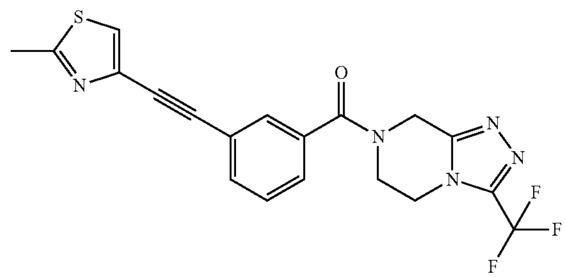 [SMILES: Cc1nc(C#Cc2cccc(C(=O)N3CCn4c(nnc4C(F)(F)F)C3)c2)cs1] |
| ZD007 | (3-((2-methylthiazol-4-yl)phenyl)(7-oxa-2-aza-spiro[3.5]nonan-2-yl)methanone | 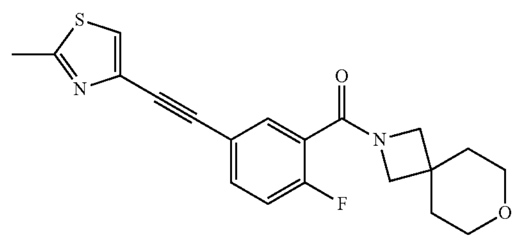 [SMILES: Cc1nc(C#Cc2ccc(F)c(C(=O)N3CC4(CCOCC4)C3)c2)cs1] |
| ZD008 | (3-((2-methylthiazol-4-yl)phenyl)(8-oxa-2-aza-spiro[4.5]dec-2-yl)methanone | 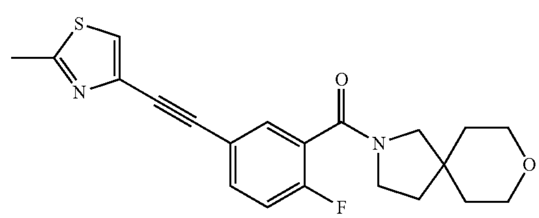 [SMILES: Cc1nc(C#Cc2ccc(F)c(C(=O)N3CCC4(CCOCC4)C3)c2)cs1] |
| ZD009 | N-(4-fluorophenyl)-3-((2-methylthiazol-4-yl)ethynyl)benzamide | 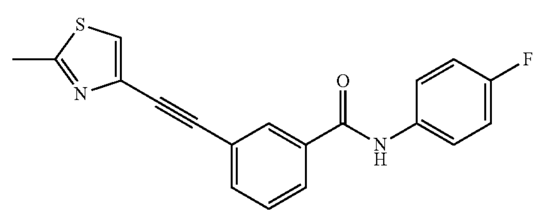 [SMILES: Cc1nc(C#Cc2cccc(C(=O)Nc3ccc(F)cc3)c2)cs1] |
| ZD010 | N-(4-cyanophenyl)-3-((2-methylthiazol-4-yl)ethynyl)benzamide | 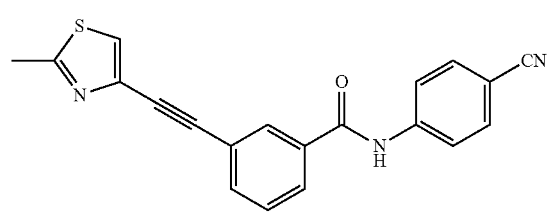 [SMILES: Cc1nc(C#Cc2cccc(C(=O)Nc3ccc(C#N)cc3)c2)cs1] |

| No. | Name | Structure |
|---|---|---|
| ZD011 | (1-methyl-3,4-dihydro-isoquinolin-2(1H-yl-3-((2-methyl-thiazol-4-yl)ethynyl)phenyl)methanone | 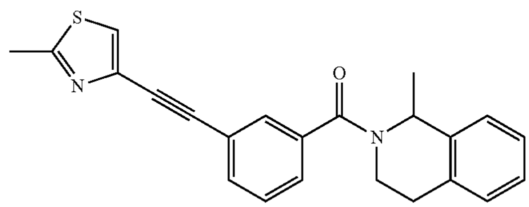 [SMILES: Cc1nc(C#Cc2cccc(C(=O)N3CCc4ccccc4C3C)c2)cs1] |
| ZD012 | (3,4-dihydro-isoquinolin-2(1H)-yl)(3-((2-methyl-thiazol-4-yl)ethynyl)phenyl)methanone | 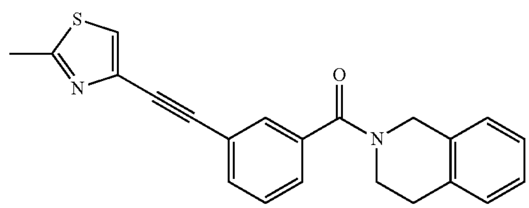 [SMILES: Cc1nc(C#Cc2cccc(C(=O)N3CCc4ccccc4C3)c2)cs1] |
| ZD013 | 3-((2-methylthiazol-4-ylethynyl)-N-(pyridin-3-yl)benzamide | 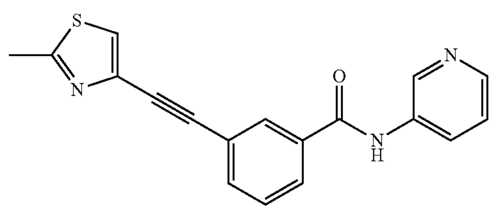 [SMILES: Cc1nc(C#Cc2cccc(C(=O)Nc3cccnc3)c2)cs1] |
| ZD014 | 3-((2-methylthiazol-4-ylethynyl)-N-phenylbenzamide | 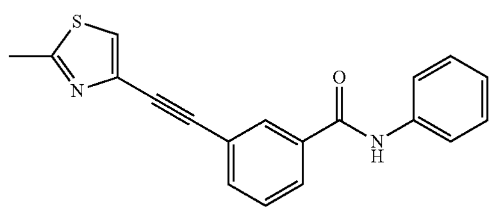 [SMILES: Cc1nc(C#Cc2cccc(C(=O)Nc3ccccc3)c2)cs1] |
| ZD015 | 3-((2-methylthiazol-4-ylethynyl)-N-(4-(trifluoromethyl)phenyl)benzamide | 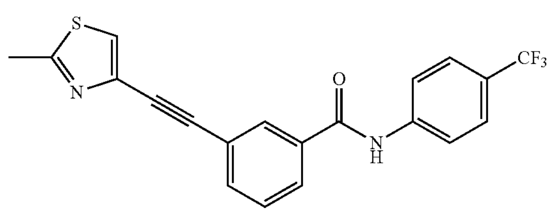 [SMILES: Cc1nc(C#Cc2cccc(C(=O)Nc3ccc(C(F)(F)F)cc3)c2)cs1] |
| ZD017 | N-(3-fluorophenyl)-3-((2-methylthiazol-4-yl)ethynyl)benzamide | 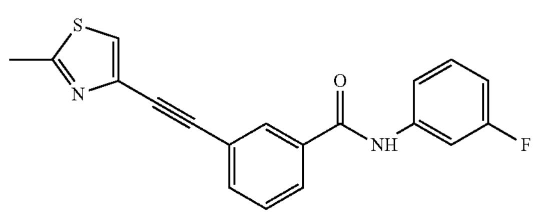 [SMILES: Cc1nc(C#Cc2cccc(C(=O)Nc3cccc(F)c3)c2)cs1] |
| ZD019 | N-(3-cyanophenyl)-3-((2-methylthiazol-4-yl)ethynyl)benzamide | 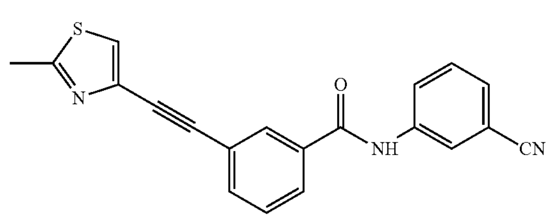 [SMILES: Cc1nc(C#Cc2cccc(C(=O)Nc3cccc(C#N)c3)c2)cs1] |

-continued

| No. | Name | Structure |
|---|---|---|
| ZD037 | 2-chloro-N-(4-fluorophenyl)-5-((2-methyl-thiazol-4-yl)ethynyl)benzamide | 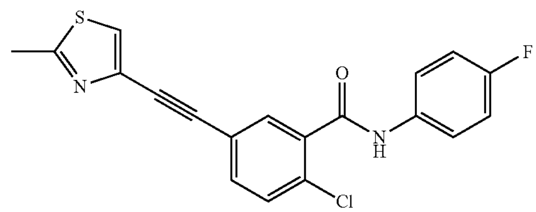 |
| ZD041 | N-(4-fluorophenyl)-2-methyl-5-((2-methyl-thiazol-4-yl)ethynyl)benzamide | 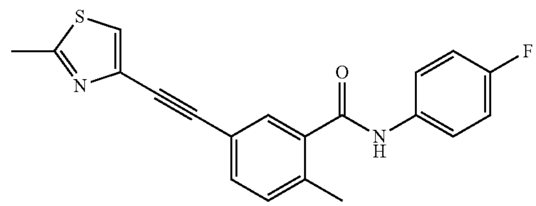 [SMILES: Cc1nc(C#Cc2ccc(C)c(C(=O)Nc3ccc(F)cc3)c2)cs1] |
| ZD043 | 2-fluoro-5-((2-methylthiazol-4-ylethynyl)-N-(pyridin-3-yl)benzamide | 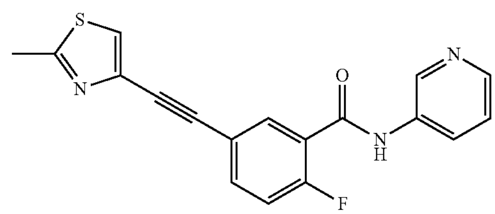 |
| ZD045 | N-(4-cyanophenyl)2-fluoro-5-((2-methyl-thiazol-4-yl)ethynyl)benzamide | 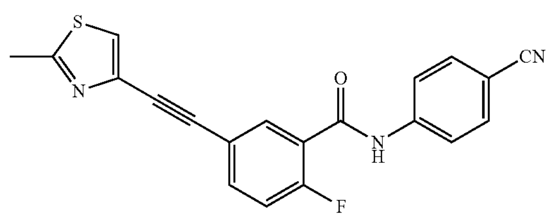 [SMILES: Cc1nc(C#Cc2ccc(F)c(C(=O)Nc3ccc(C#N)cc3)c2)cs1] |
| ZD047 | (3,4-dihydro-isoquinolin-2(1H)-yl)(2-fluoro-5-((2-methyl-thiazol-4-yl)ethynyl)phenyl)methanone | 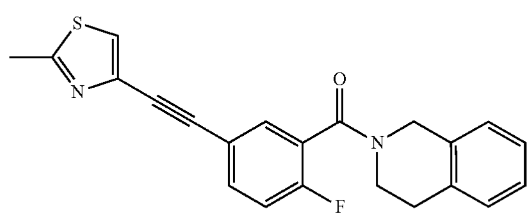 |
| ZD049 | (2-fluoro-5-((2-methyl-thiazol-4-yl)ethynyl)phenyl)(1-methyl-3,4-dihydro-isoquinolin-2(1H)-yl)methanone | 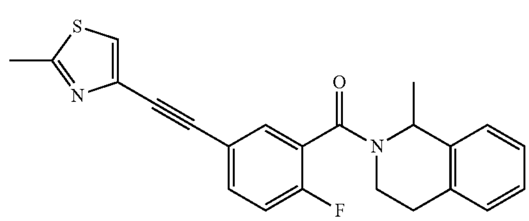 |
| ZD057 | 2-fluoro-5-((2-methylthiazol-4-yl)ethynyl)-N-benzoylaniline | 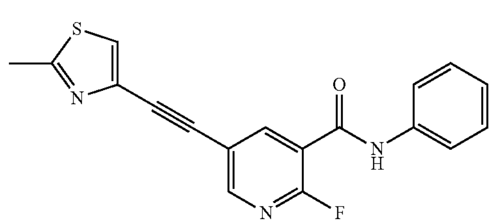 [SMILES: Cc1nc(C#Cc2cnc(F)c(C(=O)Nc3ccccc3)c2)cs1] |

-continued

| No. | Name | Structure |
|---|---|---|
| ZD058 | 2-cyano-5-((2-methylthiazol-4-ylethynyl)-N-(pyridin-3-yl)benzamide | 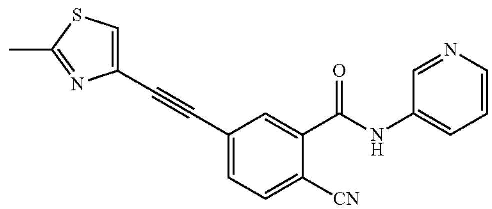 [SMILES: Cc1nc(C#Cc2ccc(C#N)c(C(=O)Nc3cccnc3)c2)cs1] |
| ZD059 | 5-((2-methylthiazol-4-ylethynyl)-N-(pyridin-3-yl)-2-(trifluoromethyl)benzamide | 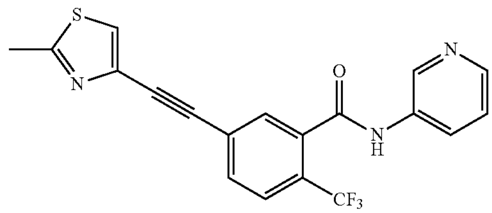 [SMILES: Cc1nc(C#Cc2ccc(C(F)(F)F)c(C(=O)Nc3cccnc3)c2)cs1] |
| ZD060 | N-(4-fluorophenyl)-5-((2-methylthiazol-4-yl)ethynyl)-2-(trifluoromethyl)benzamide | 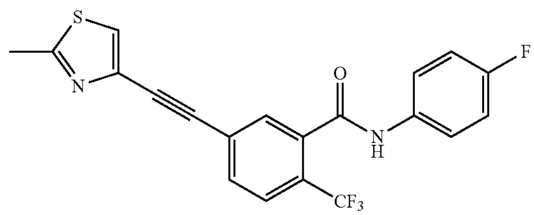 [SMILES: Cc1nc(C#Cc2ccc(C(F)(F)F)c(C(=O)Nc3ccc(F)cc3)c2)cs1] |
| ZD061 | 2-cyano-N-(4-fluorophenyl)-5-((2-methylthiazol-4-yl)ethynyl)benzamide | 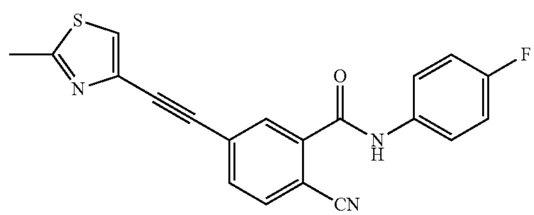 |
| ZD062 | 4-((2-methylthiazol-4-yl)ethynyl)-2-(1,2,3,4-dihydroisoquinolin-2-carbonyl)benzonitrile | 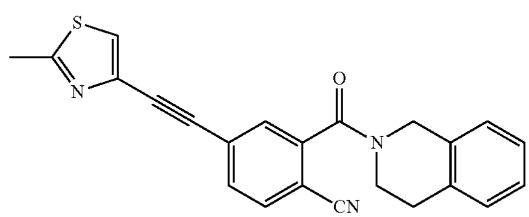 [SMILES: Cc1nc(C#Cc2ccc(C#N)c(C(=O)N3CCc4ccccc4C3)c2)cs1] |
| ZD063 | (3,4-dihydro-isoquinolin-2(1H)-yl)(5-((2-methyl-thiazol-4-yl)ethynyl)-2-(trifluoromethyl)phenyl)methanone | 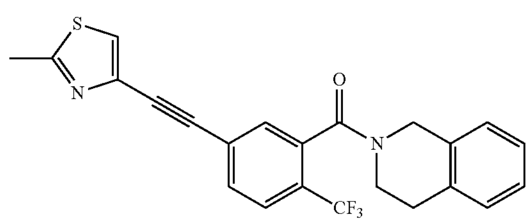 [SMILES: Cc1nc(C#Cc2ccc(C(F)(F)F)c(C(=O)N3CCc4ccccc4C3)c2)cs1] |
| ZD064 | 2-fluoro-N-(2-fluorophenyl)-5-((2-methylthiazol-4-yl)ethynyl)benzamide | 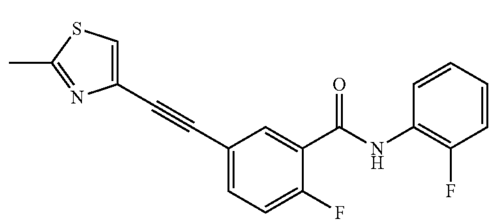 [SMILES: Cc1nc(C#Cc2ccc(F)c(C(=O)Nc3ccccc3F)c2)cs1] |

| No. | Name | Structure |
|---|---|---|
| ZD065 | 2-fluoro-N-(3-fluorophenyl)-5-((2-methylthiazol-4-yl)ethynyl)benzamide | 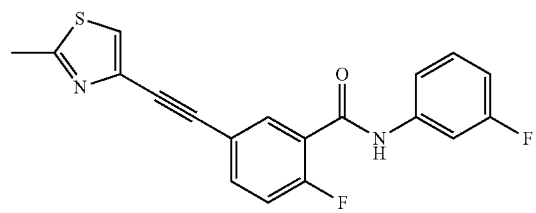 [SMILES: Cc1nc(C#Cc2ccc(F)c(C(=O)Nc3cccc(F)c3)c2)cs1] |
| ZD066 | N-(3,4-difluorophenyl)-2-fluoro-5-((2-methylthiazol-4-yl)ethynyl)benzamide | 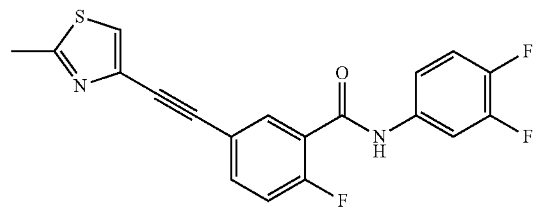 [SMILES: Cc1nc(C#Cc2ccc(F)c(C(=O)Nc3ccc(F)c(F)c3)c2)cs1] |
| ZD067 | N-(2,4-difluorophenyl)-2-fluoro-5-((2-methylthiazol-4-yl)ethynyl)benzamide | 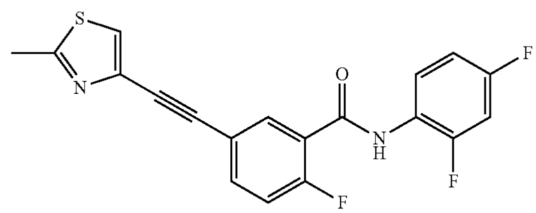 |
| ZD068 | N-(4-chlorophenyl)-2-fluoro-5-((2-methyl-thiazol-4-yl)ethynyl)benzamide | 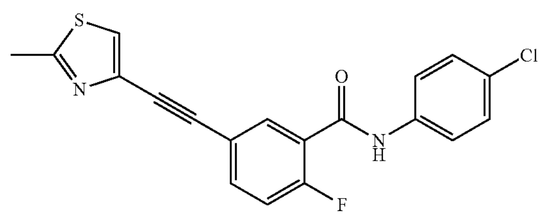 [SMILES: Cc1nc(C#Cc2ccc(F)c(C(=O)Nc3ccc(Cl)cc3)c2)cs1] |
| ZD069 | 2-fluoro-5-((2-methylthiazol-4-ylethynyl)-N-(4-(trifluoromethyl)phenyl)benzamide | 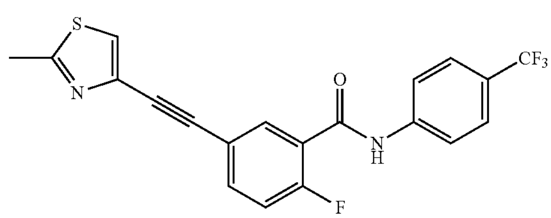 [SMILES: Cc1nc(C#Cc2ccc(F)c(C(=O)Nc3ccc(C(F)(F)F)cc3)c2)cs1] |
| ZD070 | 2-fluoro-N-(4-methoxyphenyl)-5-((2-methylthiazol-4-yl)ethynyl)benzamide | 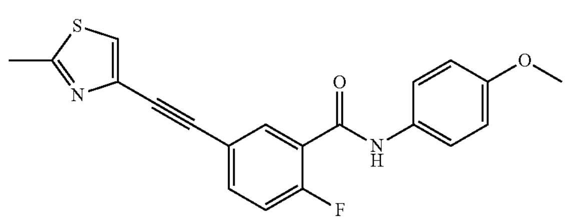 |
| ZD071 | 2-fluoro-5-((2-methylthiazol-4-ylethynyl)-N-(pyridin-2-yl)benzamide | 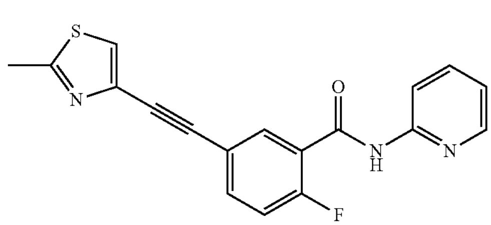 [SMILES: Cc1nc(C#Cc2ccc(F)c(C(=O)Nc3ccccn3)c2)cs1] |

| No. | Name | Structure |
| --- | --- | --- |
| ZD072 | 2-fluoro-5-((2-methylthiazol-4-ylethynyl)-N-(pyridin-4-yl)benzamide | 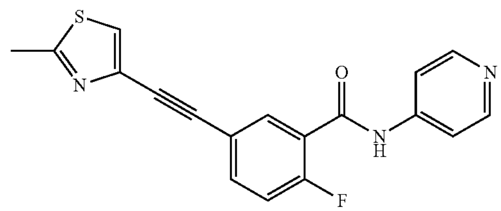 [SMILES: Cc1nc(C#Cc2ccc(F)c(C(=O)Nc3ccncc3)c2)cs1] |
| ZD073 | 2-fluoro-N-(6-fluoropyridin-3-yl)-5-((2-methylthiazol-4-yl)ethynyl)benzamide | 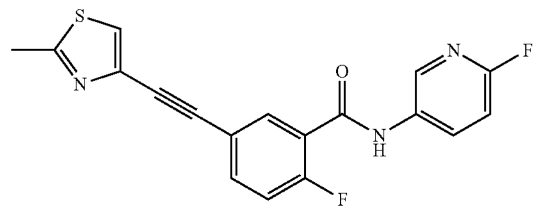 [SMILES: Cc1nc(C#Cc2ccc(F)c(C(=O)Nc3ccc(F)nc3)c2)cs1] |
| ZD074 | N-(6-chloropyridin-3-yl)-2-fluoro-5-((2-methylthiazol-4-yl)ethynyl)benzamide | 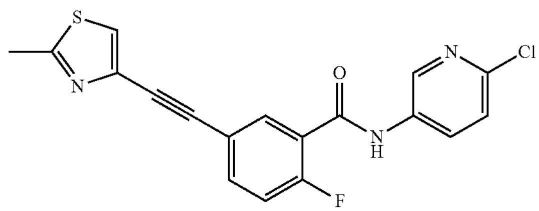 [SMILES: Cc1nc(C#Cc2ccc(F)c(C(=O)Nc3ccc(Cl)nc3)c2)cs1] |
| ZD075 | 2-fluoro-5-((2-methylthiazol-4-ylethynyl)-N-(p-methylphenyl)benzamide | 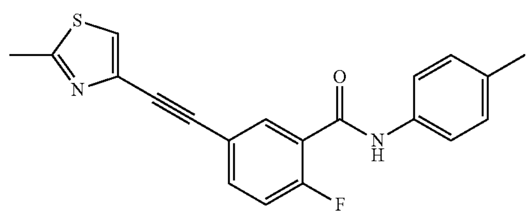 |
| ZD076 | 2-fluoro-N-(pyridin-3-yl)-5-(thiazol-4-ylethynyl)benzamide | 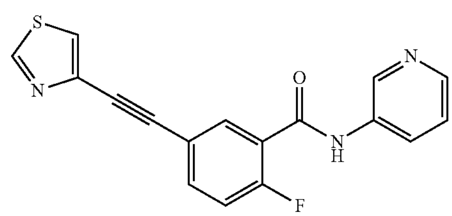 [SMILES: O=C(Nc1cccnc1)c1cc(C#Cc2cscn2)ccc1F] |
| ZD077 | 2-fluoro-5-((2-fluorothiazol-4-yl)ethynyl)-N-(pyridin-3-yl)benzamide | 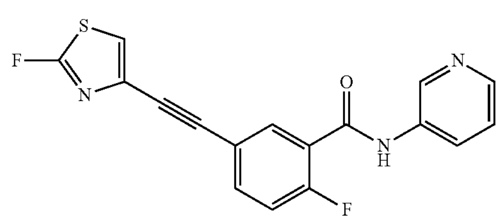 [SMILES: O=C(Nc1cccnc1)c1cc(C#Cc2csc(F)n2)ccc1F] |
| ZD078 | 5-((2-chlorothiazol-4-ylethynyl)-2-fluoro-N-(pyridin-3-yl)benzamide | 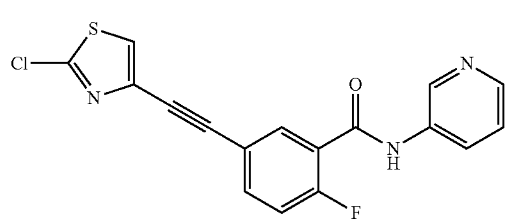 [SMILES: O=C(Nc1cccnc1)c1cc(C#Cc2csc(Cl)n2)ccc1F] |

| No. | Name | Structure |
|---|---|---|
| ZD079 | 2-fluoro-N-(pyridin-3-yl)-5-((2-(trifluoromethyl)thiazol-4-yl)ethynyl)benzamide | 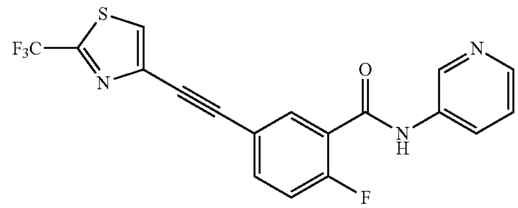 [SMILES: O=C(Nc1cccnc1)c1cc(C#Cc2csc(C(F)(F)F)n2)ccc1F] |
| ZD089 | 2-fluoro-5-((2-methyloxazol-4-ylethynyl)-N-(pyridin-3-yl)benzamide | 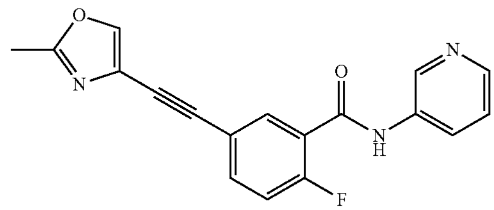 [SMILES: Cc1nc(C#Cc2ccc(F)c(C(=O)Nc3cccnc3)c2)co1] |
| ZD090 | 2-fluoro-N-(4-fluorophenyl)-5-((2-methyloxazol-4-yl)ethynyl)benzamide | 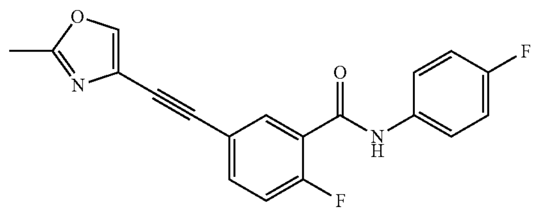 |
| ZD091 | (3,4-dihydro-isoquinolin-2(1H)-yl)(2-fluoro-5-((2-methyloxazol-4-yl)ethynyl)phenyl)methanone | 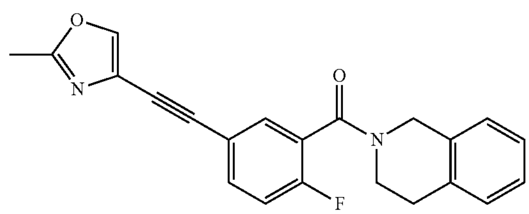 |
| ZD092 | (3,4-dihydro-isoquinolin-2(1H)-yl)(5-((3-5-dimethylisoxazol-4-yl)ethynyl)-2-fluorophenyl)methanone | 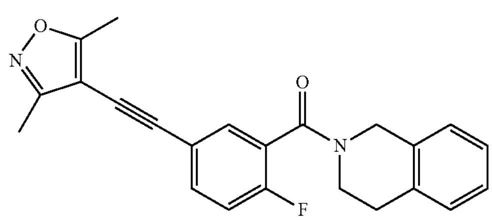 [SMILES: Cc1noc(C)c1C#Cc1ccc(F)c(C(=O)N2CCc3ccccc3C2)c1] |
| ZD093 | 5-((3,5-dimethylisoxazol-4-ylethynyl)-2-fluoro-N-(pyridin-3-yl)benzamide | 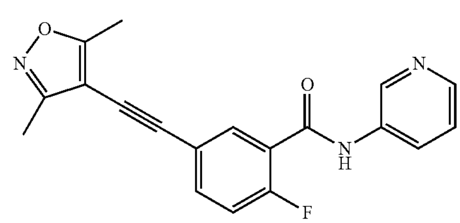 [SMILES: Cc1noc(C)c1C#Cc1ccc(F)c(C(=O)Nc2cccnc2)c1] |
| ZD094 | 5-((3,5-dimethylisoxazol-4-ylethynyl)-2-fluoro-N-(4-fluorophenyl)benzamide | 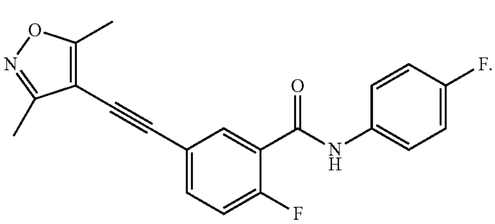 [SMILES: Cc1noc(C)c1C#Cc1ccc(F)c(C(=O)Nc2ccc(F)cc2)c1] |

6. A pharmaceutical composition comprising the compound of claim 1, and a pharmaceutically acceptable carrier.

7. A method of allosterically modulating metabotropic glutamate receptor subtype 5 (mGluR5) in a subject, the method comprising administering to the subject the pharmaceutical composition of claim 6.

8. The method of claim 7, wherein the method is for selective inhibition of mGluR5.

9. A method of treating a disease associated with metabotropic glutamate receptor subtype 5 (mGluR5) in a subject, the method comprising administering to the subject the pharmaceutical composition of claim 6.

10. A pharmaceutical composition comprising the compound of claim 5, and a pharmaceutically acceptable carrier.

11. A method of allosterically modulating metabotropic glutamate receptor subtype 5 (mGluR5) in a subject, the method comprising administering to the subject the pharmaceutical composition of claim 10.

12. The method of claim 11, wherein the method is for selective inhibition of mGluR5.

13. A method of treating a disease associated with metabotropic glutamate receptor subtype 5 (mGluR5) in a subject, the method comprising administering to the subject the pharmaceutical composition of claim 10.

14. The method of claim 9, wherein the disease is associated with the central nervous system and psychiatric system.

15. The method of claim 9, wherein the disease is selected from the group consisting of fragile X chromosome syndrome, Parkinson's disease levodopa-induced dyskinesia (PD-LID), gastroesophageal reflux disease (GERD), autism, pain, anxiety, depression, and drug addiction.

16. The method of claim 13, wherein the disease is associated with the central nervous system and psychiatric system.

17. The method of claim 13, wherein the disease is selected from the group consisting of fragile X chromosome syndrome, Parkinson's disease levodopa-induced dyskinesia (PD-LID), gastroesophageal reflux disease (GERD), autism, pain, anxiety, depression, and drug addiction.

* * * * *